United States Patent
Harding et al.

(10) Patent No.: US 11,585,733 B2
(45) Date of Patent: Feb. 21, 2023

(54) HAZARDOUS CONTAMINANT COLLECTION KIT AND RAPID TESTING

(71) Applicant: Becton, Dickinson and Company, Franklin Lakes, NJ (US)

(72) Inventors: Weston F. Harding, Lehi, UT (US); Erik K. Witt, Wyckoff, NJ (US); Austin Jason McKinnon, Herriman, UT (US); Ray Isaacson, Layton, UT (US); Bart Peterson, Farmington, UT (US); Marcel Arantes Souza, Lehi, UT (US); Matthew Oshinski, Oak Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 170 days.

(21) Appl. No.: 16/134,271

(22) Filed: Sep. 18, 2018

(65) Prior Publication Data
US 2019/0120727 A1    Apr. 25, 2019

Related U.S. Application Data

(60) Provisional application No. 62/561,540, filed on Sep. 21, 2017.

(51) Int. Cl.
*C12M 1/30*   (2006.01)
*G01N 1/02*   (2006.01)
(Continued)

(52) U.S. Cl.
CPC .................. *G01N 1/02* (2013.01); *C12M 1/30* (2013.01); *C12M 1/34* (2013.01); *G01N 21/03* (2013.01);
(Continued)

(58) Field of Classification Search
CPC ....... B01L 3/5023; B01L 3/5029; G01N 1/02; G01N 33/00; G01N 21/77; G01N 33/5302;
(Continued)

(56) References Cited

U.S. PATENT DOCUMENTS

| 1,853,238 A | 4/1932 | Shields |
| D229,689 S | 12/1973 | Dragotta |

(Continued)

FOREIGN PATENT DOCUMENTS

| CN | 104819865 A | 8/2015 |
| CN | 107102103 A | 8/2017 |

(Continued)

OTHER PUBLICATIONS

Becton Dickinson—BD HD Check Analyzer—Nursing Brochure; Mar. 2018, in 8 pages.
(Continued)

*Primary Examiner* — Rebecca M Giere
*Assistant Examiner* — Xiaoyan Zou
(74) *Attorney, Agent, or Firm* — Knobbe, Martens, Olson & Bear, LLP

(57) ABSTRACT

Contamination detection systems, kits, and techniques are described for testing surfaces for the presence of hazardous contaminants, while minimizing user exposure to these contaminants. Even trace amounts of contaminants can be detected. A collection kit provides a swab that is simple to use, easy to hold and grip, allows the user to swab large areas of a surface, and keeps the user's hands away from the surface being tested. The kit also provides open and closed fluid transfer mechanism to transfer the collected fluid to a detection device while minimizing user exposure to hazardous contaminants in the collected fluid. Contamination detection kits can rapidly collect and detect hazardous drugs, (Continued)

including trace amounts of antineoplastic agents, in healthcare settings at the site of contamination.

20 Claims, 42 Drawing Sheets

(51) Int. Cl.
    *G01N 21/03*     (2006.01)
    *G01N 21/77*     (2006.01)
    *G01N 33/53*     (2006.01)
    *G01N 33/00*     (2006.01)
    *C12M 1/34*     (2006.01)
    *G01N 1/00*     (2006.01)

(52) U.S. Cl.
    CPC ............. *G01N 21/77* (2013.01); *G01N 33/00* (2013.01); *G01N 33/5302* (2013.01); *G01N 2001/002* (2013.01); *G01N 2001/028* (2013.01); *G01N 2021/7759* (2013.01); *G01N 2021/7773* (2013.01)

(58) Field of Classification Search
    CPC ....... G01N 2001/028; G01N 2001/002; G01N 2021/7759; C12M 1/30
    USPC .......................................................... 436/501
    See application file for complete search history.

(56) References Cited

U.S. PATENT DOCUMENTS

| | | | |
|---|---|---|---|
| 3,841,973 A | 10/1974 | Wilkins et al. | |
| 4,278,437 A | 7/1981 | Haggar | |
| 4,353,868 A | 10/1982 | Joslin et al. | |
| 4,430,013 A | 2/1984 | Kaufman | |
| 4,707,450 A | 11/1987 | Nason | |
| 4,724,307 A | 2/1988 | Dutton et al. | |
| 4,956,302 A | 9/1990 | Gordon et al. | |
| 5,243,865 A | 9/1993 | Hsu et al. | |
| 5,373,748 A | 12/1994 | Lioy et al. | |
| 5,422,273 A | 6/1995 | Garrison et al. | |
| 5,511,654 A | 4/1996 | de la Rocha | |
| 5,511,934 A | 4/1996 | Bracchi et al. | |
| 5,543,115 A * | 8/1996 | Karakawa | B01L 3/508 422/535 |
| D383,851 S | 9/1997 | Wong | |
| 5,798,273 A | 8/1998 | Shuler et al. | |
| 5,823,592 A | 10/1998 | Kalidindi et al. | |
| 5,888,758 A | 3/1999 | Wu et al. | |
| 5,902,982 A | 5/1999 | Lappe | |
| D425,625 S | 5/2000 | Niermann | |
| D438,979 S | 2/2001 | Gomes et al. | |
| 6,267,722 B1 | 7/2001 | Anderson et al. | |
| 6,382,036 B1 | 5/2002 | Woodmansee | |
| 6,541,269 B1 | 4/2003 | Ramana et al. | |
| 6,723,290 B1 | 4/2004 | Wardlaw | |
| 6,924,153 B1 | 8/2005 | Boehringer et al. | |
| D520,643 S | 5/2006 | Clarke et al. | |
| 7,114,403 B2 | 10/2006 | Wu et al. | |
| D558,357 S | 12/2007 | Byrd et al. | |
| D559,397 S | 1/2008 | Eriksson et al. | |
| D560,281 S | 1/2008 | Kozak et al. | |
| D574,507 S | 8/2008 | Muir et al. | |
| D594,131 S | 6/2009 | Nguyen | |
| 7,837,939 B2 * | 11/2010 | Tung | A61B 10/0045 422/410 |
| D640,795 S | 6/2011 | Jackson et al. | |
| 8,128,871 B2 | 3/2012 | Petruno et al. | |
| 8,486,717 B2 | 7/2013 | O'Farrell et al. | |
| 8,828,653 B2 | 9/2014 | Zook et al. | |
| D743,046 S | 11/2015 | Poll et al. | |
| D743,571 S | 11/2015 | Jackson et al. | |
| 9,488,585 B2 | 11/2016 | Emeric et al. | |
| 9,857,372 B1 | 1/2018 | Pulitzer et al. | |
| 9,857,375 B2 | 1/2018 | Konishi et al. | |
| D859,683 S | 9/2019 | Harding et al. | |
| D882,817 S | 4/2020 | Norton et al. | |
| D898,220 S | 10/2020 | Esala et al. | |
| 10,883,901 B1 | 1/2021 | Henzl et al. | |
| D910,200 S | 2/2021 | Reber et al. | |
| 10,916,058 B2 | 2/2021 | Isaacson et al. | |
| 11,002,642 B2 | 5/2021 | Oshinski et al. | |
| D923,195 S | 6/2021 | Harding et al. | |
| 11,123,736 B2 | 9/2021 | Mitra et al. | |
| 11,125,661 B2 | 9/2021 | Myres, III et al. | |
| D933,203 S | 10/2021 | Zhang | |
| 11,199,529 B2 | 12/2021 | Harding et al. | |
| 11,280,801 B2 | 3/2022 | Oshinski | |
| 11,360,001 B2 | 6/2022 | West | |
| 11,380,074 B2 | 7/2022 | Isaacson et al. | |
| 11,385,146 B2 | 7/2022 | Harding et al. | |
| 11,391,748 B2 | 7/2022 | Isaacson et al. | |
| 2002/0001539 A1 | 1/2002 | Dicesare et al. | |
| 2002/0035869 A1 | 3/2002 | Schroder et al. | |
| 2003/0015044 A1 | 1/2003 | Knothe | |
| 2003/0086074 A1 | 5/2003 | Braig et al. | |
| 2004/0018634 A1 | 1/2004 | Hajizadeh et al. | |
| 2004/0248106 A1 | 12/2004 | Leonard et al. | |
| 2005/0084842 A1 | 4/2005 | O'Connor | |
| 2005/0106753 A1 | 5/2005 | Wu et al. | |
| 2005/0136540 A1 | 6/2005 | Quine et al. | |
| 2005/0136553 A1 | 6/2005 | Kaylor et al. | |
| 2005/0181517 A1 | 8/2005 | Chandler et al. | |
| 2005/0250141 A1 | 11/2005 | Lambert et al. | |
| 2006/0074347 A1 * | 4/2006 | Eguchi | B01L 3/5029 600/572 |
| 2006/0115805 A1 | 6/2006 | Hansen et al. | |
| 2006/0216196 A1 | 9/2006 | Satoh et al. | |
| 2007/0137319 A1 | 6/2007 | Nacson et al. | |
| 2007/0244368 A1 | 10/2007 | Bayliff et al. | |
| 2007/0276786 A1 | 11/2007 | Piedmonte | |
| 2008/0118397 A1 | 5/2008 | Slowey et al. | |
| 2009/0015273 A1 | 1/2009 | Gossen et al. | |
| 2009/0061534 A1 | 3/2009 | Sharrock | |
| 2009/0223635 A1 | 9/2009 | Lawless | |
| 2010/0077843 A1 | 4/2010 | Doraisamy et al. | |
| 2011/0117025 A1 | 5/2011 | Dacosta et al. | |
| 2011/0201099 A1 | 8/2011 | Anderson et al. | |
| 2011/0295620 A1 | 12/2011 | Loscalzo et al. | |
| 2012/0011944 A1 | 1/2012 | Maughan et al. | |
| 2012/0044264 A1 | 2/2012 | Lee et al. | |
| 2012/0107956 A1 | 5/2012 | Boehringer et al. | |
| 2012/0264229 A1 | 10/2012 | Wan | |
| 2012/0282154 A1 | 11/2012 | Slowey et al. | |
| 2013/0203627 A1 | 8/2013 | Moll et al. | |
| 2013/0253295 A1 | 9/2013 | Tolosa et al. | |
| 2013/0280143 A1 | 10/2013 | Zucchelli et al. | |
| 2014/0017812 A1 | 1/2014 | Smith et al. | |
| 2014/0080129 A1 | 3/2014 | Klunder et al. | |
| 2014/0121487 A1 | 5/2014 | Faybishenko et al. | |
| 2014/0176603 A1 | 6/2014 | Kumar et al. | |
| 2014/0183256 A1 | 7/2014 | Calio et al. | |
| 2014/0210857 A1 | 7/2014 | Liu et al. | |
| 2014/0309556 A1 | 10/2014 | Fletcher et al. | |
| 2015/0132795 A1 | 5/2015 | Griswold et al. | |
| 2015/0211987 A1 | 7/2015 | Burg et al. | |
| 2015/0241358 A1 | 8/2015 | Burg et al. | |
| 2015/0302662 A1 | 10/2015 | Miller | |
| 2016/0019716 A1 | 1/2016 | Huang et al. | |
| 2016/0041167 A1 | 2/2016 | Campbell et al. | |
| 2016/0057413 A1 | 2/2016 | Zhou et al. | |
| 2016/0077013 A1 | 3/2016 | Attar et al. | |
| 2016/0078680 A1 | 3/2016 | Reif et al. | |
| 2016/0258874 A1 | 9/2016 | Truex | |
| 2016/0313323 A1 | 10/2016 | Jakubowicz | |
| 2017/0016045 A1 | 1/2017 | McDaniel | |
| 2017/0036205 A1 | 2/2017 | Bishop et al. | |
| 2017/0072393 A1 | 3/2017 | Jackson et al. | |
| 2017/0153185 A1 | 6/2017 | Kisner et al. | |
| 2017/0154438 A1 | 6/2017 | Kisner et al. | |
| 2017/0182492 A1 | 6/2017 | Liu | |
| 2017/0184585 A1 | 6/2017 | Markovsky et al. | |
| 2018/0247024 A1 | 8/2018 | Divine et al. | |

(56) References Cited

U.S. PATENT DOCUMENTS

| | | |
|---|---|---|
| 2018/0259429 A1 | 9/2018 | Adams |
| 2018/0293350 A1 | 10/2018 | Dimov et al. |
| 2018/0372595 A1* | 12/2018 | Pais .................. B01F 13/0059 |
| 2019/0035153 A1 | 1/2019 | Dange |
| 2019/0086295 A1 | 3/2019 | Oshinski et al. |
| 2019/0086296 A1 | 3/2019 | West |
| 2019/0086305 A1 | 3/2019 | Harding et al. |
| 2019/0086380 A1 | 3/2019 | Harding et al. |
| 2019/0086431 A1 | 3/2019 | Isaacson et al. |
| 2019/0088026 A1 | 3/2019 | Isaacson et al. |
| 2019/0120727 A1 | 4/2019 | Harding et al. |
| 2019/0376966 A1 | 12/2019 | Pulitzer et al. |
| 2020/0241020 A1 | 7/2020 | Oshinski |
| 2020/0298240 A1 | 9/2020 | Oshinski et al. |
| 2021/0192850 A1 | 6/2021 | Isaacson et al. |
| 2021/0255066 A1 | 8/2021 | Oshinski et al. |
| 2022/0099648 A1 | 3/2022 | Harding et al. |
| 2022/0206021 A1 | 6/2022 | Oshinski |

FOREIGN PATENT DOCUMENTS

| | | | |
|---|---|---|---|
| JP | 2002502045 A | 1/2002 | |
| JP | 2002504684 A | 2/2002 | |
| JP | 2006284279 A | 10/2006 | |
| JP | 2007212391 A | 8/2007 | |
| JP | 2016539338 A | 12/2016 | |
| WO | WO 1995/25948 | 9/1995 | |
| WO | WO 2005/068969 | 7/2005 | |
| WO | WO 2009/018473 | 2/2009 | |
| WO | WO 2010/001296 | 1/2010 | |
| WO | WO 2011/095599 | 8/2011 | |
| WO | WO 2013/036913 | 3/2013 | |
| WO | WO 2014/015076 | 1/2014 | |
| WO | WO 2014/025415 | 2/2014 | |
| WO | WO 2015/187335 | 12/2015 | |
| WO | WO-2016040642 A1 * | 3/2016 | ......... G01N 35/1095 |
| WO | WO 2016/078919 | 5/2016 | |
| WO | WO 2016/090176 | 6/2016 | |
| WO | WO 2017/222833 | 12/2017 | |

OTHER PUBLICATIONS

Becton Dickinso—BD HD Check Analyzer—Pharmacy Brochure; Mar. 2018, in 6 pages.

Becton Dickinson—BD Diagnostics Preanalytical Systems—Product Catalogue 2014-15; 2013, Retrieved from internet: <URL:https://www.bd.com/be/dutch/pdfs/PAS_BNL_Prod_Cat_2014_2015_LR_Full_Catalogue.pdf> in 31 pages.

ChemoGlo, LLC, "ChemoGlo™—Detecting and Removing Hazardous Drugs"; available for download at https://web.archive.org/web/20150801115335/http://chemoglo.com/ at least as early as Aug. 1, 2015; 1 page.

ChemoGlo, LLC, ChemoGlo™ User Manual; available for download at https://web.archive.org/web/20150801115335/http://chemoglo.com/ at least as early as Aug. 1, 2015; 11 pages.

Becton Dickinson—Veritor™ System—For Rapid Detection of Respiratory Syncytial Virus (RSV), Aug. 2017, Retrieved from the internet: <URL: https://www.bd.com/en-us/offerings/capabilities/microbiology-solutions/point-of-care-testing/veritor-system> in 16 pages.

Preprocess, Inc., Sampling and Analytical Technique Considerations for Microbial Surface Swab Testing. 2015; Retrieved from the internet: <URL:http://www.preprocessinc.com/files/documents/d5840edf837f077be7b12e53494ed5b8.pdf> in 3 pages.

Technical Service Consultants Ltd., TS/15-T Product Specification Sheet; Issue #5 of Jun. 6, 2016; Retrieved from the Internet: URL: <http://www.tscswabs.co.uk/uploads/images/product-pdfs/product_specification/spec_TS15-T.pdf> in 20 pages.

International Search Report and Written Opinion dated Nov. 23, 2018 for Int'l Application No. PCT/US2018/051426.

De Keuckelaere et al., "Semi-Direct Lysis of Swabs and Evaluation of Their Efficiencies to Recover Human Noroviruses GI and GII from Surfaces", Food Environ Virol. (Jun. 2014) 6(2): 132-139.

Henderson S.J., "Augmented Reality Interfaces for Procedural Tasks", Doctoral Thesis; Columbia University, Apr. 14, 2011, 82 pages.

National Infection Service (England), Detection and enumeration of bacteria in swabs and other environmental samples. National Infection Service Food Water and Environmental Microbiology Standard Method, Sep. 1, 2017; 22 pages.

* cited by examiner

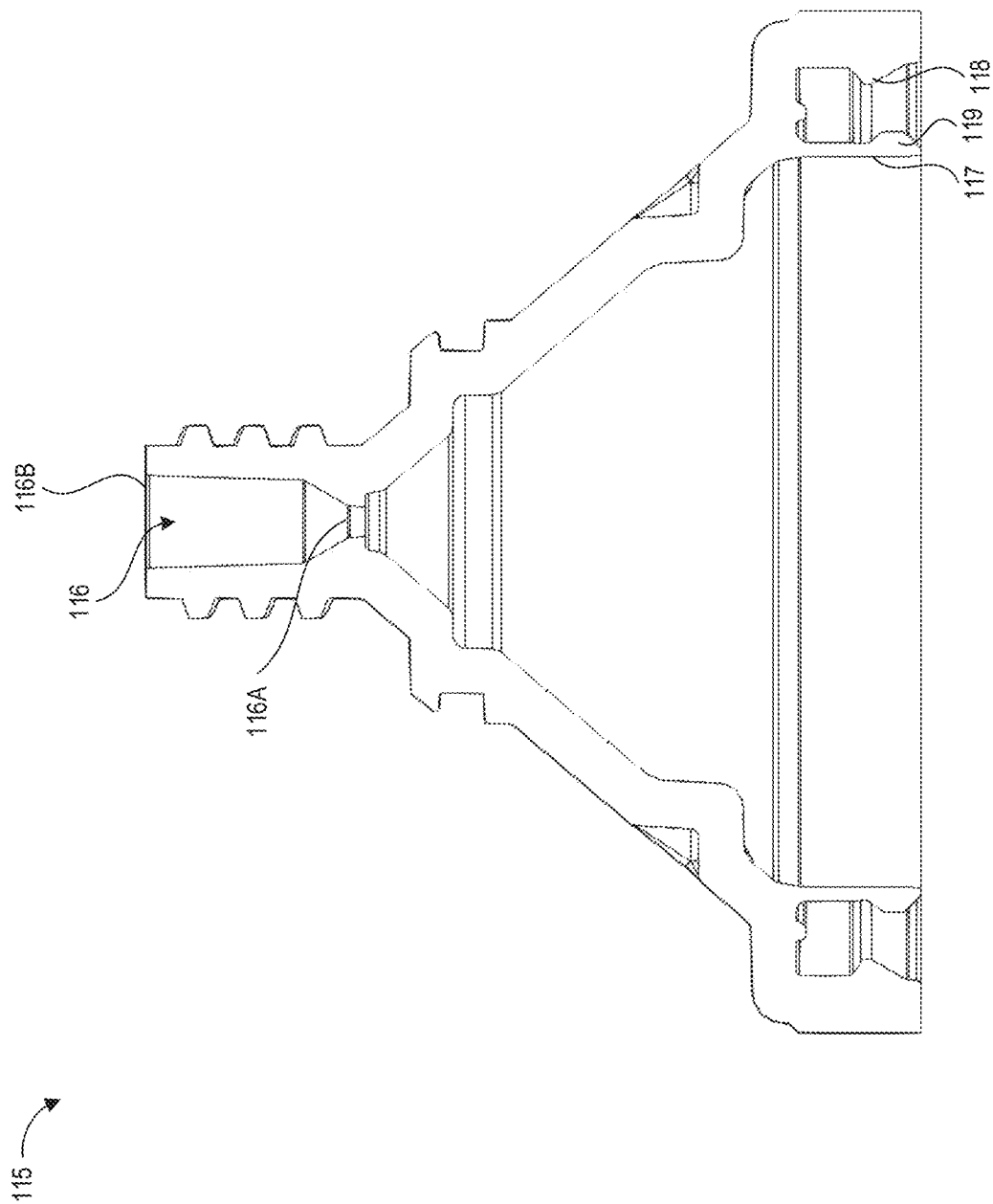

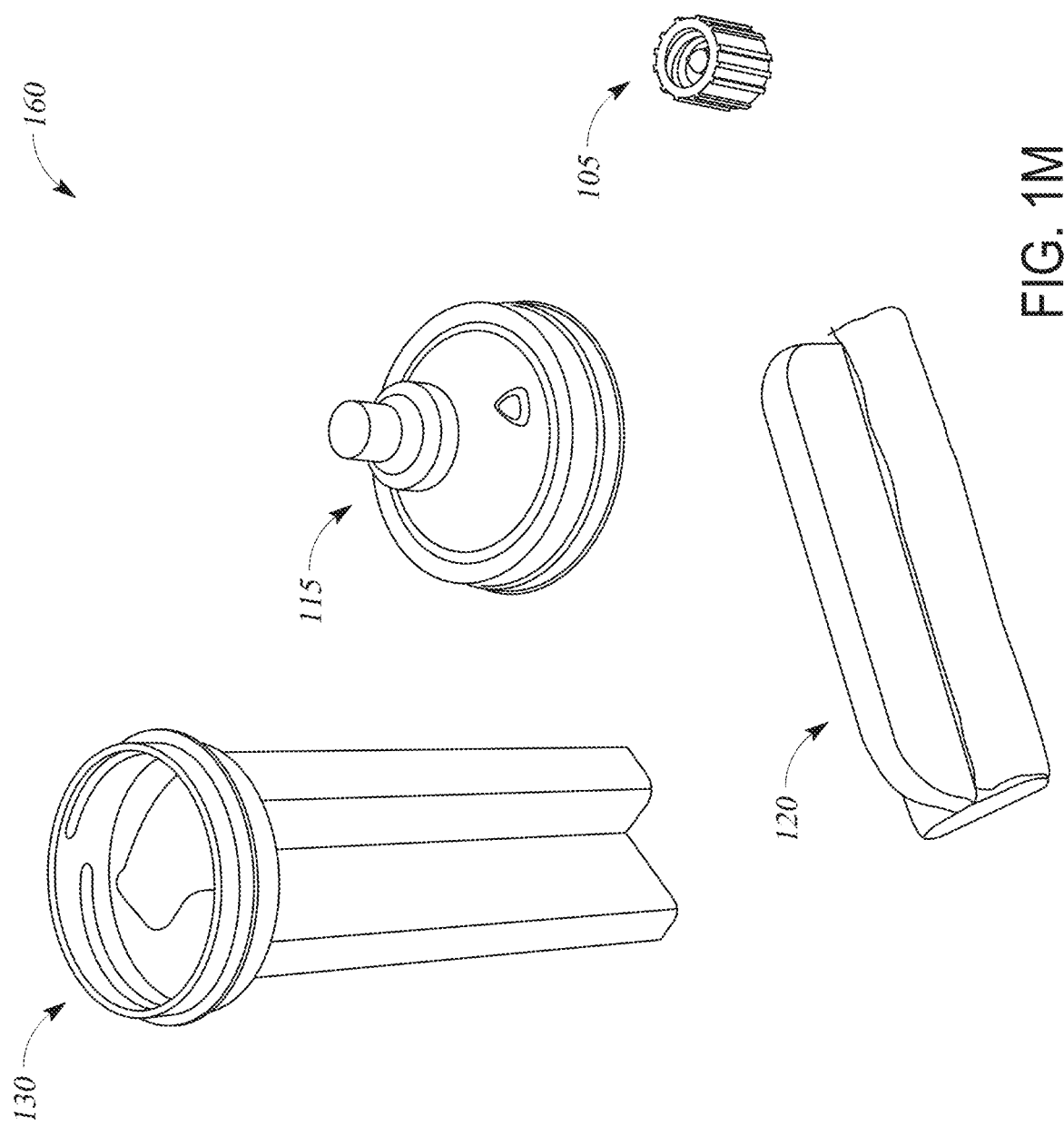

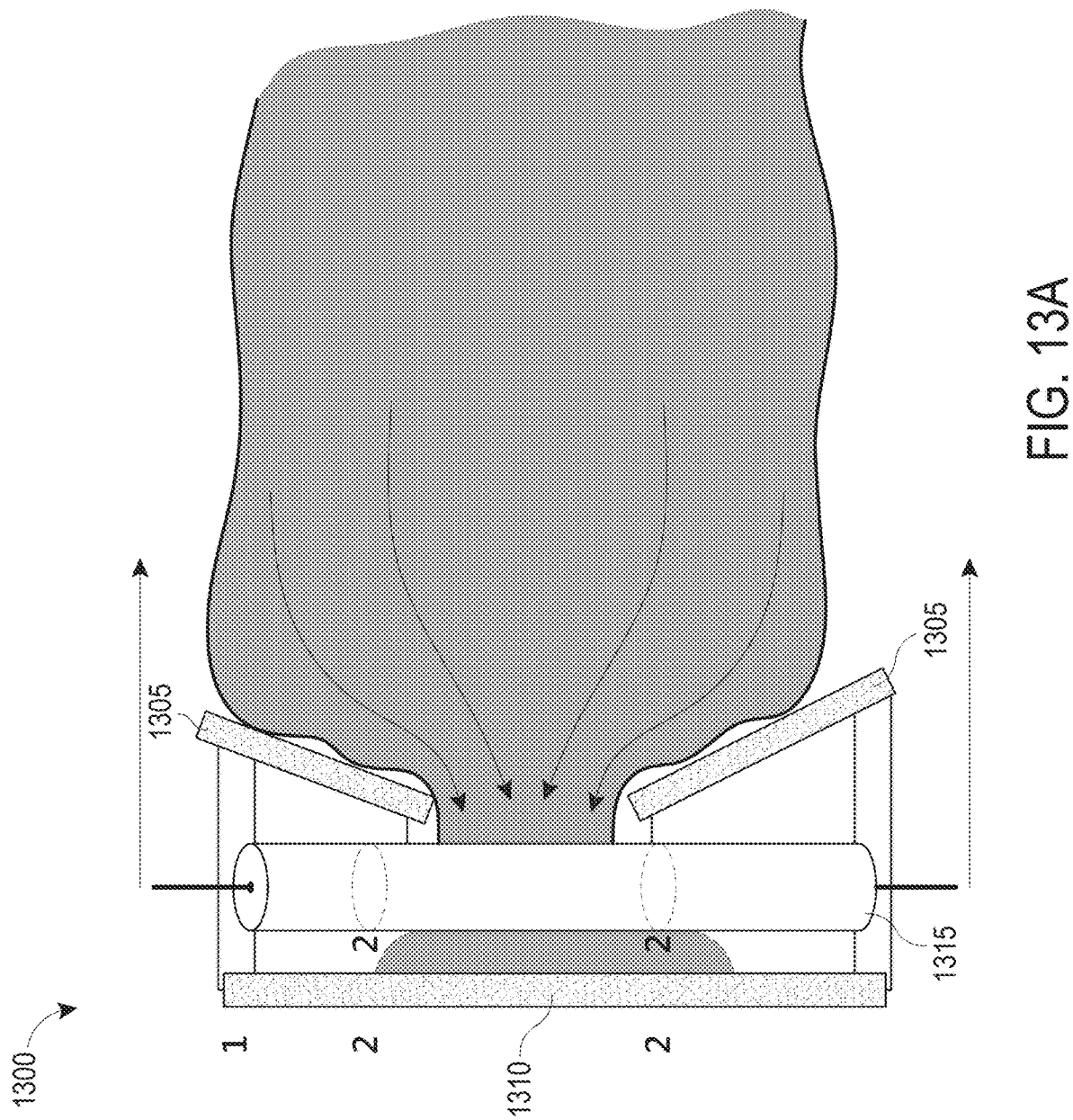

HAZARDOUS CONTAMINANT COLLECTION KIT AND RAPID TESTING

CROSS-REFERENCE TO RELATED APPLICATIONS

This application claims the benefit of U.S. Provisional Patent Application No. 62/561,540, filed on Sep. 21, 2017, entitled "HAZARDOUS CONTAMINANT COLLECTION KIT AND RAPID TESTING," the contents of which are hereby incorporated by reference herein.

TECHNICAL FIELD

The systems and methods disclosed herein are directed to environmental contaminant testing, and, more particularly, to a test kit for detecting the presence and/or quantity of antineoplastic agents.

BACKGROUND

Antineoplastic drugs are used to treat cancer, and are most often found in a small molecule (like fluoruracil) or antibody format (like Rituximab). Detection of antineoplastic drugs is critical for determining if there is contamination/leakage in hospital/pharmacy areas where the drugs are used and/or dispensed.

The nature of antineoplastic agents make them harmful to healthy cells and tissues as well as the cancerous cells. Precautions should be taken to eliminate or reduce occupational exposure to antineoplastic agents for healthcare workers. Pharmacists who prepare these drugs and nurses who may prepare and administer them are the two occupational groups who have the highest potential exposure to antineoplastic agents. Additionally, physicians and operating room personnel may also be exposed through the treatment of patients. Hospital staff, such as shipping and receiving personnel, custodial workers, laundry workers and waste handlers, all have the potential to be exposed to these drugs during the course of their work. The increased use of antineoplastic agents in veterinary oncology also puts these workers at risk for exposure to these drugs.

SUMMARY

Existing approaches to detecting a hazardous drug contamination require the user to manually handle sample swabs directly by hand, press the swab material by hand when wiping a test surface, place the sampled swabs into a test tube/vial, and send the sample-impregnated swab to an outside laboratory for testing. Directly handling a swab embedded with hazardous contamination is potentially dangerous for the test user. Further, these existing approaches use a small cotton swabs on a stick which covers very little surface area, requiring significant work and time from the user. Further, the results can come back weeks (sometimes up to nine weeks) after when the test was taken, delaying any decontamination response.

These and other problems are addressed in embodiments of the collection and testing kit described herein that avoids further spread and exposure of contamination during the process of collecting the sample and quickly provides accurate test results at the site and time of testing. The present technology provides a collection kit and detection system for testing of various surfaces in healthcare settings for the presence of antineoplastic agents while minimizing user exposure to these agents. The kit is capable of detecting even trace amounts of antineoplastic agents and of providing results quickly (including immediately after collection). Advantageously, testing and detection occur at the location of the collection. The kit provides a swab that is simple to use, easy to hold and grip, allows for swabbing of large surfaces, and keeps the user's hands away from the surface being tested. Beneficially, the kit also provides a collection kit that is fluid-tight and provides for leak-free transfer of the collected fluid from the collection kit to the detection system.

One suitable detection system includes an immunoassay device. Immunoassay devices play an important role in areas such as clinical chemistry and have been made portable for use in the field. Immunoassay technology provides simple and relatively quick means for determining the presence of analytes in a subject sample. Analytes are substances of interest or clinical significance that may be present in biological or non-biological fluids. The analytes can include antibodies, antigens, drugs, or hormones. The analyte of interest is generally detected by reaction with a capture agent, which yields a device more easily detected and measured than the original analyte. Detection methods can include a change in absorbance, a change in color, change in fluorescence, change in luminescence, change in electrical potential at a surface, change in other optical properties, or any other easily measured physical property indicating the presence or absence of an analyte in a sample.

Accordingly, one aspect relates to a hazardous contamination detection system comprising a collection device comprising a buffer solution configured to lift a hazardous contaminant from a test surface when the buffer solution is applied to the test surface, an absorbent swab material configured to absorb at least a portion of the buffer solution and to contact the test surface to collect the hazardous contaminant, a handle having a first end coupled to the absorbent swab material, a second end spaced apart from the first end, and an elongate length extending therebetween, a fluid-tight container having an interior volume dimensioned to encase the handle and the absorbent swab material and the buffer solution, the container having a nozzle including an orifice sized to provide controlled release of a volume of the buffer solution from the interior volume; and a detection device comprising an assay test strip positioned to receive the volume of the buffer solution released from the container, the assay test strip comprising at least one reaction zone configured to produce an optically-detectable change in appearance in the presence of the hazardous contaminant, and an image sensor positioned to receive light reflected from the at least one reaction zone and configured to generate signals representing an intensity of the received light, and control electronics configured to analyze the signals and determine the presence of the hazardous contaminant in the at least one reaction zone.

Some embodiments of the system further comprise a demarcation guide specifying an area of the test surface to be tested for contamination by the hazardous contaminant. In some embodiments of the system, the control electronics are configured to determine whether the hazardous contaminant is in contact with the at least one reaction zone based at least partly on the intensity of the signals and the area of the test surface.

In some embodiments of the system, the assay test strip comprises a sample receiving zone for receiving the volume of the buffer solution released through the orifice of the nozzle; and a length of material extending between the sample receiving zone and the at least one reaction zone and configured to wick at least the received buffer solution from the sample receiving zone to the at least one reaction zone.

In some embodiments of the system, the container comprises an open end having an aperture into the interior volume; and a releasable portion of the container including an attachment mechanism configured to releasably couple to the container over the open end to provide a fluid-tight seal with the interior volume of the container with the handle and the absorbent swab material and the buffer solution sealed within the interior volume, the nozzle, and a cap releasably coupled to the nozzle.

In some embodiments of the system, the handle has a first T-shaped cross section, and wherein the interior volume of the container has a second T-shaped cross section sized to receive the first T-shaped cross section of the handle.

In some embodiments of the system, at least a portion of the container is flexible such that the interior volume can be compressed to expel the volume of the buffer solution from the interior volume through the orifice of the nozzle.

In some embodiments of the system, the detection device comprises a network connection interface, and wherein the control electronics are configured to send data representing whether the hazardous contaminant is in contact with the at least one reaction zone to at least one remote computing device over a network via the network interface.

Another aspect relates to a hazardous contaminant collection device comprising a fluid-tight container having an interior volume; a buffer solution configured to lift a hazardous contaminant from a test surface when applied to the test surface; an absorbent swab material configured to absorb at least some of the buffer solution and to contact the test surface to collect the hazardous contaminant; and a handle having a first end coupled to the absorbent swab material, a second end spaced apart from the first end, and an elongate length extending therebetween; wherein the interior volume is dimensioned to contain the handle and absorbent swab material and the at least some of the buffer solution, the container having a nozzle including an orifice sized to provide controlled release of a volume of the buffer solution from the interior volume.

In some embodiments of the device, the container comprises an open end having an aperture into the interior volume; and a releasable portion of the container including an attachment mechanism configured to releasably couple to the container over the open end to provide a fluid-tight seal with the interior volume of the container with the handle and absorbent swab material and buffer solution sealed within the interior volume, the nozzle, and a cap releasably coupled to the nozzle. In some embodiments of the device, the attachment mechanism comprises threading along an interior surface of the releasable portion, and wherein the open end of the container comprises corresponding threading along an exterior surface of the open end.

In some embodiments of the device, the handle comprises a T-shaped cross section defining a swab holding member having a flat first surface and a second surface spaced apart from the first surface, and a handle portion extending away from the second surface. In some further embodiments, the absorbent swab material comprises two layers of fabric coupled to the first surface of the flat swab holding member. In some further embodiments, a width of the absorbent swab material is greater than a width of the flat first surface swab holding member. In some further embodiments, the absorbent swab material is coupled to the flat first surface of the swab holding member at opposing edges of the swab material with a gap between a central portion of the absorbent swab material and the flat first surface of the swab holding member. In some further embodiments, the interior volume of the container has a T-shaped cross section corresponding to the T-shaped cross section of the handle.

In some embodiments of the device, the nozzle comprises a channel leading to the orifice, wherein a cross-section of the channel is shaped to release the volume of the buffer fluid one drop at a time.

Another aspect relates to a method of testing a test surface for the presence of a hazardous contaminant, the method comprising removing an absorbent swab material coupled to an elongate handle from fluid-tight packaging, the absorbent swab material pre-moistened with a first volume of a buffer solution configured to lift the hazardous contaminant from the test surface, wherein the absorbent swab material is impregnated with the first volume of the buffer solution; wiping the test surface with the absorbent swab material to collect particles of the hazardous contaminant from the test surface; inserting the absorbent swab material into an open end of a fluid-tight container, the fluid-tight container comprising a well containing a second volume of the buffer solution and a cap to seal the well; sealing the fluid-tight container with the cap to isolate the first and second volumes of the buffer solution within the fluid-tight container; agitating the fluid-tight container to release at least some of the collected particles of the hazardous contaminant into the buffer solution; opening a sealable orifice of the cap; transferring a third volume of the buffer solution from the fluid-tight container to an assay test strip through the sealable orifice; inserting the assay test strip into an assay reader device; and based on an output of the assay reader device, identifying that the hazardous contaminant is present on the test surface.

Some embodiments of the method further comprise compressing an interior volume of the fluid-tight container to expel the third volume of the buffer solution through the sealable orifice. Some embodiments of the method further comprise sealing the sealable orifice after transferring the third volume of the buffer solution.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 1F-1G illustrate various views of an example snap fit removable top of the collection device of FIG. 1A.

FIGS. 1M-1O illustrate various views and components of a collection kit.

FIGS. 13A and 13B illustrate another example of a collection device including a squeegee.

DETAILED DESCRIPTION

Introduction

Figure 1A:
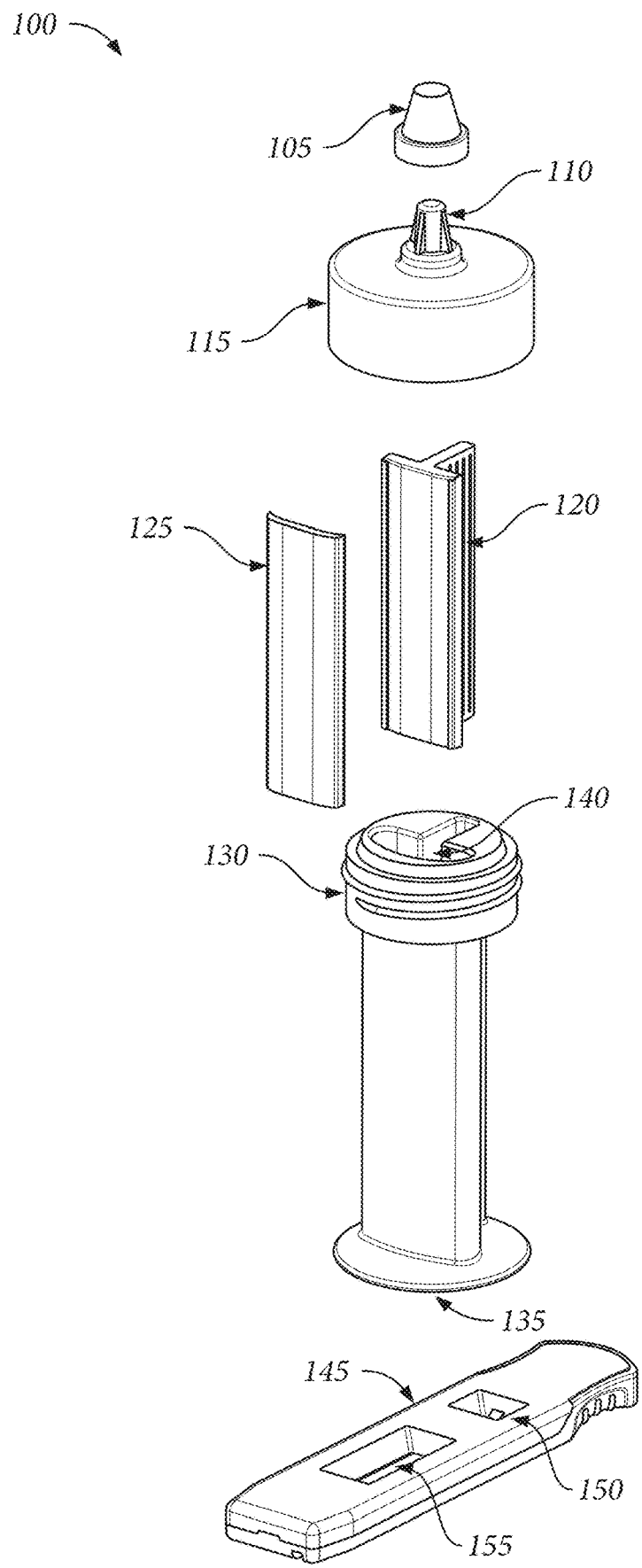
FIG. 1A illustrates an example of an open system contaminant collection device and open system detection device.

Embodiments of the disclosure relate to systems and techniques for detection of hazardous environmental contaminants, such as but not limited to antineoplastic drugs used in the treatment of cancer, while minimizing exposure of the test operator to the contaminants. A kit for such testing can include a collection device and a testing device. Throughout this disclosure, example systems, kits, and methods will be described with reference to collection, testing, and detection of antineoplastic agents, but it will be understood that the present technology can be used to collect, test, and detect any particle, molecule, or analyte of interest.

A collection device can include a swab and a container for sealing the swab after collection of the antineoplastic agent. The swab can be constructed from a special material having desired pickup efficiency and shedding efficiency for detecting trace amounts of antineoplastic agents, and is provided on a handle having sufficient length so that the user can swab a surface without physically contacting the surface or the swab. A liquid, for example a buffer solution, can be provided within the container so that the user removes a pre-wetted swab to swipe the surface in one implementation. In another implementation, the user sprays the surface with a liquid and collects this liquid with the swab.

The collection kit can further include a template, guide, or instructions to delineate a specific dimensional area for testing. In order to obtain an accurate test result for contaminants that are hazardous even in trace amounts, a precise method of marking (demarcation) and then performing the sampling procedure (for example, to sample all of the demarcated area and only the demarked area) can be a very important step to ensure an accurate result. There are several factors that can be key to obtaining an accurate drug concentration measurement given in the following formula:

$$C = \frac{\alpha * A * \eta_p * \eta_e}{V_b}$$

where C is the concentration, $\alpha$ is the contamination surface density (ng/ft^2), A is the surface area swabbed and tested, $\eta_p$ is the pick-up efficiency, $\eta_e$ is the extraction from the swab density, and $V_b$ is the fluid volume of the buffer solution used to help extract and carry the contamination to the test strip. A goal of the described testing can be to have a high concentration signal with low variability. Excessive "noise" or variation in the variables may cause the test to either give false positive or false negative results. Test kits described herein can include mechanisms and/or instructions to users to assist in reducing the variation of each term in the above concentration equation.

After swabbing the surface, the user places the swab into the container and the handle forms a liquid-tight seal when engaged with the container. The handle can additionally lock to the container. The container can contain a buffer or diluent solution used as an agent to help remove the particles of interest embedded on the swab material into the fluid of the container. The container advantageously prevents liquid from spilling and contaminating surfaces or users, but provides for controlled release of fluid to a detection system. Non-limiting examples of such systems are referred to herein as "open system contaminant collection devices" and "open system detection devices." Some implementations of the container can provide a fluid tight seal between the sample vial and the test strip so that harmful fluids, drugs or vapors would be contained and not vented into the atmosphere and possibly creating additional harm to the user. For example, the container can be structured to attach and/or seal to the detection system to provide a closed path for fluid transfer between the container and the detection system. Non-limiting examples of such systems are referred to herein as "closed system contaminant collection devices" and "closed system detection devices."

The testing device can be an immunoassay reader, for example a lateral flow assay and reader device, with an interface that alerts the user to the presence and/or degrees of contamination. Fluid can be released from the container onto a receiving zone of an assay test strip in some embodiments. The assay test strip can then be inserted into a reader to image the indicators on the strip, analyze the image(s), determine a level of contamination, and report the determined level of contamination to the user. The reader can have more than one method of entering data regarding the sample and can have various ways of saving, storing, displaying, uploading and alerting the appropriate personnel when unacceptable levels of contamination are detected.

In one example, after detecting contamination in an initial test there can be several possible next steps. A first option can be to remove the fluid tight connector and place the sample onto another more sensitive test strip to determine an advanced level of detection. A second option can be to further dilute the sample to provide one or more additional levels of dilution, and to then take a hot or high magnitude signal. Once measured the dilution amount can be taken into effect and an actual concentration can be calculated based on the result and dilution amount.

The described swabs, buffer solutions, and test devices can be configured to pick up and detect trace amounts of antineoplastic agents and/or chemotherapeutic drugs in some embodiments. It will be appreciated that the described systems can be adapted to collect and detect quantities of other biohazardous chemicals, drugs, pathogens, or substances in other embodiments. Further, the disclosed systems can be used in forensic, industrial, and other settings.

Specific collection device embodiments illustrated and described herein are characterized as having either an "open" or "closed" fluid transfer mechanism. However, it will be appreciated that the illustrated fluid transfer mechanisms are provided as non-limiting examples and that the disclosed swabs, containers, and other collection device aspects of each embodiment can, in various implementations, have either an open or a closed fluid transfer mechanism.

Although the disclosed detection devices are typically described herein with reference to test strips and lateral flow assay reader devices, it will be appreciated that the described hazardous contaminant detection aspects described herein can be implemented in any suitable detection system. For example, features described herein can be implemented in reader devices that analyze other types of assays, such as but not limited to molecular assays, and provide a test result. Further, the collected fluid can be transferred to a centrifuge, spectrometer, chemical assay, or other suitable test device to determine the presence and/or concentration of one or more hazardous substances in the sample.

Drugs successfully treat many types of illnesses and injuries, but virtually all drugs have side effects associated with their use. Not all adverse side effects classify as hazardous, however. In the present disclosure, the term "hazardous drugs" is used according to the meaning adopted by the American Society of Health-System Pharmacists (ASHP), which refers to a drug as hazardous if studies in animals or humans have indicated that exposures to them have any one of four characteristics: genotoxicity; carcinogenicity; teratogenicity or fertility impairment; and serious organ damage or other toxic manifestation at low doses in experimental animals or treated patients.

Although described in the example context of ascertaining the concentration of hazardous drugs such as antineoplastic agents, it will be appreciated that the disclosed test strips and reading techniques for extending competitive assay dynamic range can be used to detect the presence and/or concentration of any analyte of interest. An analyte can include, for example, drugs (both hazardous and non-hazardous), antibodies, proteins, haptens, nucleic acids and amplicons.

Various embodiments will be described below in conjunction with the drawings for purposes of illustration. It should be appreciated that many other implementations of the disclosed concepts are possible, and various advantages can be achieved with the disclosed implementations.

Overview of Example Open System Contaminant Collection Devices

A hazardous contamination detection kit can be used to identify and measure a specific area of surfaces to be tested and collect hazardous drugs from those surfaces, for example in a pharmacy or in patient care/nursing areas. This kit includes a collection device for sampling the surfaces for possible contamination due to hazardous drugs. After sampling, fluid from the collection kit can be transferred to a detection device. The detection device can include a lateral flow assay test strip that has been developed with the proper chemistry to detect the desired contamination in the surface sample and an assay reader configured with instructions for imaging the assay, analyzing the images, and determining a concentration level of the contaminant. Some embodiments of the collection device can be "open," referring to the transfer of fluid from the collection device to the detection device without use of a liquid-tight transfer mechanism. For example, fluid can be squeezed, poured, or dripped from the collection device onto an assay test strip.

FIG. 1A illustrates an example of an open system contaminant collection device 100 and an open system detection device 145. In this example, detection device 145 is a test strip 145 that includes a lateral flow assay. The collection device 100 can include a container 130, a handle 120 with a swab 125, a removable top 115, and a removable cap 105. In some examples, components of the collection device 100 are packaged separately. For example, as will be described in greater detail below, the collection device 100 can include a first package and a second package. The first package includes a buffer-filled container 130 in sealed assembly with a removable top 115 and a removable cap 105. The second package includes a handle 120 and a swab 125 that has been pre-moistened with buffer fluid. The first package and the second package can be individually sealed (in some cases, hermetically sealed) and can be provided to the user in a kit described in greater detail below.

The container 130 can be liquid-tight when the container 130, removable top 115, and removable cap 105 are coupled together, and can contain buffer fluid. The removable top 115 and container 130 can include threads for coupling as illustrated, or can include other suitable fluid-tight coupling structures, for example a snap fit. The container 130 can include a stability foot 135 to keep it oriented upright when positioned on a flat surface. The cap 105 can be threaded or configured to securely snap to the nozzle 110 of the removable top 115. The removable top 115 can be removed to provide access to the interior 140 of the container 130, allowing a user to remove the handle 120 and swab 125 from the container 130 and/or insert the handle 120 and swab 125 into the container 130. The removable top 115 also allows a user to pour fluid from the container 130 onto a test surface. In other embodiments in which the user uses the container 130 with a pre-moistened swab 125, the user may not pour any fluid from the container 130, thereby maintaining a known volume of fluid in the container 130. This feature can be beneficial for accurate assessment of collected contaminant concentration.

Components of the collection device 100 can be provided in any suitable configuration, depending on the needs of the user and the particular sample collection context. Components of the collection device 100 are described herein with reference to an example kit in which a pre-moistened swab material 125 and a handle 120 are provided in a first sealed package, and a container 130 filled with buffer, a removable top 115, and a removable cap 105 are provided in a second sealed package. Features of the example kit described herein advantageously limit exposure of the user to hazardous contaminants that are potentially present on a test surface while also very precisely controlling factors that can affect the accuracy of detection results (and in particular concentration measurements). It will be understood, however, that other configurations are possible. Some configurations are suitable for sample collection contexts where the analyte of interest is not a hazardous contaminant. For example, swab material 125 may be provided within the body of the container 130 and removed by the user prior to sample collection. Buffer fluid may be included or not included within the body of the container 130. If buffer fluid is not provided within the body of the container 130, a user can add buffer to the container 130 prior to sample collection (before or after removing the swab material 125 from the body of the container 130). A handle 120 may be provided within the body of the container 130 (for example, already coupled to the pre-moistened swab material 125), or it can be provided separately. If the handle 120 is provided separately, the user can remove the swab material 125 from the container 130 and attach it to the handle 120 prior to sample collection.

Though not illustrated, the container 130 can contain a certain volume of a buffer solution which will help lift the contamination from the swab material, keep the contaminate stable until it is ready to be transferred to the test strip 145, and provide a fluid suitable for transferring the contaminant to the test strip and for cooperating with the capillary action of the test strip to carry the contaminant to reaction zone(s) on the test strip. Possible buffer solutions are described in more detail below.

The handle 120 can have a "T-shaped" cross section with the "top" of the T for use in securing the swab 125 and the "downwardly-extending" portion of the T used as a grip. The size of the handle 120 can be selected to minimize usage of material while still providing a sufficient handle size to prevent contact between the hand of the user and the test surface. Some embodiments of a test kit can include protective gloves to provide a safeguard in addition to the handle 120 for preventing contact between the test operator and the test surface and/or testing fluids. Even where a kit does not include gloves, users can be instructed to use protective gloves during sampling and/or handling of samples.

The swab 125 can be constructed from a special material having desired pickup efficiency and shedding efficiency for detecting trace amounts of contaminants. Examples of swab materials are discussed in more detail below. Though shown in exploded view to illustrate the various components, the swab 125 can be coupled to the handle 120, thereby providing the user with a mechanism to wipe a test surface without contacting the surface and buffer fluid. The swab 125 and handle 120 can be coupled, for example by ultrasonic welding to melt material of the handle 120 into portions of the swab material, a clamping mechanism built into the handle 120, by adhesive, or by any other suitable attachment mechanism. There may be one or multiple layers of swab material provided on the handle 120. The swab material may be attached to the handle 120 in a taut manner or may be loosely attached to the handle 120. The swab 125 can include two layers of fabric. In one advantageous embodiment described in detail below, the swab is attached to the handle 120 in a configuration where portions of the swab material that are not directly fastened to the handle 120 remain loose relative to the handle 120.

The interior 140 of the container 130 can be shaped to substantially conform to the outer dimensions of the coupled handle 120 and swab 125 in some embodiments so that the swab 125 and handle 120 can be securely fitted within the interior 140. In the illustrated example, the interior 140 has a "T-shaped" cross section that fits the profile of the handle 120 and swab 125. This shape of the container can minimize the volume of buffer fluid needed to submerse a given portion of the handle in the buffer fluid. It is also shaped to minimize the buffer fluid that can reside around the grip portion of the "T" of the handle, thereby ensuring that most of the buffer fluid will be in the portion of the interior 140 where the swab 125 is located. The shape of the interior 140 is designed such that most of the fluid volume will be around the swab 125 and the container/handle design may not allow the swab 125 to be compressed against the inside wall of the container 130, for example by providing additional space in the interior 140 around the swab 125.

In some embodiments, the length of the container interior 140 may be just long enough for the handle 120 to be fully enclosed in the interior 140, thus minimizing movement of the handle 120 when the container 130 is inverted. As such, as the container 130 is inverted the buffer fluid moves back and forth across the swab 125. In another embodiment, the container 130 can be up to two times longer than the handle 120. This allows the handle 120 to slide back and forth with the buffer fluid as the container 130 is inverted. This movement may aid in better flushing of the fluid through the swab 125.

In some embodiments the container 130 can contain a volume of buffer solution suitable for wetting a determined test area, for example corresponding to an area template or area instructions provided with the kit. A user can pour buffer solution from the container 130 onto the test surface and then wipe the test surface with swab 125. In some embodiments the buffer solution can be provided in a separate container. After being applied to the test surface, the buffer solution can be absorbed, together with any contaminants contained therein, by the material of the swab 125. As described herein, in some embodiments no buffer solution may be poured from the container 130, and instead the swab material 125 can be pre-moistened with the buffer solution (or a dilute version of the buffer solution).

In some embodiments the volume of buffer solution and swab 125 can be provided together within the container 130 before use so that swab 125 is pre-wetted with the volume sufficient for wetting the test area of the designated dimensions. In other embodiments the swab 125 can be provided separately in a sealed package to maintain its pre-moistened state. A user can remove the swab 125 and handle 120 and wet the test surface by wiping the swab 125 across the test surface, such as by applying pressure to release the buffer solution from the pre-wetted swab 125. The user can in some embodiments perform additional wiping of the test surface with the swab 125 after release of the buffer solution, for example until most or all of the buffer solution is re-absorbed into the swab 125.

After completing wiping of the test area of the test surface, the user can insert the handle 120 and swab 125 into the container 130 and couple the removable top 115 and removable cap 105 with the container 130 to enclose the buffer fluid within the fluid-tight interior 140. The user can agitate the swab 125 within the sealed container 130 to shed collected particles from the swab material into the buffer solution. To transfer fluid from the interior 140 to the test strip 145, the user can remove the cap 105 and expel fluid through the nozzle 110, for example by inverting the container 130 and allowing fluid to drip through nozzle 110. The nozzle 110 can be sized and shaped for controlled release of a drop (or other volume) at a time of fluid onto the test strip 145. A drop is an approximated unit of measure of volume corresponding to the amount of liquid dispensed as one drop from a dropper or drip chamber via gravitational pull (sometimes aided by a positive pressure created within the container holding the liquid). Though the precise volume of any given drop depends upon factors such as the surface tension of the liquid of the drop, the strength of the gravitational field pulling on the drop, and the device and technique used to produce the drop, it is commonly considered to be a volume of 0.05 mL.

In some embodiments, the interior volume 140 of the container 130 can be reduced in order to dispense the fluid onto the test strip 145 for testing. This can be accomplished in several ways. In a first embodiment, the material of the container 130 is flexible enough to allow the user to squeeze the sides of the container 130 to expel controlled drops of fluid onto the test strip through the orifice of the nozzle 110. The flexibility can come from a combination of container wall thickness and material modulus optimized so that the entire container 130 can be squeezed. In a second embodiment, the container 130 can have thin sections in the container wall, running either axially or radially, that give the container 130 hinge points where it can flex while the rest of the wall is thicker and stiffer. The user can then squeeze the container 130 which flexes at the thin hinge points thus reducing the interior volume forcing the fluid out through the drip orifice without the entire wall being thin enough to flex. In a third embodiment, a portion of the cap 115 that contains the nozzle 110 drip orifice is flexible to allow a change in volume while leaving the container inflexible. The whole cap 115 or part of the cap may be made flexible. The flexible portion may only be a single section or spot that allows enough deflection to push a drop of fluid out when compressed or deflected. Other configurations to expel a drop or other volume of fluid from the container 130 through the nozzle 110 in a controlled manner are possible. In other embodiments, the container 130 may not require squeezing to dispense fluid from the container, and may dispense drops of fluid upon inversion with cap 105 removed.

Test strip 145 can include a sample receiving zone 150 and reaction zone 155. The user can transfer the fluid from container 130 to sample receiving zone 150, and the test strip can wick the fluid and any contaminants contained therein along the length of the test strip to and/or through the reaction zone 155. Reaction zone 155 can include one or more analyte binding regions. As illustrated, the actual capillary test strip can be housed within a cartridge with windows corresponding to the locations of the sample receiving zone 150 and reaction zone 155.

Figure 1B:
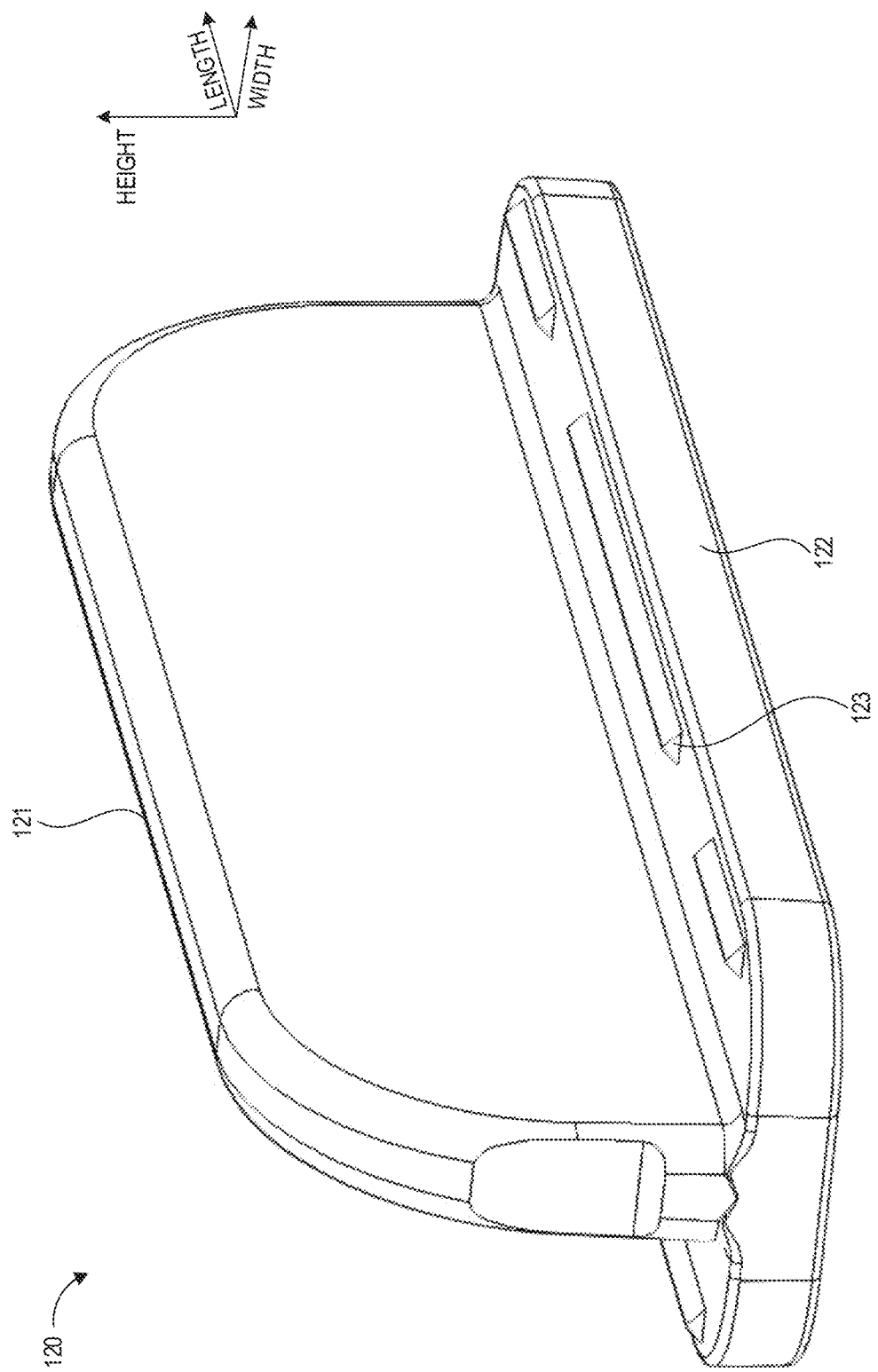
FIGS. 1B-1D illustrate various views of an example handle of the collection device of FIG. 1A.

FIG. 1B illustrates a perspective view of an example handle 120 of the collection device 100 of FIG. 1A. The handle 120 includes a base portion 122 for securing swab material (not illustrated in FIG. 1B) and a grip portion 121 extending from the base portion 122. The grip portion 121 and base portion 122 can be formed as a unitary structure, for example via injection molded plastic. The base portion 122 includes a first portion 122A adapted to fasten to the swab material and a second portion 122B adapted to support the swab material 125 as it contacts the test surface. The first portion 122A and the second portion 122B can be on opposite sides of the base portion 122 as in the illustrated implementation, but other configurations are possible.

Figure 1C:
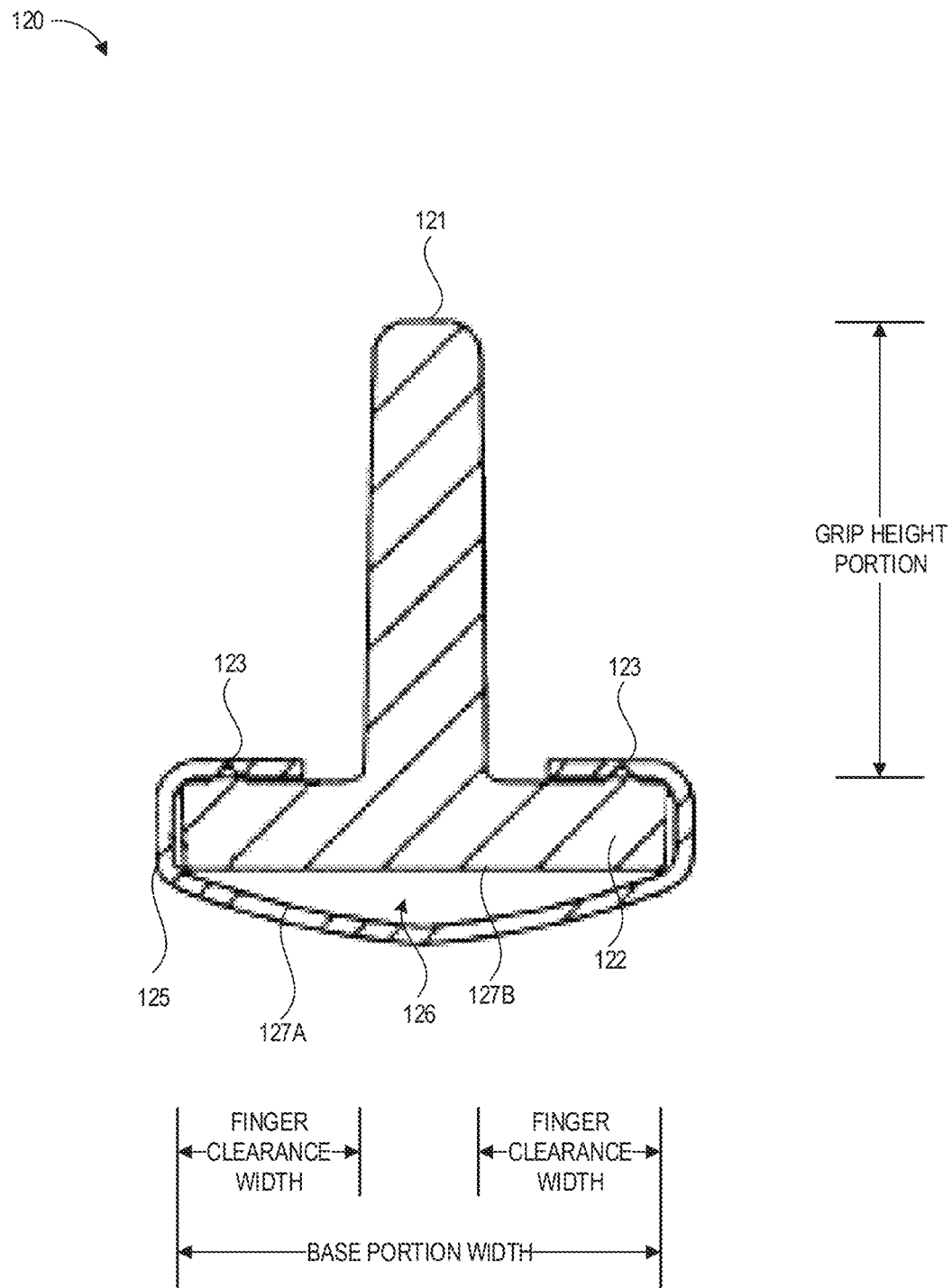

As illustrated, the grip portion 121 extends perpendicularly from the center of one face of the base portion 122. The grip portion 121 can extend away from the base at other angles and/or from other locations along the width of the base portion 122 in other embodiments. The grip portion 121 can have a height sufficient to keep the fingers of a user away from a surface in contact with the swab material secured to the base 122, for example 0.25 inches or more, or 0.5 inches or more, in various embodiments. In one non-limiting example, the height of the grip portion 121 is about 0.525 inches. The grip portion 121 can extend along the full length of the base portion 122 as illustrated, or can extend along just a portion of the length of the base portion 122. In some embodiments the width of the base portion can also assist in shielding the fingers of the user from the test surface, and the width can be for example 0.25 inches or more, or 0.5 inches or more, in various embodiments. In one non-limiting example, the width of the base portion 122 is about 0.55 inches. Embodiments of the base portion 122 with a width of about 0.55 inches can include about 0.2 inches clearance on each side of the grip portion 121 for the user's fingers to grip the handle 120. This can shield the user's fingers from the test surface below the base portion 122 during use of the handle 120, and can, for example, act as a stop to prevent the user's fingers from contacting the test surface. These example dimensions are illustrated in FIG. 1C for illustrative purposes only; other dimensions are possible and the handle 120 may not be drawn to scale. In some embodiments, the base portion 122 extends at least 0.1 inches beyond the user's finger on either side of the handle 120 when the user grips the handle 120.

The base portion 122 has a number of securing features 123 extending along at least a portion of the length of the base portion 122 from the same surface as the grip portion 121. As depicted, the securing features 123 can be a number of triangular prisms, for example two rows each having three axially-aligned triangular prisms. Other shapes, numbers, and configurations of the securing features are possible in other embodiments. FIGS. 1B and 1C depict the securing features 123 prior to attachment of the swab material. The swab material can be attached to these features 123 via ultrasonic welding in some embodiments. For example, the swab material can be positioned with a center portion along a face of the base portion 122 opposing the face with the securing features 123 with opposing edges of the swab material wrapped around the sides of the base portion 122 and positioned over the securing features. Ultrasonic energy can be applied to the securing features 123, causing the material of the features to melt or liquefy and flow into the fabric of the swab material. When the energy is removed the melted material solidifies, providing a mechanical attachment between the handle 120 and the swab material. Other mechanisms to attach the swab material to the base portion 122 are possible. In other embodiments the securing features 123 can be omitted and other mechanical fasteners (e.g., pins/screws) and/or adhesive can be used in place of the securing features.

Figure 1D:
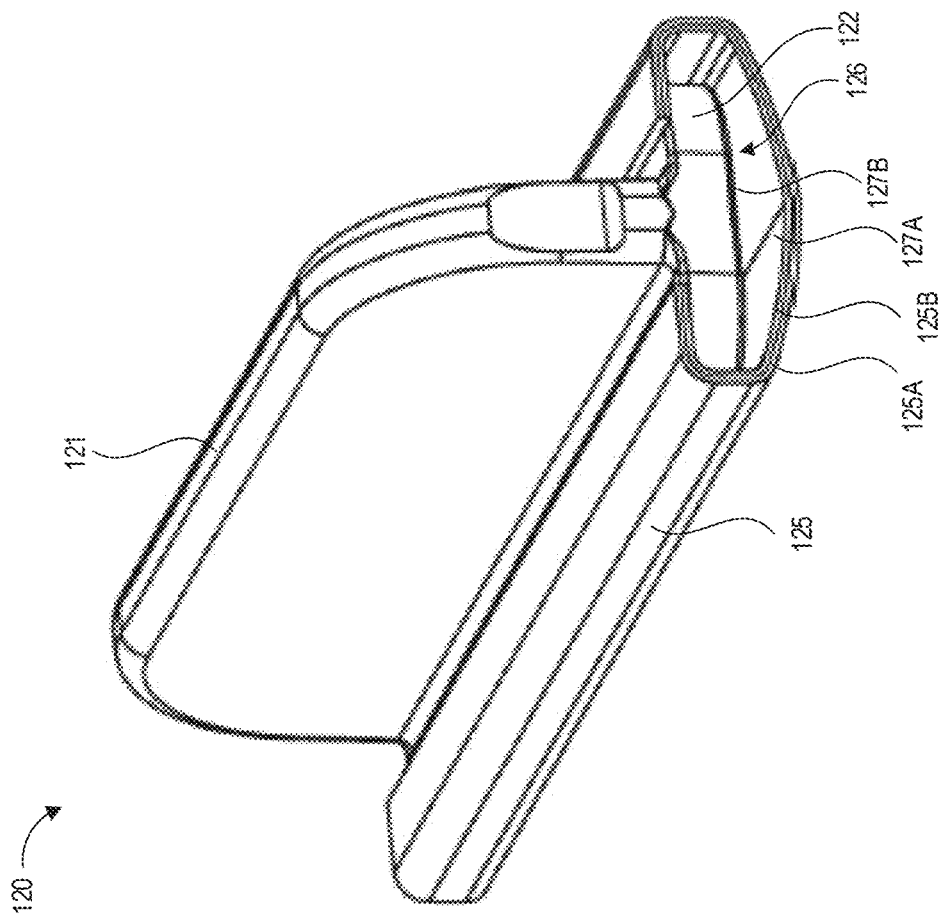

FIG. 1C depicts a cross-sectional view of the handle 120 having swab material 125 secured to the securing features 123 as described above, and FIG. 1D depicts a perspective view of the handle 120 and secured swab material 125. As depicted in FIG. 1D, in this non-limiting example the swab material 125 is formed from a material, for example woven polyester, folded or stacked into two layers 125A, 125B. The opposing edges of this dual-layer fabric are positioned over the securing features 123 (shown in cross-section FIG. 1C but obscured by the fabric in FIG. 1D) with the melted material of the securing features 123 solidified within the open space of the weave, thereby securing some of the woven fibers of the swab material 125 within the solidified securing feature material. Although FIG. 1C depicts the solidified securing features 123 in their original triangular configuration, due to the melting and solidification process other shapes are possible. Portions of the swab material 125 can be secured to first portion 122A of the base portion 122 of the handle 120 such that other portions of the swab material proximal to the second portion 122B of the base portion 122 remain loose relative to the handle 120. The swab material is configured to be loose enough to form a gap 126 between the surface 127A of the swab material 125 and the surface 127B of the second portion 122B of the base portion 122. The gap 126 can enable the swab material 125 to be agitated by buffer solution to extract collected contaminants from the swab material 125, and can be between 0.25 inches and 0.75 inches in some embodiments. The swab material 125 may be longer than the base 122 of the handle such that around 0.25 inches extends beyond the edges of the base 122. Other embodiments can use greater or fewer than two layers for the swab material 125, and can use separate pieces of fabric (for example, layered and then cut and sealed along the opposing edges that are wrapped over the securing features) or a single length of folded material.

Figure 1E:
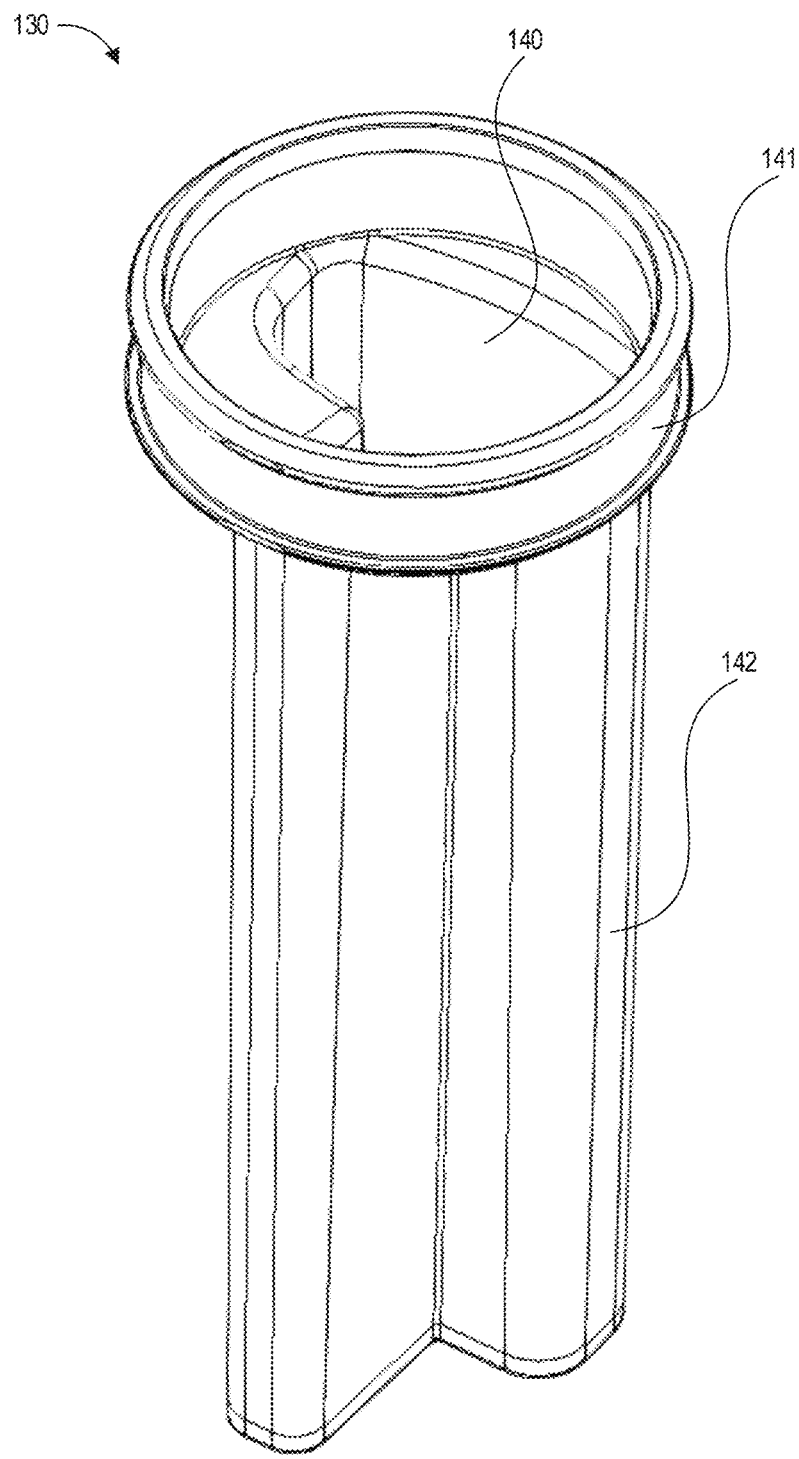
FIG. 1E illustrates an example collection container of the collection device of FIG. 1A.

FIG. 1E illustrates an example collection container 130 of the collection device of FIG. 1A. The collection container 130 has a circular upper rim 141 and a well wall 142 extending from the rim 141 and forming a well 140. The collection container 130 can be formed from an injection-molded plastic in some embodiments. The rim 141 can include a recessed portion between ridges for securing a retaining ring of a snap top as in the illustrated embodiment, with the ridges used to secure the snap top in place. In another embodiment, the rim 141 can be threaded in a corresponding manner with a threaded top. The well 140 can be formed with a T-shaped cross-section as illustrated to substantially match the shape of the handle 120. The well wall 142 can have uniform or substantially uniform (e.g., within acceptable manufacturing tolerances) walls in some embodiments such that the outer shape of the container 130 matches the cross-section of the well 140.

Figure 1F:
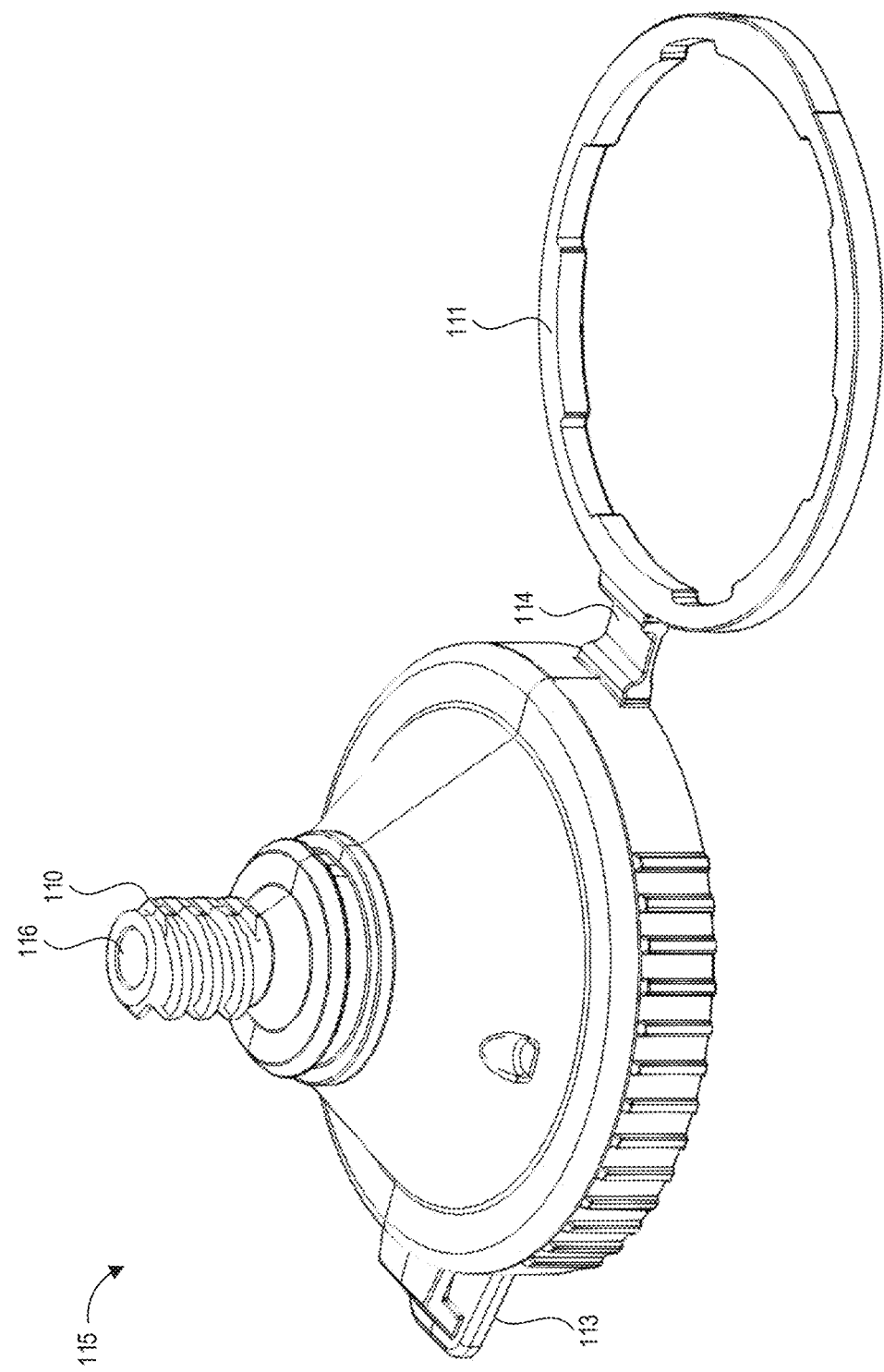

FIG. 1F illustrates a perspective view of the top of an example removable top 115 of the collection device of FIG. 1A, and FIG. 1G illustrates a cross-sectional side view of the removable top 115. The illustrated removable top 115 is configured to snap or press-fit onto the ridges of the upper rim 141 of the container 130. Other embodiments can include a threaded or other suitable connection rather than a snap or press-fit connection. For instance, the example collection device 100 described below with reference to FIG. 1H includes a threaded removable top 115 configured to engage a threaded container 130. Embodiments of collection devices 100 according to the present disclosure can advantageously create a fluid-tight seal between the removable top 115 and the container 130 with minimal user force and with the fewest number of components, thereby reducing risk that the user will not create a fluid-tight seal when the user engages the removable top 115 to the container 130.

The removable top 115 includes a frustoconical body with, a threaded nozzle 110 at the tip of the frustoconical body including fluid outlet channel 116, a tab 113 to assist a user in removing the top 115, and interior features including a cylindrical wall 117 and one or more detent(s) 118. The nozzle 110 need not be threaded and may interact with a removable cap 105 via a snap or press-fit connection, or any other suitable mechanism. The removable top includes a hinge 114 attaching a retaining ring 111 to the frustoconical body. Some embodiments can omit the tab 113, the retaining ring 111, and the hinge 114.

On the underside of the frustoconical body is the cylindrical wall 117 spaced apart from the detent(s) 118. The detent(s) 118 can include one or more protrusions extending from the inner rim of the top 115 towards the wall 117 or can be formed as a continuous annular feature. The cylindrical wall 117 includes a protrusion 119 that faces the detent(s) 118. Similar to the detent(s) 118, the protrusion 119 can include one or more protrusions or a continuous annular feature. The detent(s) 118 and cylindrical wall 117 are configured to secure the removable top 115 to the upper rim 141 of the container by positioning the upper rim 141 of the container 130 between the detent(s) 118 and the protrusion 119. For example, the protrusion 119 can be pressed into the inside of the mouth of the container opposite the rim 141 that extends around the exterior of the mouth of the container. This can seal the top 115 to the container 130. In one non-limiting example, the hoop strength of the cylindrical wall 117 and protrusion 119 combined with the deflection of the cylindrical wall 117 provides a normal force that seals the protrusion 119 to the inside wall of the container 130. The detent(s) 118 can secure to corresponding detents in the upper rim 141 of the container 130 to securely hold the top 115 onto the container 130, as well as to provide tactile and/or audible "click" feedback to the user to indicate that the top 115 is securely in place. Similar detents can be provided in a threaded embodiment of the top 115. Securing the top 115 to the container 130 beneficially prevents spillage of the buffer fluid, which potentially contains hazardous materials after the handle 120 is inserted into the container 130. Beneficially, embodiments of collection devices 100 described herein that include the wall 117, protrusion 119, and detent 118 can mitigate spillage of liquids from within the well 140 of the container 130 without the use of a separate sealing member or gasket. Accordingly, the collection devices 100 according to the present disclosure advantageously limit the number of total number of individual, separate components while also providing a fluid-tight seal, thereby limiting the risk of failure of components, the risk that components will not be aligned properly when assembled, and the risk that components will not operate as intended to create a fluid-tight seal. As one example, conventional collection devices that use sealing gaskets to create fluid-tight seals may fail if the gasket is cracked, torn, misaligned, or has even a minute defect or flaw due to chemical breakdown (which can occur with age) or faulty manufacturing. Embodiments of the collection device 100 advantageously mitigate these and other risks to minimize the potential that a user will be exposed to hazardous materials, including highly toxic contaminants that are extremely hazardous to human health even in minute amounts.

As shown in FIG. 1G, the inner aperture 116A of the channel 116 can be smaller than the outer aperture 116B of the channel 116. Accordingly, the channel 116 in this non-limiting embodiment is a tapered channel within the nozzle 110. The taper of the channel 116 can advantageously promote consistent drop sizes (consistent volume, consistent shape, etc.) for dripping fluid out of the well 140 through the nozzle 110, for example onto a test strip as shown in FIG. 1A.

Figure 1H:
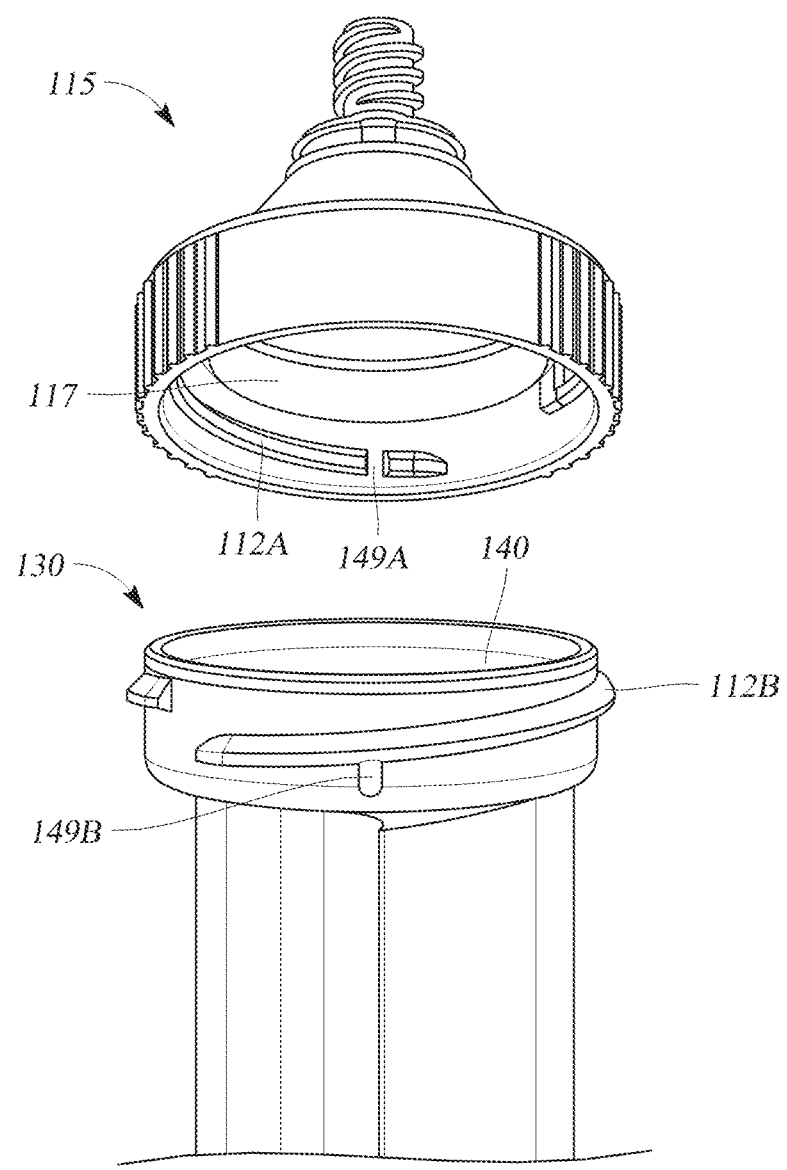
FIG. 1H illustrates an example of the detents discussed with respect to FIGS. 1F-1G in a threaded embodiment of an example removable top.

FIG. 1H illustrates an example collection device 100 in which the removable top 115 and the container 130 are coupled using a threaded engagement rather than a snap- or press-fit engagement. FIG. 1H also illustrates an example of the detents discussed with respect to FIGS. 1F-1G in a threaded embodiment of the removable top 115. The removable top 115 includes threads 112A positioned along the internal surface of its lower rim. The container 130 includes corresponding threads 112B positioned along the external surface of its upper rim. The threads 112A, 112B are configured to engage and mechanically mate with one another. The threads 112A of the removable top 115 have at least one gap 149A where the axial spiral of the threads 112A are interrupted and a negative space is formed. The container 130 includes a corresponding number of bump(s) 149B that align with the position of the gap 149A when the top 115 is screwed onto the container 130. The gap 149A and the bump 149B thus function as the detent described above to provide tactile and/or audible feedback to the user when the top 115 is correctly aligned with and fully threaded onto the container 130. In one example, the top 115 is provided with two gaps 149A on opposing sides of the threads 112A and the container 130 is provided with two corresponding bumps 149B. Thus, in some embodiments the described detent can be a combination of one or more gaps in the top threads that correspond with one or more bumps on the container to cause a snap or click when the top is fully screwed on.

Figure 1I:
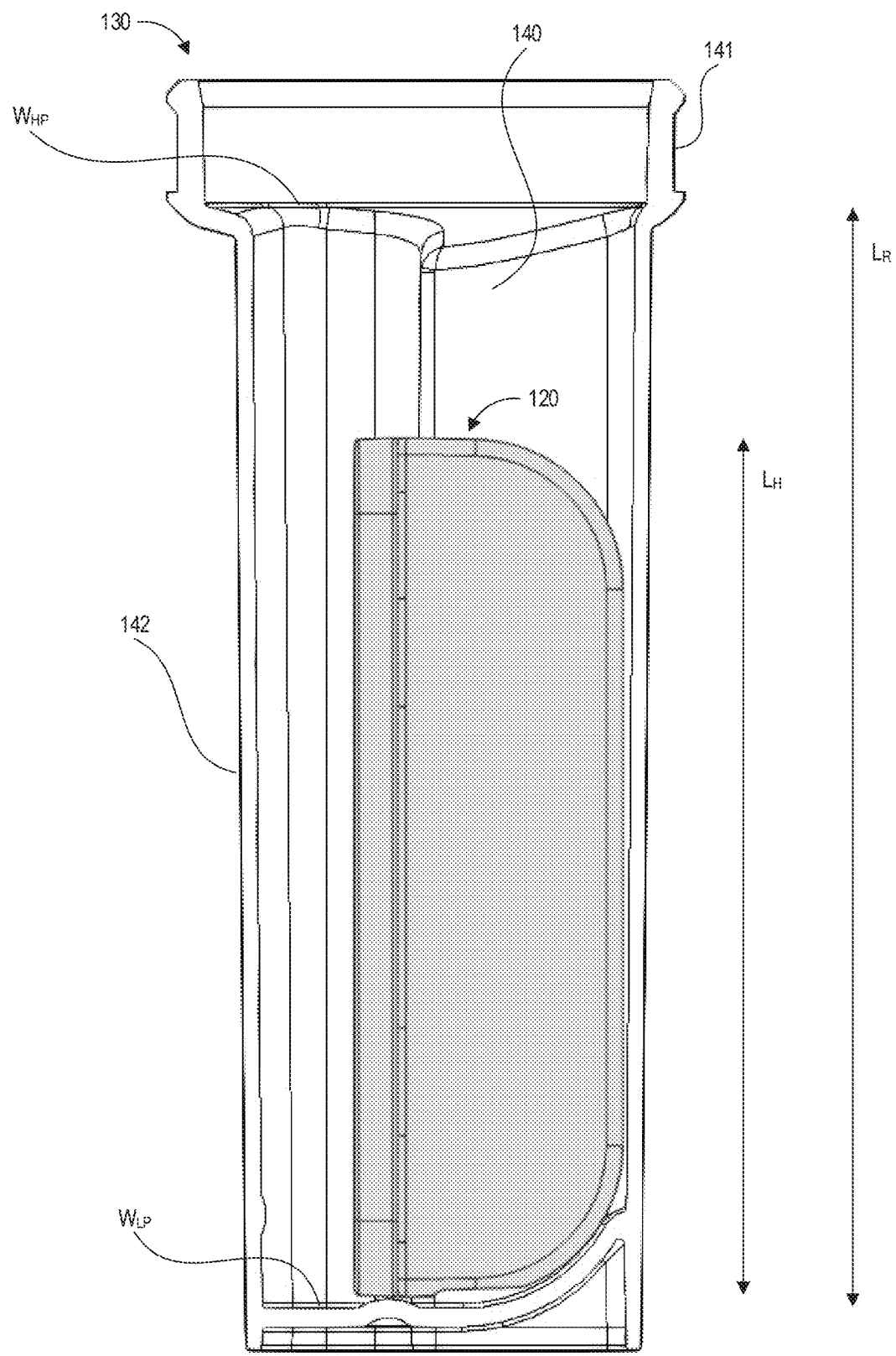
FIGS. 1I through 1K illustrate various views of the handle of FIGS. 1B-1D positioned within the collection container of FIG. 1E.

FIG. 1I illustrates a cutaway side view of the collection container 130 of FIG. 1E with the handle 120 of FIGS. 1B-1D positioned within the collection container 130. FIG. 1I shows the rim 141 forming a cylindrical opening leading into the T-shaped well 140. The handle 120 is depicted without the swab material attached in FIG. 1I. As illustrated, in this non-limiting embodiment the length $L_H$ of the handle 120 is less than the length $L_R$ of the interior of the well 140 that extends from the highest point of the well $W_{HP}$ to the lowest point of the well $W_{LP}$. In some embodiments, the difference between the length $L_H$ of the handle 120 and the length $L_R$ of the interior of the well 140 can be at least ⅛th inches, and preferably between ⅛th inches and ¼ inches. In one example implementation, the length $L_H$ of the handle 120 is 2 inches and the length $L_R$ of the interior of the well 140 is 2.25 inches. Providing a well with a greater length than the handle advantageously increases the amount of contaminant flushed from the surface of the swab material, for example when the user inverts container 130 and buffer fluid in the container 130 washes back and forth across the swab material to remove any picked-up contaminants. While the user inverts the container the handle 120 slides back and forth within the well 140 to provide for better washing of the fabric than in implementations having the same length for the handle and well.

Figure 1J:
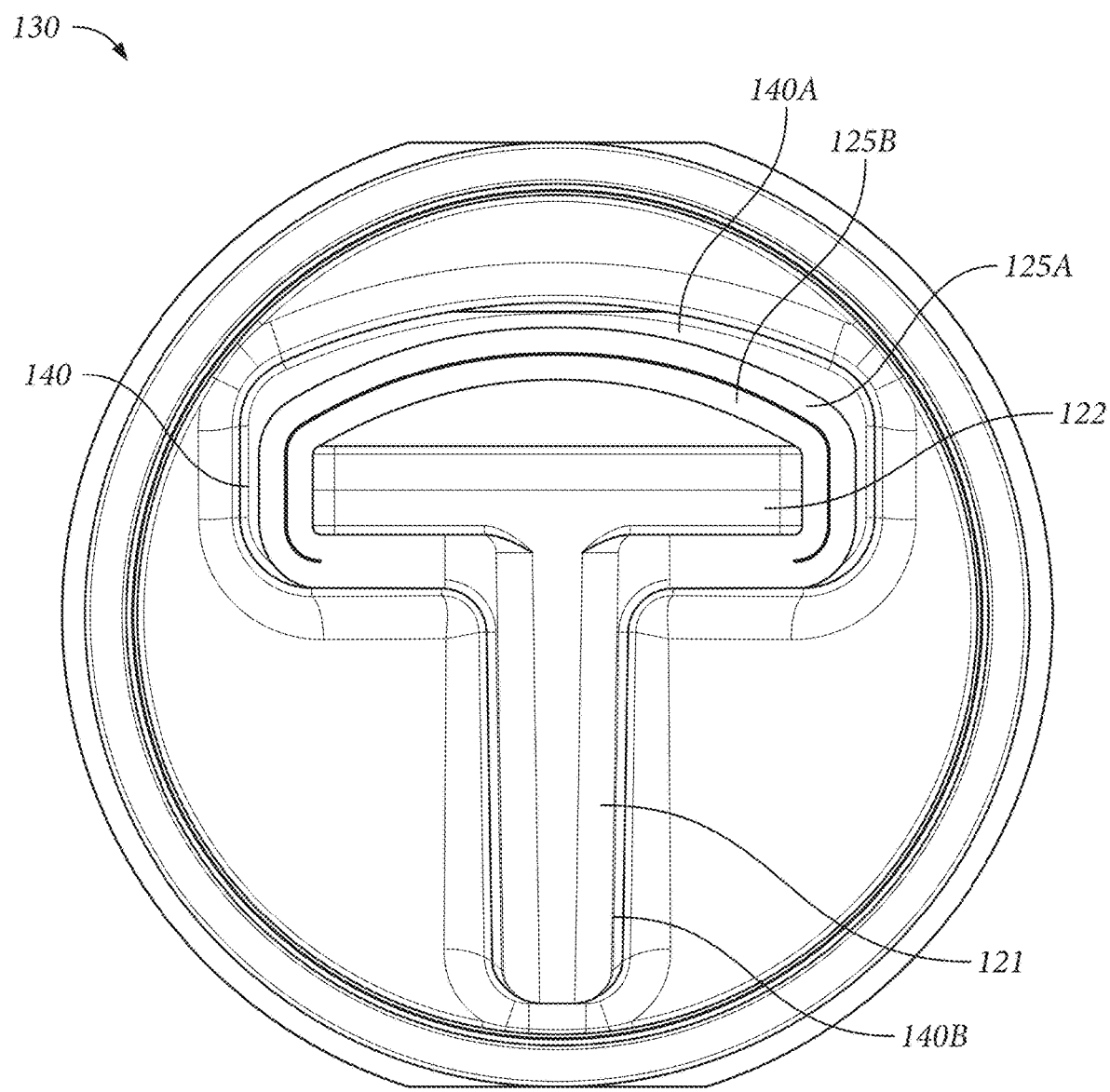

FIG. 1J illustrates a top view of the handle 120 positioned within the well 140, and depicts a representation of the swab material 125 (shown in two layers 125A, 125B) secured to the handle. As illustrated, the swab material 125 can be secured loosely to the base portion 122 of the handle 120 such that there can be a gap between the inner layer 125B of swab material and the surface of the base portion 122 facing the inner layer 125B. For example, the swab material 125 can be between 0.050 inches and 0.220 inches longer than the width of the handle. This results in portions of the fabric remaining loose relative to the surface 127B of the handle 120 and forming a gap 126 between the swab material and the handle 120 in which buffer fluid can freely flow, thereby allowing fluid to efficiently pass through and agitate the portion of the swab material that made direct contact with the test surface. The layers 125A, 125B can have the same or different widths across the width of the base portion 122.

The well 140 includes a first portion 140A sized to receive the base portion 122 of the handle 120 with the swab material 125, and the well further includes a second portion 140B sized to receive the grip portion 121 of the handle 120. In examples such as that illustrated in FIG. 1J, the second portion 140B is sized to snugly receive the grip portion 121 of the handle 120 (in other words, there is very little space between the second portion 140B and the grip portion 121 such that their surfaces are in constant contact or near constant contact). As illustrated, the second portion 140B has a substantially similar cross-section to the grip portion 121, where "substantially" refers to a cross-section of the second portion 140B being slightly larger to allow the grip portion 121 to slide into the second portion 140B. The cross-section of the first portion 140A corresponds to the cross-sectional area occupied by the base portion 122 of the handle 120 with the swab material 125 with a small gap to allow the swab material 125 to flow freely in the buffer solution in the well 140. Beneficially, providing the second portion 140B to have a similar interior volume to the volume occupied by the grip portion 121 causes the grip portion 121 to push most if not substantially all fluid in the well 140 out of the second portion 140B and into the first portion 140A when the handle 120 is inserted into the container. This can reduce the amount of buffer solution required to be placed in the well 140 in order to wash the desired amount of contaminants from the swab material 125, which beneficially increases the concentration of the contaminants in the solution compared to other embodiments that require greater amounts of buffer solution. The first portion 140A can be sized to substantially match the shape of the handle's base portion 122 with swab material attached, though the first portion 140A can (as illustrated) be slightly larger in order to facilitate agitation of the loose swab material during inversion of the container 130.

As such, the complementary shapes of the well 140 and handle 120 (including swab material 125) provide at least the following benefits: (1) minimizing unneeded "dead space" (e.g., space not occupied by handle 120 or swab material 125) inside the well 140 when the handle is inserted into the well 140, thus reducing the volume of buffer solution needed to extract contaminants from the swab material; and (2) maximizing concentration of the contaminant in the solution by promoting agitation of the material to extract the contaminant. Regarding unneeded "dead space" and the first portion 140A, a small amount of space is beneficial around the swab material 125 in order to allow the swab material to flow within the buffer solution and be agitated by turbulence during container inversions, thereby releasing the maximum quantity of collected contaminant from the swab material 125 into the solution. However, providing too much dead space creates a requirement for a greater amount of buffer solution to contact the swab material 125, thereby reducing the concentration of collected contaminant in the buffer solution. The complementary shapes of the well 140 and handle 120 thus enable accurate detection of even minute quantities of collected contaminants by maximizing both contaminant shedding from the swab material 125 and contaminant concentration in the buffer solution.

Although the sides of the grip portion 121 and second portion 140B of the well 140 are depicted as being straight, in other embodiments the sides of the grip portion 121 and the inner walls of the second portion 140B of the well 140 can be "keyed," that is, have corresponding features (e.g., curved or angled portions). Embodiments having a keyed grip portion 121 and second portion 140B beneficially can maintain the positioning of the grip portion 121 fully within the second portion 140B rather than allowing the base portion 122 to slide toward the far side of the first portion 140A of the well.

Figure 1K:
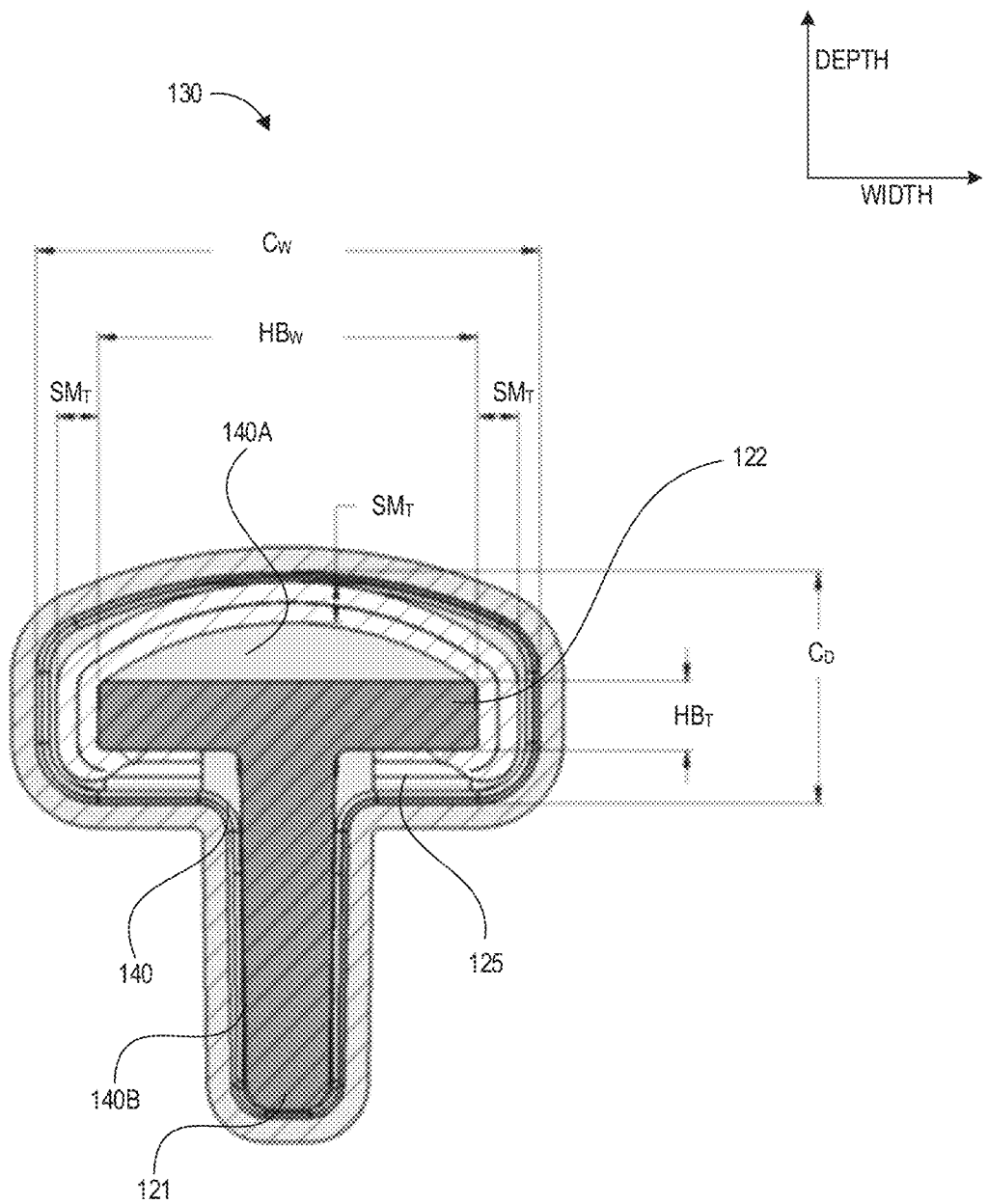

FIG. 1K illustrates example dimensions of portions of the handle 120, well 140, and swab material 125 in order to illustrate and not limit the described complementary shapes of the handle and the well. In one embodiment, the base portion 122 of the handle 120 has a width $HB_W$ of about 0.55 inches, the swab material 125 has a thickness $SM_T$ of about 0.06 inches and thus the combined width of the handle (between the base portion 122 and the four layers of swab material 125) is about 0.67 inches. The greatest width $C_W$ of the first portion 140A of the container well is about 0.73 inches at a highest point $W_{HP}$ (see FIG. 1I) along the height of the well. The width of the well can taper along the height of the well to be about 0.67-0.69 inches at a lowest point $W_{LP}$ (see FIG. 1I) of the well. Thus, the width $C_W$ of the first portion 140A can match or substantially match (e.g., at a smallest point along a tapered width) the total width of the handle base 122 and layers of swab material 125. In this embodiment, the platform of the base portion 122 of the handle 120 has a thickness $HB_T$ (with this thickness measured along the height of the handle) of about 0.1 inches and the two layers of swab material 125 positioned between the base 122 and the opposing wall of the well 140 have the thickness $SM_T$ of about 0.06 inches. The greatest depth CD of the first portion 140A of the container well is about 0.338 inches, which gives the 0.06 inches of swab material 125 about 0.238 inches (at the deepest point of the first portion 140A) through which the material can move loosely and freely during agitation. Buffer fluid can flow freely through this portion of the material, passing back and forth between the surface of the material that made direct contact with the test surface and the opposing surface of the material, thereby releasing analytes of interest captured in the material into the buffer fluid with greater efficiency and in greater numbers. As described above, in some embodiments the handle 120 and well 140 can be "keyed" by providing corresponding features along the cross-section of the second portion 140B of the well 140 and the grip portion 121. This keying can ensure that the relative positioning of the handle 120 along the depth of the well is maintained as shown with the grip portion 121 positioned fully back into the second portion 140B, causing all or substantially all fluid to be forced out of the second portion 140B of the well 140 by the grip portion 121 and maintaining the distance of 0.238 inches (at the deepest point) through which the buffer fluid can flow freely through the swab material 125.

Figure 1L:
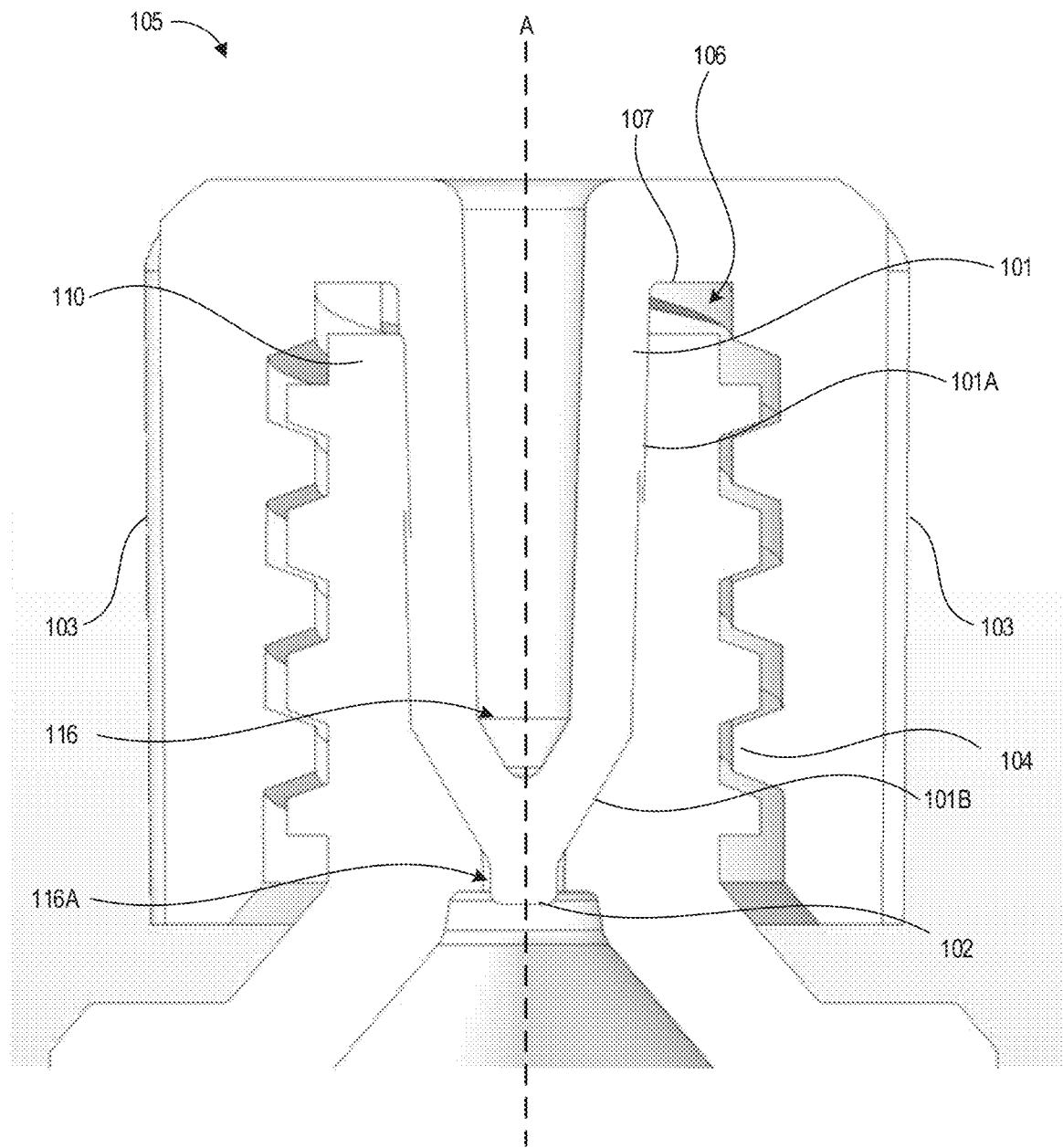
FIG. 1L illustrates a cross-sectional view of an example removable cap of the collection device of FIG. 1A.

FIG. 1L illustrates a cross-sectional view of an example removable cap 105 of the collection device of FIG. 1A secured onto the threaded nozzle 110 of the top 115. The cap 105 can include grip features 103 to facilitate a user turning the cap. As described above, the cap 105 need not be threaded and can interact with the top 115 using other suitable mechanisms, such as but not limited to a snap or press-fit mechanism. The removable cap 105 includes a cavity 106 lined with threads 104 for screwing onto the threaded nozzle 110 of the top 115. The cap 105 also includes a protrusion 101 extending into the cavity 106. The protrusion 101 is configured to plug the orifice 116 of the nozzle 110 of the top 115 with the upper wall 107 of the cavity sealing against the top surface of the nozzle 110. The protrusion 101 can be tapered to match the tapered contours of the channel 116. The protrusion 101 has at its lowest region (e.g., the region positioned furthest within the channel 116 when the cap 105 is screwed onto the nozzle 110) a post 102 that extends into the inner aperture 116A of the channel 116. This shaping of the cap 105 can serve to minimize any "dead space" in the channel 116 of the top 115 that could collect buffer solution in a manner that interferes with test result accuracy. For example, without the described features of the cap 105, buffer solution could collect within the channel 116 of the top 115 and stay in the channel 116 as the swab material 120 is agitated to release collected contaminants. This "trapped" buffer would be the first liquid to drip out of the container 130 due to its positioning in the channel 116, but it may not have mixed with the rest of the solution during agitation and thus would not contain any (or a great quantity of) collected contaminants. Additional features of the cap 105 according to the present disclosure advantageously avoid these potential issues. For example, the protrusion 101 of the cap 105 has an exterior shape that corresponds to the inner shape of the channel 116, thereby preventing buffer solution from accumulating within the channel 116 of the top 115. In one example, the protrusion 101 and the channel 116 have a first segment 101A angled at around 3.7° relative to a central axis A of the channel 116, with the first segment 101A forming a primary/largest sealing surface between the protrusion 101 and the channel 116. The first segment 101A can be followed by a second segment 101B angled at around 60° relative to the central axis A of the channel 116, where this second segment 101B acts as a stop to indicate to the user that the cap 105 has been fully threaded onto the nozzle 110. One or more detents may be included to facilitate providing such an indication to the user. The post 102 is sized to fill the inner aperture 116A of the top 115 without interference, and the post 102 and engaged surfaces of the second segment 101B cooperate to prevent fluid from entering the channel 116 when the cap 105 is fully screwed onto the nozzle 110 of the top 115.

FIG. 1M illustrates an example set 160 of the components of FIGS. 1A-1L that can be included in a collection device kit. The set 160 includes the container 130, top 115, cap 105, and handle 120 (including swab material). The kit can be packaged such that the container 130 is provided with a specified volume of buffer solution in the well and then sealed with the top 115 and the cap 105. The handle 120 can be packaged separately within the kit, and can be pre-moistened with a diluted version of the buffer solution within the container 130. FIG. 1L1M depicts a threaded version of the container 130 and top 115.

Figure 1N:
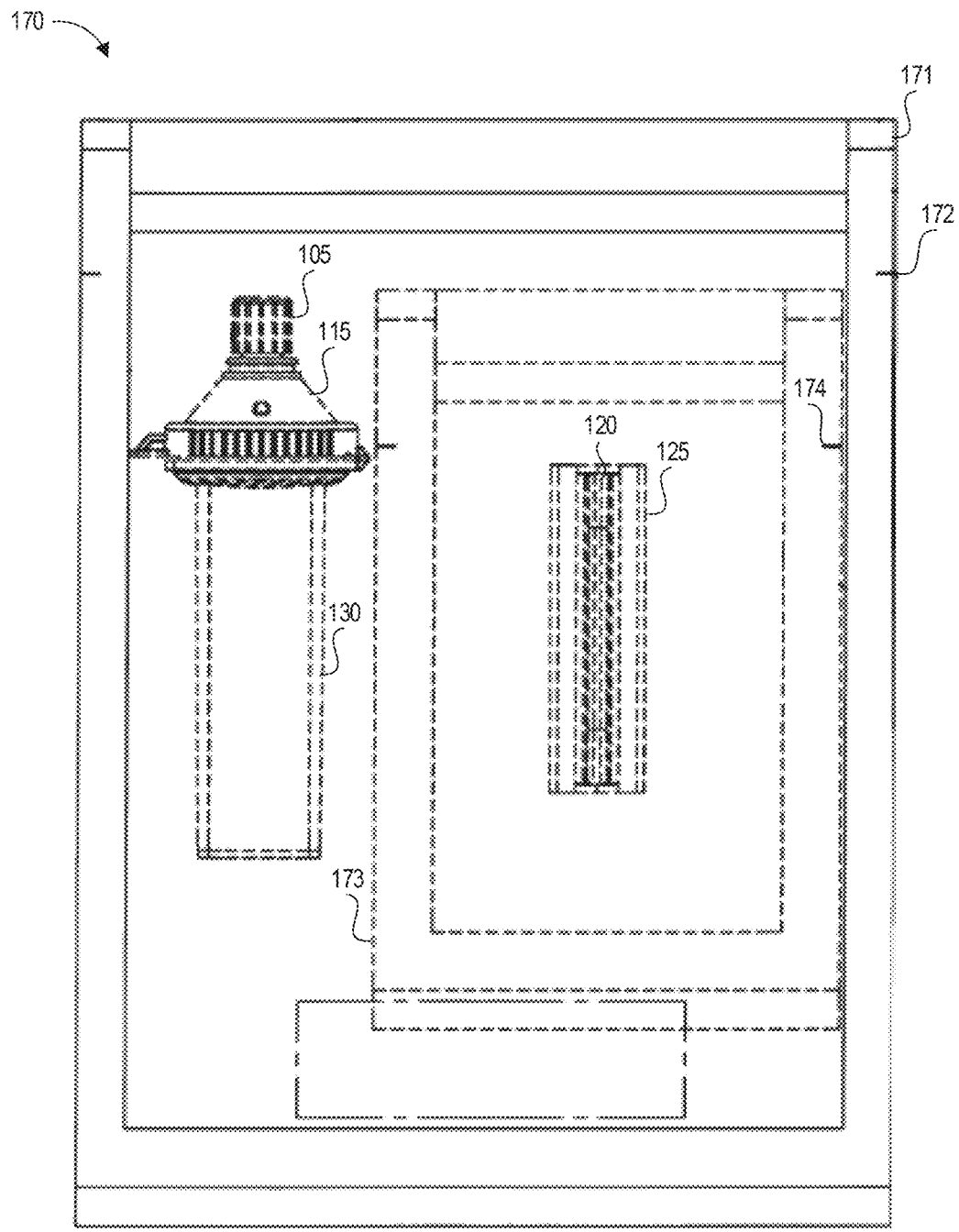
Figure 10:
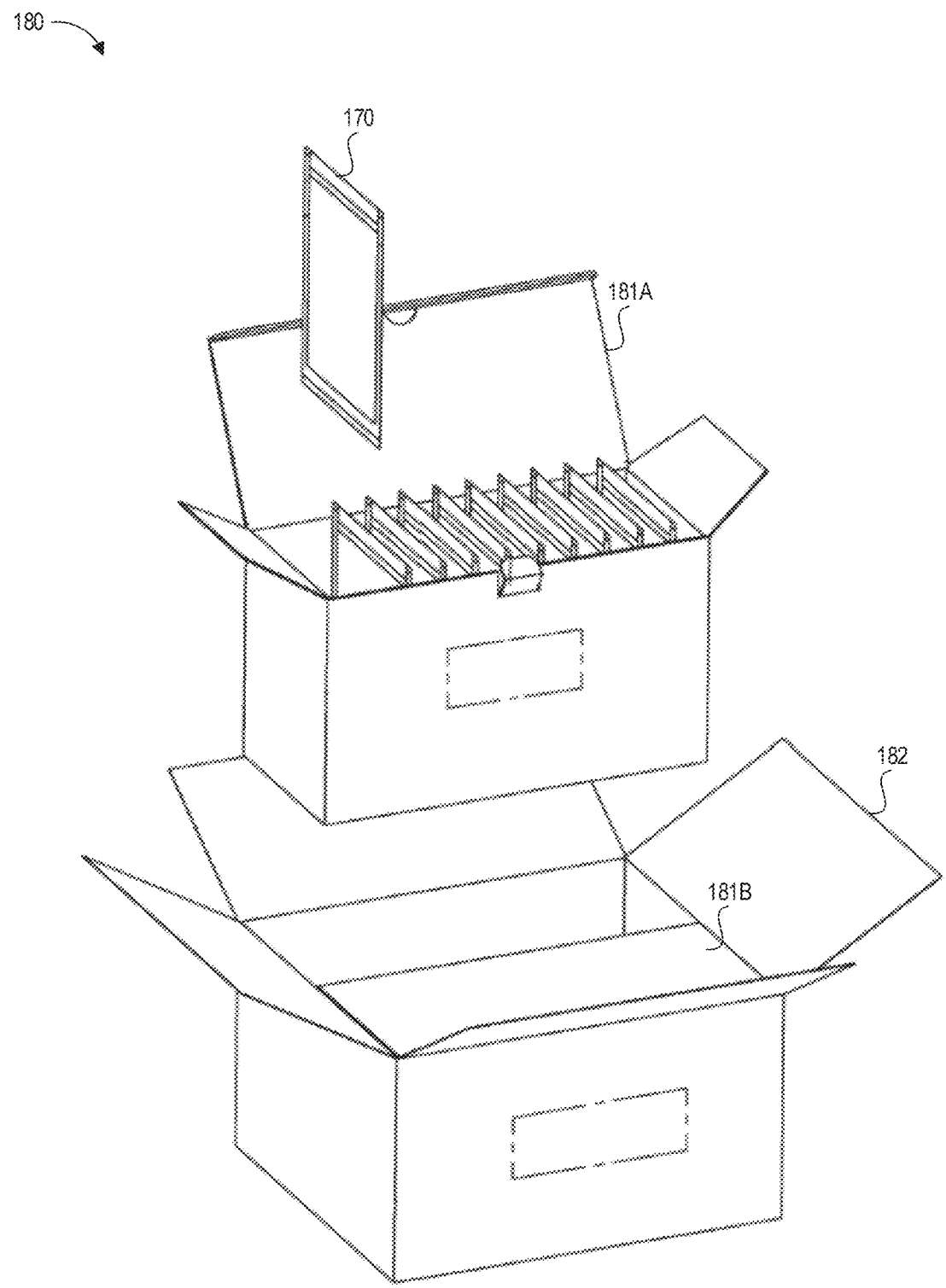
FIGS. 10A-10B illustrate another example of a contaminant collection device.

FIG. 1N illustrates an example collection kit 170 including the set 160 of components of FIG. 1M. The collection kit 170 includes a first container 171 that houses assembled container 130, top 115, and cap 105 (containing a volume of buffer solution as described herein) and also houses a second container 173. The first container 171 can be a heat-sealed polymer pouch with tear slits 172 in some embodiments. The second container 173 is a sealed enclosure housing the assembled and pre-moistened swab material 125 and handle 120. The second container 173 can be a heat-sealed polymer pouch with tear slits 174 in some embodiments. For example, the assembled swab material 125 and handle 120 can be placed on a portion of the film that forms the second container 173, sprayed or otherwise provided with a dilute version of the buffer fluid in the container 130, and then the second container 173 can be sealed around the moistened swab. The second container 173 can be a metalized polymer that includes a foil or metal in the material forming the pouch of the second container 173. Metalized polymer containers can advantageously maintain and preserve fluid, such as fluid that has been provided to the swab material 125, during shipping and storage.

In order to use the set 160 of components to perform wiping of a test surface as described herein, the user can open the first container 171 of the collection kit 170 and remove the container 130 with the top 115 and cap 105 attached and with the reagent and buffer solution already within the well of the container 130. The user can remove the second package 173 with the separately packaged handle 120 with the swab material pre-attached and pre-moistened with the dilute version of the fluid in the container 130, open the second package 173, and wipe the test surface with the pre-moistened swab material. The user can remove the top 115 from the container 130 to provide access to the well 140. After completing the wiping of the test surface, the user can slide the handle 120 into the well 140 of the container 130, close the top 115 onto the container 130, and invert the container 130 (e.g., flip it 180 degrees) a number of times, for example 5 or more times. As discussed above, inverting the container 130 washes the swab material with the buffer solution and extracts any contaminants picked up from the test surface. After completing the recommended number of inversions of container 130, the user can remove the cap 105 and drip the buffer solution (and any contained contaminant particles) onto a test strip through the orifice 116.

FIG. 1O illustrates an example package 180 that includes a number of collection kits 170. The package 180 includes two shelf boxes 181A, 182B that each can house, for example, ten collection kits 170. The shelf boxes 181A, 182B are provided within a larger shipping container 182. Optionally, the shipping container 182 can also include templates to demarcate the test surface and assist the user during sample collection, assay test strips, and/or assay reader devices as described herein.

Figure 1P:
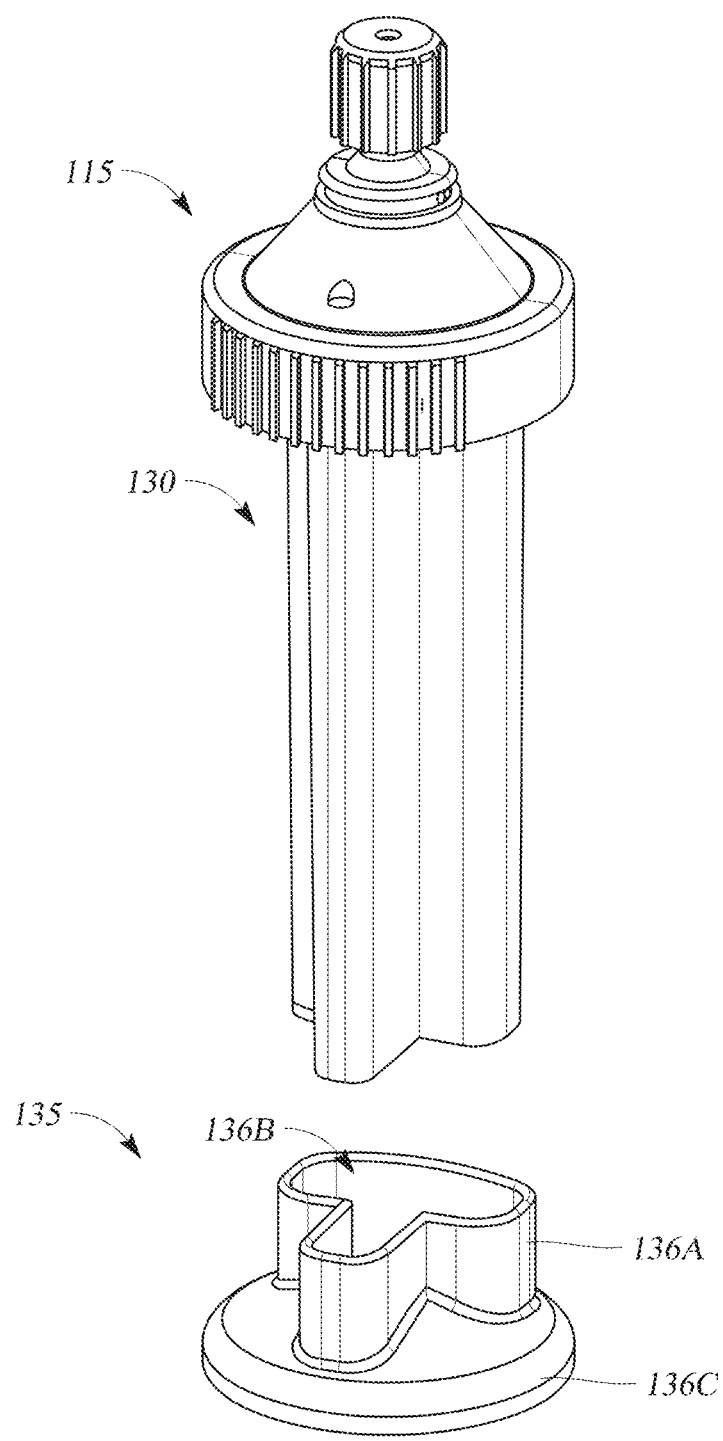
FIG. 1P illustrates an example stability foot that can be used with the collection container of FIG. 1E.

FIG. 1P illustrates an example stability foot 135 that can be used with the collection container of FIG. 1E. In FIG. 1A, the stability foot 135 is shown as integrated into the collection container 130. However, in other embodiments the collection container 130 can be formed separately from the stability foot 135, as shown in FIG. 1P. The stability foot 135 can include a T-shaped wall 136A defining a T-shaped aperture 136B sized to snugly receive the bottom of the container 130, with the T-shaped wall 136A extending upwardly from a wider base portion 136C. The base portion 136C can contact a surface on which the container 130 is set and provide stability so that the container 130 is not as easily tipped. The bottom of the container 130 can be press fit into the aperture 136B, or it can have snap features such as a bump on the container that fits into a recess on the interior of the T-shaped wall 136A (or vice-versa) to provide the user with tactile and/or audible feedback of the container 130 being positioned correctly within the stability foot 135.

Figure 2:
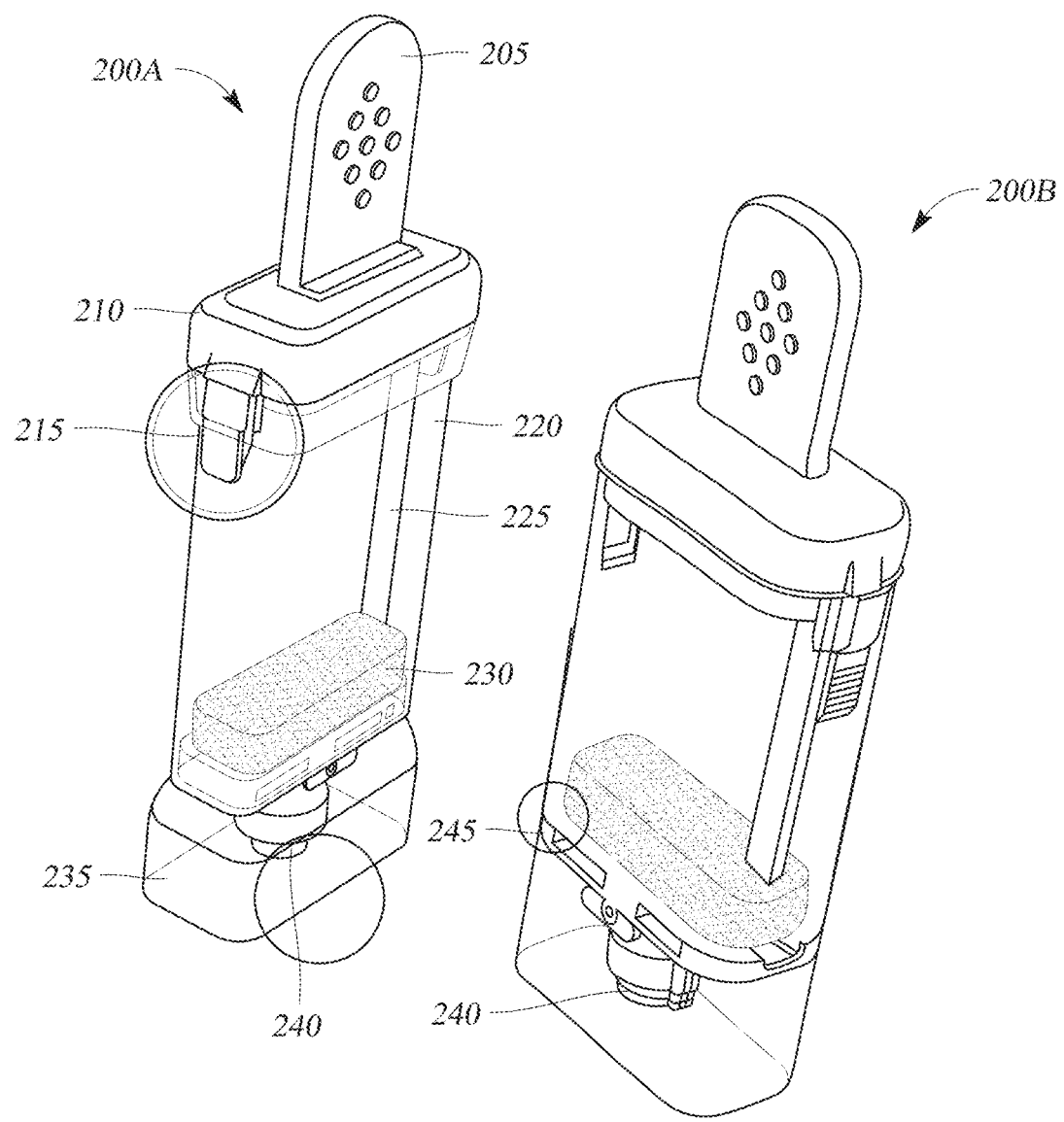
FIG. 2 illustrates another example of an open system contaminant collection device.

FIG. 2 illustrates perspective views of another example of an open system contaminant collection device, with two such devices 200A, 200B shown. Each device 200A, 200B can include a swab 230 and a container 220 for sealing the swab 230 after collection of contaminant particles.

The swab 230 can be constructed from a material having desired pickup efficiency and shedding efficiency for detecting trace amounts of contaminants, for example antineoplastic agents. Examples of swab materials are discussed in more detail below. The swab 230 is provided on a handle 225 having sufficient length so that the user can swab a surface without physically contacting the surface or the swab 230. The swab 230 can be pivotably coupled to the handle 225 in some embodiments. The handle 225 can be coupled to or part of a cap 210 in some embodiments. As such, cap 210 can include a portion 205 extending from the body of the cap 210 for grasping by a user.

A liquid, for example a buffer solution, can be provided within the container 220 so that the user removes a pre-wetted swab to wipe the surface (and optionally pours additional fluid onto the surface from the container 220) in one implementation. In another implementation, the user can spray the surface with a liquid and collects this liquid with the swab.

After swabbing the surface, the user places the swab 230 into the container 220 and the cap 210 forms a liquid-tight seal when engaged with the container 220. The cap 210 can additionally lock to the container. As illustrated, cap 210 can include one or more tabs 215 that securely couple the cap 210 to the container 220 to provide a fluid-tight enclosure within the container 220. The tabs 215 can releasably engage corresponding features of the container 220 to both provide the fluid-tight seal and allow for removal and use as the handle of the swab 230. A base 235 of the container 220 can be shaped to allow the container 220 to stand upright on a surface, further preventing fluid spillage from container 220. The lower interior portion of the container 220 can include steps 245, wedges, or other structures along its interior to squeeze fluid from the swab 230 when inserted fully into the container 220. Thus, the length of handle 225 can be selected to force swab 230 onto the steps 245 when the cap 210 is coupled to the container 220.

The container 220 advantageously prevents liquid from spilling and contaminating surfaces or users, but provides for controlled release of fluid to a detection system. The detection system can be an immunoassay, for example a lateral flow assay, with an interface that alerts the user to the presence and/or degrees of contamination. Controlled release of the fluid can be provided through a release mechanism, such as valve 240. Valve 240 can be a one-way valve in some embodiments. In some embodiments, the body of the container 220 can be flexible to allow a user to squeeze fluid through the valve 240. In some embodiments, the base 235 of container 220 can be flexible to allow a user to squeeze the valve 240 open to allow fluid to drop through while keeping the hands of the user away from the fluid. In other embodiments the valve 240 can be incorporated into a coupling mechanism for coupling to a closed system detection device and the collection device 200A, 200B can be a closed system contaminant collection device as discussed in more detail below.

In some embodiments, a user can shake or otherwise agitate the collection devices shown in FIGS. 1A-2 prior to transferring the fluid to a detection device to release collected contaminants from the swab 125, 230 into the buffer fluid in the container. For example, the container can be inverted a number of times to allow the buffer fluid to flow back and forth across the material of the swab. The buffer fluid can have properties that assist in releasing collected contaminants from the swab material in some implementations, as discussed in more detail below. As such, the flow of the buffer fluid can extract the contamination from the material of the swab and mix it into a homogeneous solution for testing.

Figure 3A:
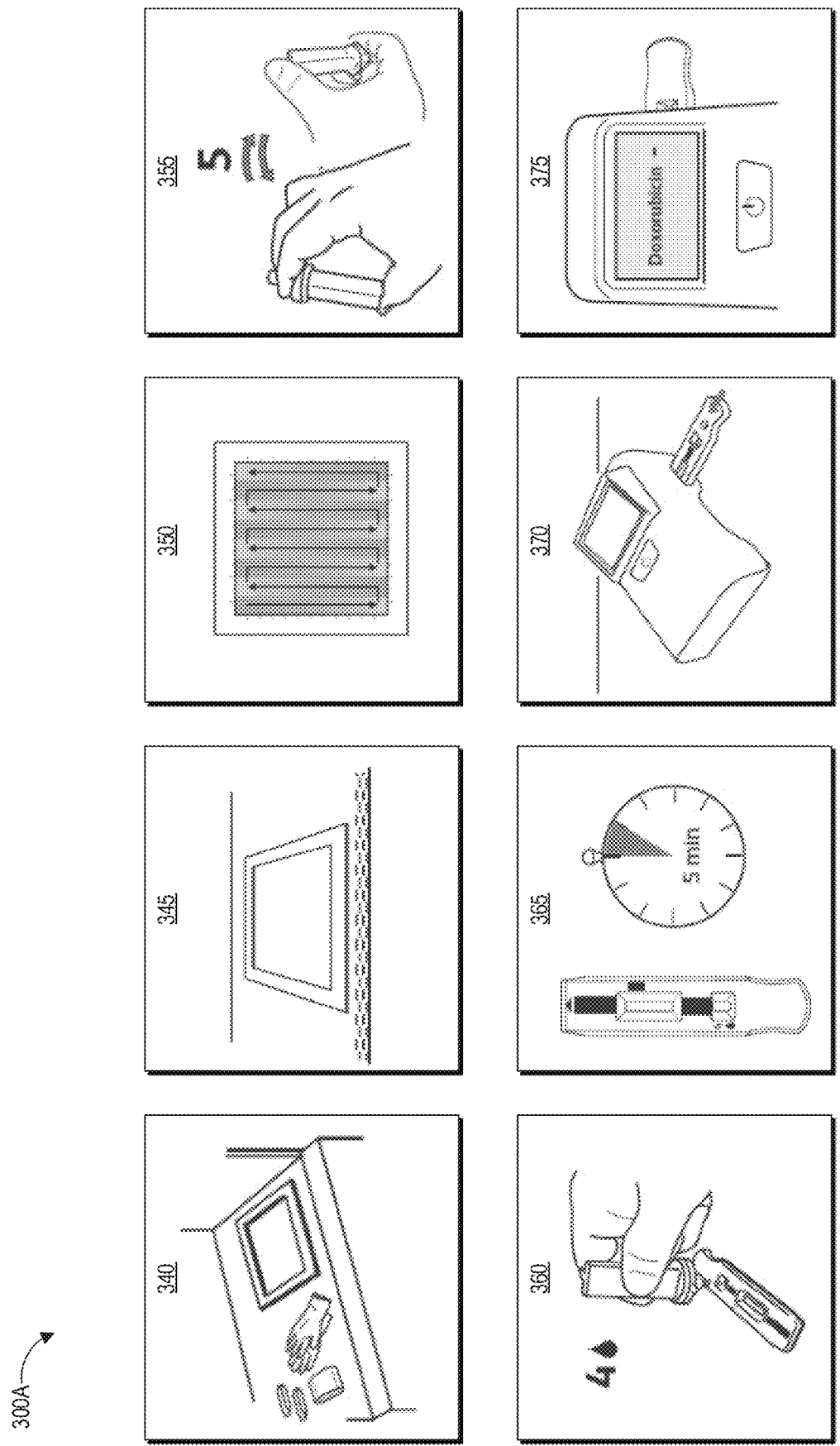
FIGS. 3A and 3B illustrates example steps of a testing method using an open system contaminant collection device.

FIG. 3A illustrates example steps of a testing method 300A using an open system contaminant collection device, such as but not limited to those shown in FIGS. 1A-2. One, some, or all of the depicted blocks of FIG. 3A can be printed as graphical user interface instructions on the packaging of an assay and/or collection kit, for example the packaging shown in FIGS. 1N and 1O, or can be presented on a display screen of an assay reader device, a test area terminal, or a personal computing device of the user.

At block 340, the user can identify a sample location and gather a collection kit, assay cartridges, and a template. The collection kit can be the kit 170 described above and can include container 130, top 115, and cap 105 assembled and containing buffer solution, and can include a sealed package with handle 120 and pre-moistened swab material 125. The collection kit can include a swab attached to a handle and a collection container. In some examples, the swab is pre-wetted with buffer solution and packaged together with the handle in a first sealed pouch and the collection container is packaged in a second sealed pouch. The assay cartridge may include an assay device housed inside a cartridge having a window or port aligned with a sample receiving zone of the assay device. In one implementation, the assay device is a test strip, for example but not limited to a lateral flow assay test strip. Also at block 340 the user can put on clean gloves prior to each sample collection and/or opening of the collection kit, both to protect the user from potential contamination on the surface and to protect the collected sample from contamination on the user's hands.

At block 345, the user can establish a test area on the test surface. For example, the user can place a template (physical or augmented reality) over the intended location to clearly demarcate the area that will be swabbed. Also at block 345 the user can open the collection kit packaging, including opening the separately-packaged swab and handle. The test area may be one square foot in some embodiments, for example demarcated as a 12 inches by 12 inches (144 square inches) region. Other examples can use greater or smaller areas for collection including 10 inches by 10 inches, 8 inches by 8 inches, 6 inches by 6 inches and 4 inches by 4 inches, non-square rectangular regions (e.g., a 9 inches by 16 inches rectangle), and non-rectangular regions (e.g. circles). Different-sized templates may be specified for usage with different test surfaces. The particular template used can be indicated to a reader device, for example via a manual user input or via a barcode or other identifying pattern on the template scanned by the reader device. For example, a template providing a swab area of a 12 inches by 12 inches region can be indicated for use in sampling a countertop, while a smaller template demarcating a smaller swab area can be indicated for swabbing an IV pole. The reader device can adjust its test result calculations to account for the actual area tested, as indicated by the particular template used for the sampling procedure.

At block 350, the user can swab the entire test area with the pre-moistened swab. The user can swab the test area using slow and firm strokes. As shown, the user can methodically pass the swab in straight lines along the height of the test area all the way across the width of the test area.

At block 355, the user can insert the swab into the collection container. In some examples, the collection container includes a t-shaped well. Though not illustrated, the swab may have a t-shaped cross-section that substantially matches that of the container well. The user seals the container with a top that includes a dripper cap, and fully inverts (e.g., turn upside down and then return to right-side-up) the sealed container five times. During these inversions, the liquid in the well of the container washes primarily over the swab material due to the cross-sectional shape and other features of the well, and the handle slides within the well due to the well having a greater height than the handle. As described herein, the inversion combined with the geometries of the container and handle and the flow of the buffer solution can extract collected contaminants from the swab material. In one non-limiting example, the user does not invert or agitate the container before moving to the next step.

At block 360, the user can leave the swab and handle inside the container, remove the dripper cap, and squeeze (or allow gravity to draw) one or more drops (for example but not limited to four drops) into the sample well on one or more assay cartridges. For example, in some embodiments the user may drop sample onto multiple assays each designed to test for a different drug. In some examples anywhere between three and ten drops can produce suitable results on the assay. In alternate embodiments the user may mechanically couple a fluid transfer portion of the collection device to a fluid transfer portion of the assay device to release a controlled volume of sample through a closed fluid pathway, for example as shown in FIG. 5C.

At block 365, the user can use a timer to allow the sample to develop for a period of time. For example, the sample can develop for about one minute, about two minutes, about three minutes, about four minutes, about five minutes, about six minutes, or some other amount of time. Other development times are possible. In some embodiments the timer can be built in to the programming of the reader device that reads the assay. The development time can vary depending on the particular test that is being performed and the particular operating parameters of the assay device.

At block 370, the user can insert the assay cartridge into an assay reader device. The assay cartridge can be inserted into the ready device prior to or after the sample is developed, depending upon the operational mode of the device. In some embodiments, the user may sequentially insert multiple cartridges for testing different aspects of the sample or for ensuring repeatability of test results.

At block 375, the assay reader device reads portions of the inserted cartridge (including, for example, detecting optical signals from exposed areas of a capture zone of a test strip housed in the cartridge), analyzes the signals to determine optical changes to test zone location(s) and optionally control zone location(s), determines a result based on the optical changes, and displays the result to the user. The device can optionally store the result or transmit the result over a network to a centralized data repository. As illustrated, the device displays a negative result for the presence of Doxorubicin in the sample. In other embodiments the device can display a specific detected concentration level in the sample and/or determined for the test area, and optionally can display confidence values in the determined result.

After testing the user can re-seal the container with the dripper cap and dispose of the collection device and assay (for example in compliance with hazardous waste regulations). Optionally, the user can reconnect the reader device to its power supply, execute any needed decontamination procedures, re-test a decontaminated surface, and perform required reporting of the result.

Figure 3B:
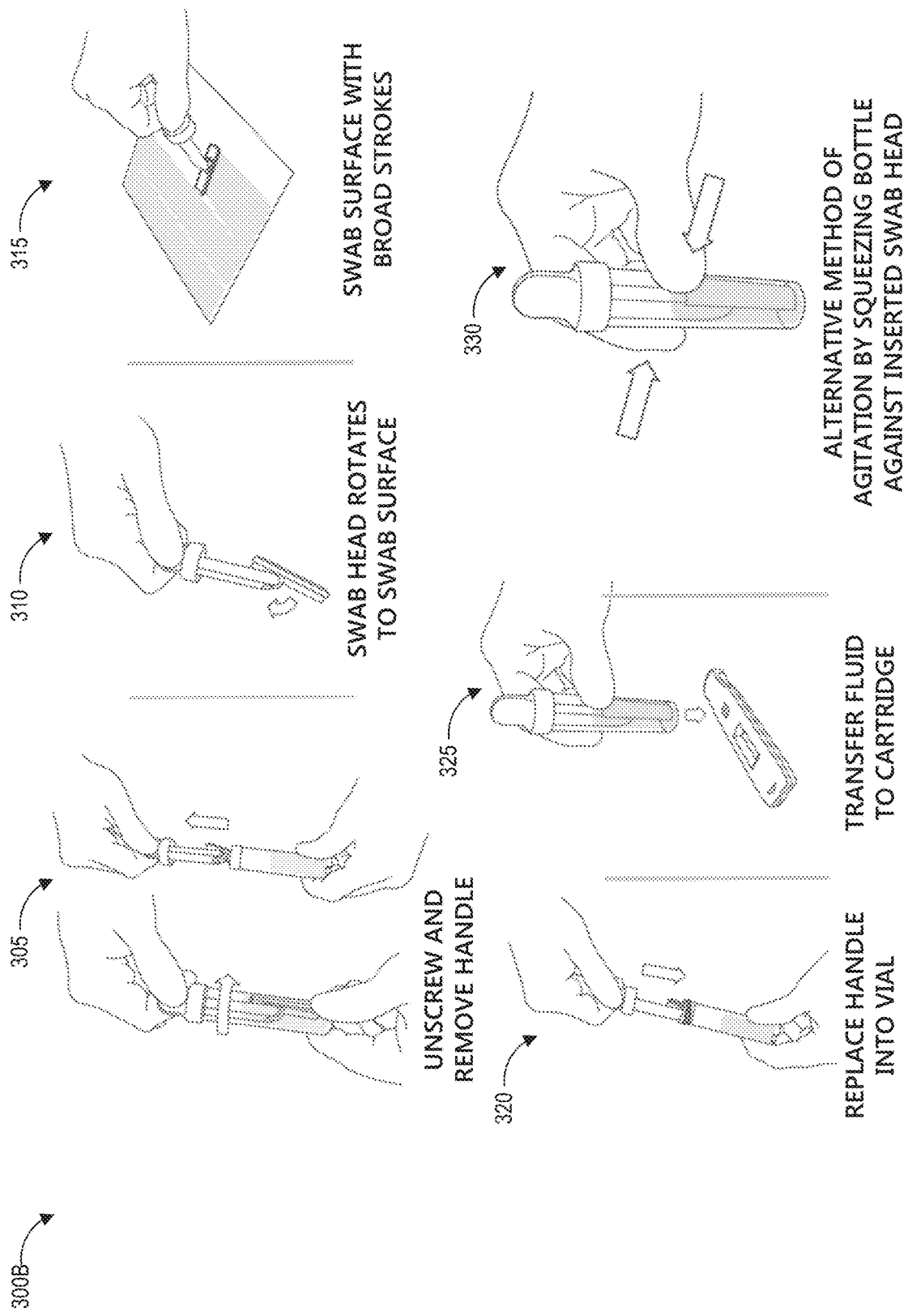

FIG. 3B illustrates another testing method 300B that depicts details of steps 350, 355, and 360 of the process 300A using an alternate embodiment of the collection device.

At step 305 the user can remove the handle and swab from the container. As described above, the swab can be pre-wetted for wetting the test surface with a buffer fluid that helps lift contaminants from the test surface into the swab and/or the user can separately apply fluid to the test surface.

At step 310, optionally in some embodiments the swab head can rotate to assist in maintaining contact between the swab and the test surface.

At step 315, the user can swab a designated test area of the test surface. It can be preferable in some implementations to swab the entirety of the test area and only within the test area so as to generate an accurate measurement of the concentration of the contaminant, particularly for contaminants where small quantities per area are harmful to users. Swabbing the entirety of the test area and only within the test area can also generate an accurate measurement of the concentration of the contaminant in situations where a very small amount of contaminant is present. Even if the amount of contaminant detected is very small and not immediately harmful to persons in the immediate area, detection of contaminant in any amount can alert the user to a leak or unintended release of hazardous material. As such, some embodiments can include placing a guide or template over the test area to assist the user with swabbing only the test area.

At step 320, the user can replace the swab and handle into the collection container. Optionally, the user and/or structure of the container can agitate the swab to release collected contaminants into the fluid within container. For example, step 330 shows the user squeezing the sides of the container against the swab head.

At step 325, the user can transfer fluid to a cartridge containing a test strip, or to another test device. For example, the user can drip fluid from the container onto a sample receiving zone.

Though not illustrated, further steps can include inserting the cartridge into a reader device, operating the reader device to perform analyze the test strip, and viewing results of the test.

Overview of Example Closed System Contaminant Collection Devices

Some embodiments of the contaminant collection device can be "closed," referring to the transfer of fluid from the collection device to the detection device via a liquid-tight transfer mechanism. For example, the collection device and detection device (such as a test strip or cartridge holding the test strip) can be structured to couple together to provide a fluid tight seal between the liquid-containing portion of the collection device and the test strip so that harmful fluids, drugs, or vapors are completely contained and not vented into the atmosphere and possibly creating additional harm to the user. Fluid-tight can refer to being liquid impermeable, gas or vapor impermeable, or both, depending upon the properties of the contaminant that the collection kit is designed to detect. Beneficially, this can provide protection to a user of the kit from the potential contaminants in the fluid of the collection device.

Figure 4:
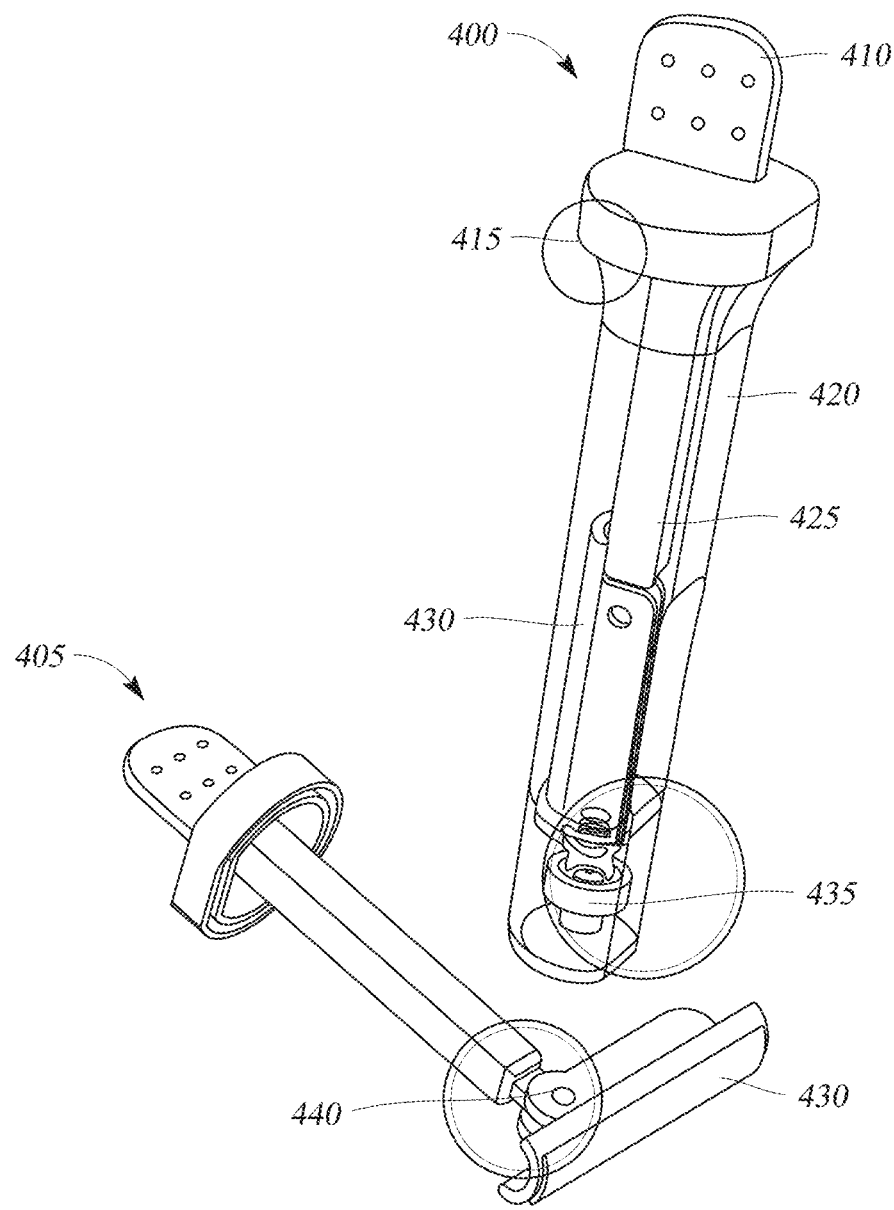
FIG. 4 illustrates an example of a closed system contaminant collection device.

FIG. 4 illustrates an example of a closed system contaminant collection device 400. The collection device 400 can include a handle 405 that can be releasably coupled with container 420 to provide a fluid-tight enclosure. FIG. 4 shows the handle both coupled with container 420 and separate from container 420. Mechanisms to couple the handle 405 with the container 400 can include those described above with reference to FIG. 1A-, or other suitable mechanisms.

The handle 405 can include cap 415 and grasping tab 410 of cap 415, an elongate handle 425 extending from cap 415 to swab 430, swab 430, and a pivot 440. The swab 430 can be constructed from a material having desired pickup efficiency and shedding efficiency for detecting trace amounts of contaminants, examples of which are discussed in more detail below. Handle 425 can have sufficient length so that the user can swab a surface without physically contacting the surface or the swab 430. The swab 430 (or a base to which swab 430 is coupled) can be pivotably coupled to the handle 425 via pivot 440. The handle 425 can be coupled to or an integral part of the cap 415 in some embodiments. A user can hold the handle 405 by the tab 410 during wiping of a test surface.

A liquid, for example a buffer solution, can be provided within the container 420 so that the user removes a pre-wetted swab to wipe the surface (and optionally pours additional fluid onto the surface from the container 420) in one implementation. In another implementation, the user can spray the surface with a liquid and collects this liquid with the swab.

After swabbing the surface, the user places the swab 430 into the container 420 and the cap 415 forms a liquid-tight seal when engaged with the container 420. The cap 415 can additionally lock to the container.

The container 420 advantageously prevents liquid from spilling and contaminating surfaces or users, but provides for controlled release of fluid to a detection device. The detection device can be an immunoassay, for example a lateral flow assay, with an interface that alerts the user to the presence and/or degrees of contamination. Controlled release of the fluid can be provided through a release mechanism, such as valve 435, when the container 430 is coupled to a detection device. Thus, valve 435 can be incorporated into a coupling mechanism for coupling the collection device 400 to a portion of a detection device to create a closed fluid transfer system.

Figure 5A:
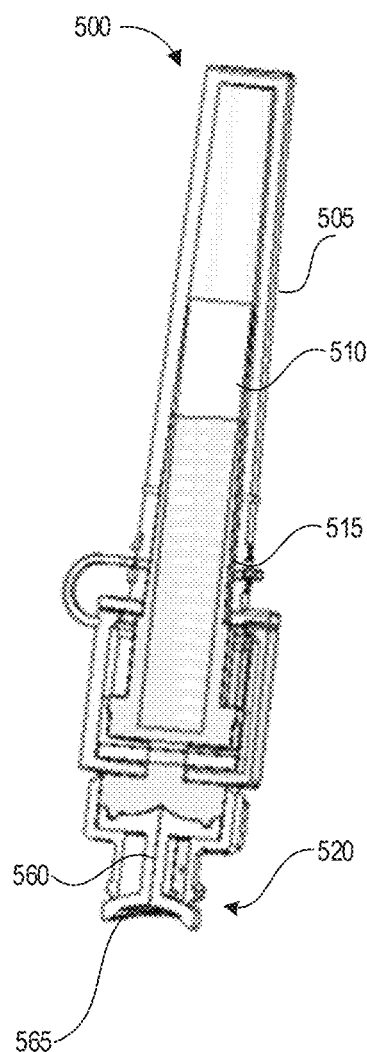
FIGS. 5A-5D illustrate another example of a closed system contaminant collection device and an example of a closed system detection device.
Figure 5B:
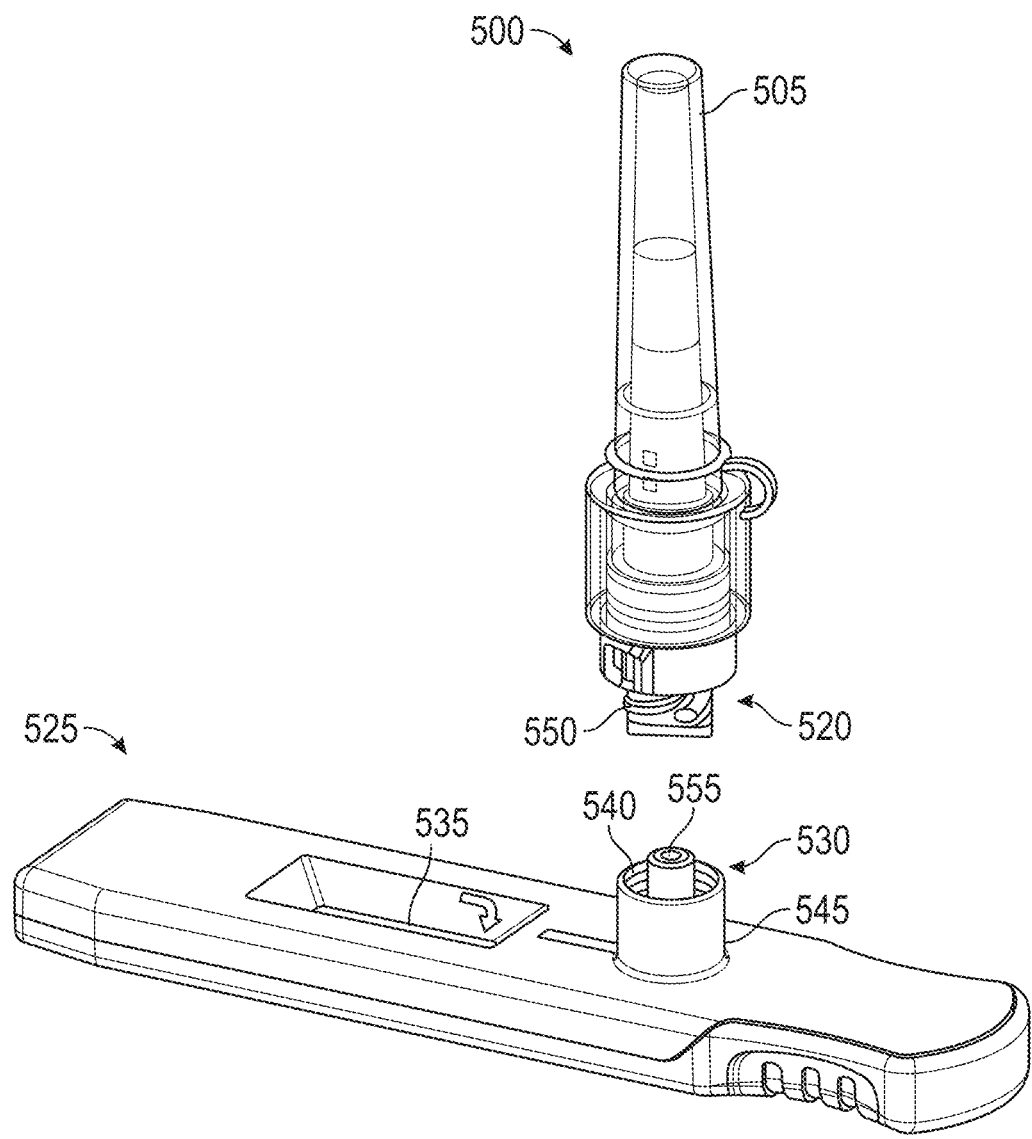
Figure 5C:
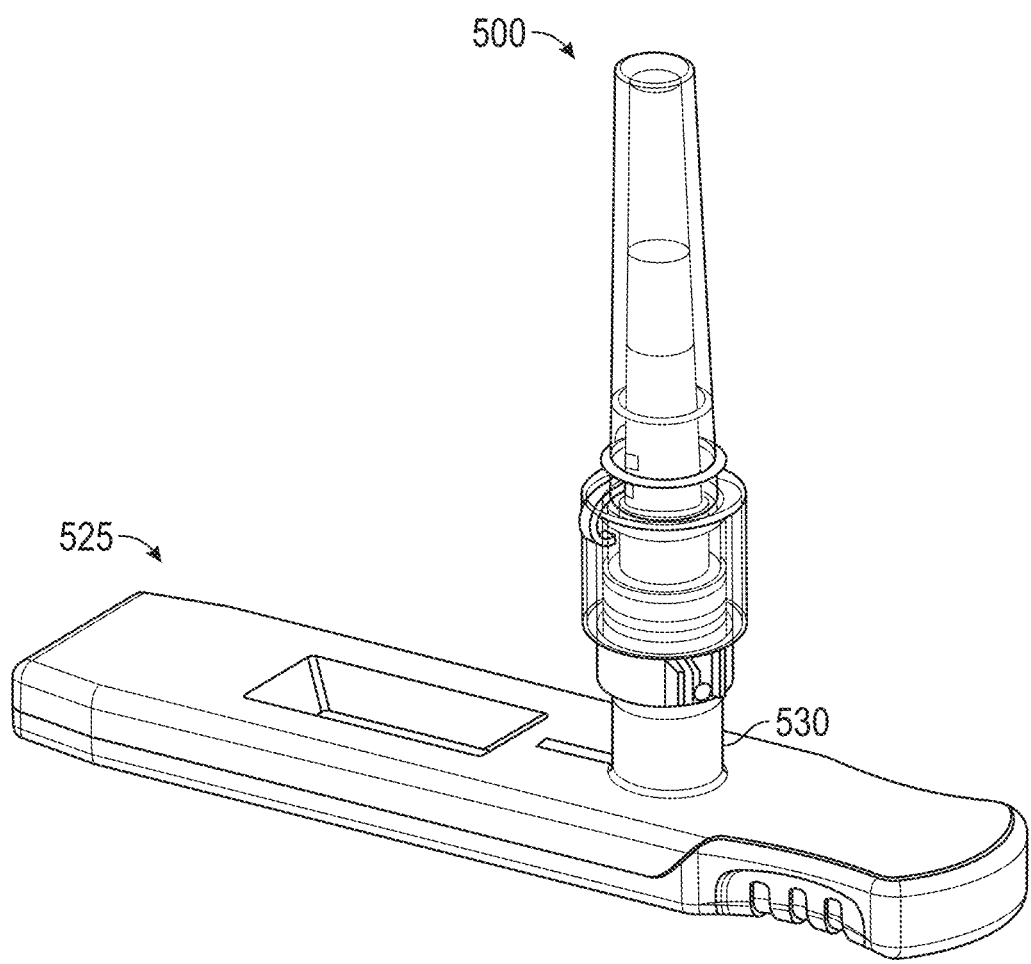
Figure 5D:
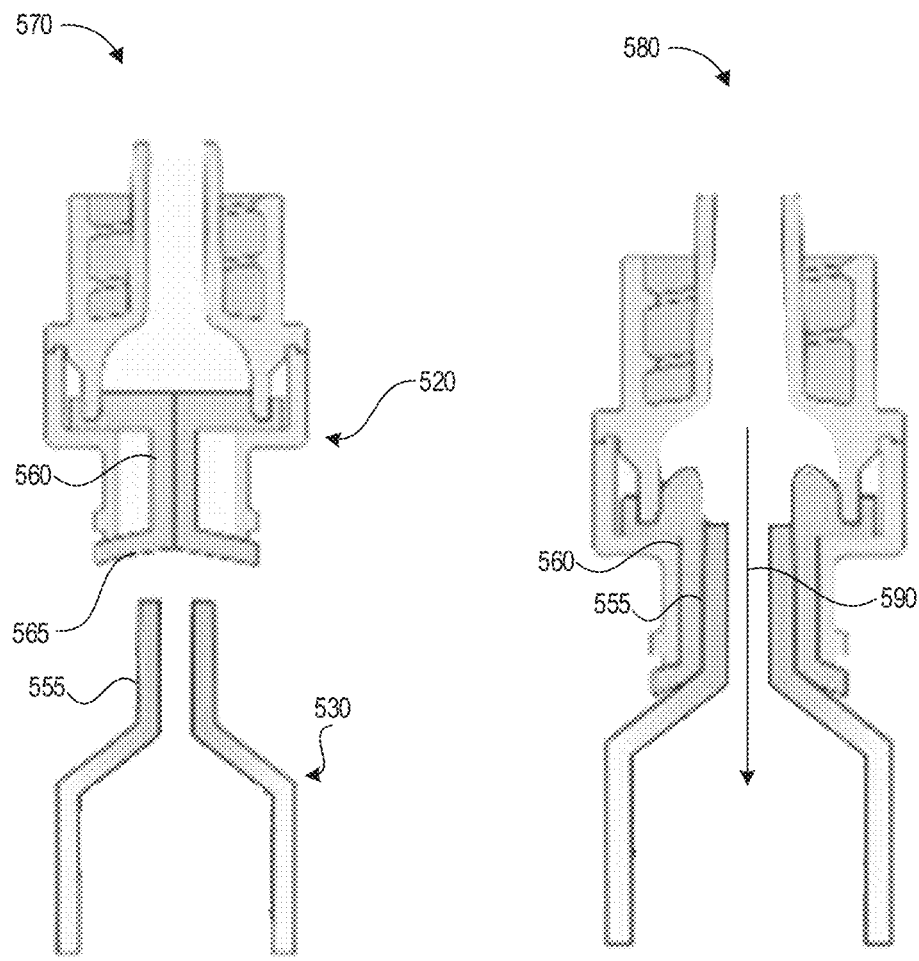

FIGS. 5A-5D illustrate another example of a closed system contaminant collection device 500 and an example of a closed system test strip 525. FIG. 5A illustrates a cut-away view of the collection device 500. FIG. 5B illustrates the collection device 500 and test strip 525 in a separated configuration. FIG. 5C illustrates the collection device 500 and test strip 525 in a coupled configuration. FIG. 5D illustrates an example set of fluid transfer couplings for providing a closed fluid path between the container 505 and test strip 525.

The collection device 500 includes a fluid-tight container 505 containing a volume of fluid 510 and swab 515. Collection device 500 further includes fluid transfer coupling 520 for providing a fluid-tight mechanical coupling to test strip 525 such that fluid can be transferred between the collection device 500 and the test strip 525 without escaping from the coupled closed system. A valve 560 of fluid transfer coupling 520 can be biased closed when the collection device 500 and test strip 525 are separated, and FIG. 5A shows the valve 560 in the closed position. The valve 560 can include a tapered or contoured lower surface 565. In some embodiments, the valve 560 can be a split septum valve, and in some embodiments valve 560 may be a mechanical valve.

The test strip 525 can be housed within a cartridge that includes coupling 530 for mechanically and fluidically coupling to the fluid transfer coupling 520 of the collection device 500. As illustrated, some implementations of the coupling 530 can include threads 540 along an interior of sleeve 545 for mechanically mating the coupling 530 with the threads 550 of the fluid transfer coupling 520. The coupling 530 can also include a nozzle 555 having an internal lumen for providing a fluidic pathway between the fluid transfer coupling 520 and the coupling 530. Nozzle 555 may be a male leur tip in some embodiments. The contoured or tapered lower surface 565 of fluid transfer coupling 520 may ease connection with the nozzle 555 of the cartridge coupling 530 by guiding the nozzle 555 into the center of the fluid transfer coupling 520. In embodiments of the fluid transfer coupling 520 that implement a mechanical valve 560, a portion of the valve may open upon contact with the nozzle 555, either by displacement along the longitudinal axis of the fluid transfer coupling 520 or by radial displacement towards the circumferential edges of the fluid transfer coupling 520. In the open configuration, fluid flows through the valve 560 and into the nozzle 555.

As the collection device 500 is screwed into the coupling 530, the nozzle 555 can contact the lower surface 565 of the valve 560, thereby opening the valve 560 to release fluid into the nozzle 555. The fluid transfer coupling 520 can be a needleless connector, for example the MaxPlus™ needleless connector, MaxZero™ needleless connector, BD Q-Syte™ luer activated split septum, or SmartSite™ needle-free connectors available from Becton, Dickinson and Company (BD). Some embodiments of nozzle 555, container 510, and/or fluid transfer coupling 520 can be structured to allow only a controlled volume of fluid to pass, such as a volume suitable for flowing along the length of the test strip from a sample receiving zone to an analyte binding region 535 of the test strip. In some examples, the desired volume can include three to four drops of fluid. Nozzle 555 can be positioned to transfer fluid to the sample receiving zone of the test strip within the cartridge.

As shown in FIG. 5C, when coupled the sleeve 545 of the coupling 530 surrounds the fluid transfer coupling 520. Some embodiments of sleeve 545 can optionally provide a fluid-tight seal with a lower portion of the container 510. In the configuration shown in FIG. 5C, a sealed fluid pathway is established between the container 510 and the sample receiving zone of the assay test strip via the mated container fluid transfer coupling 520 and cartridge coupling 530.

FIG. 5D illustrates cross-sections of one example of suitable closed-path fluid transfer couplings in uncoupled 570 and coupled 580 states. The cartridge coupling 530 is illustrated at a high level without the sleeve 545 or threads 540. As illustrated, in the uncoupled state 570 the valve 560 is closed and the nozzle 555 (e.g., a male luer tip) approaches the contoured or tapered lower surface 565. In the uncoupled state 570 the valve 560 extends across the entire cross-section of the fluid transfer coupling 520, preventing egress of any fluid from the container 505. Pushing the nozzle 555 into the valve 560 (for example by threading the fluid transfer coupling 520 and coupling 530 into the configuration of FIG. 5C) forces the valve 560 to open around the nozzle 555, thereby establishing an enclosed fluid path 590 from the container 505 through the lumen of the nozzle 555. The illustrated valve 560 is made from a flexible material that enables it to deform around the nozzle 555. Upon removal of the nozzle 555, the valve 560 automatically returns to the closed position shown in the uncoupled state 570, closing the fluid pathway and preventing spillage of potentially contaminated liquid from the container 505. The couplings shown in FIG. 5D can be incorporated into any of the collection devices shown herein, for example into the nozzle 110 of the container 130.

In some embodiments, a user can shake or otherwise agitate the collection devices shown in FIGS. 4 and 5A-5C prior to transferring the fluid to a detection device in order to release collected contaminants from the swab into the buffer fluid in the container. For example, the container can be inverted a number of times to allow the buffer fluid to flow back and forth across the material of the swab. The buffer fluid can have properties that assist in releasing collected contaminants from the swab material in some implementations, as discussed in more detail below. As such, the flow of the buffer fluid can extract the contamination from the material of the swab and mix it into a homogeneous solution for testing.

Figure 6:
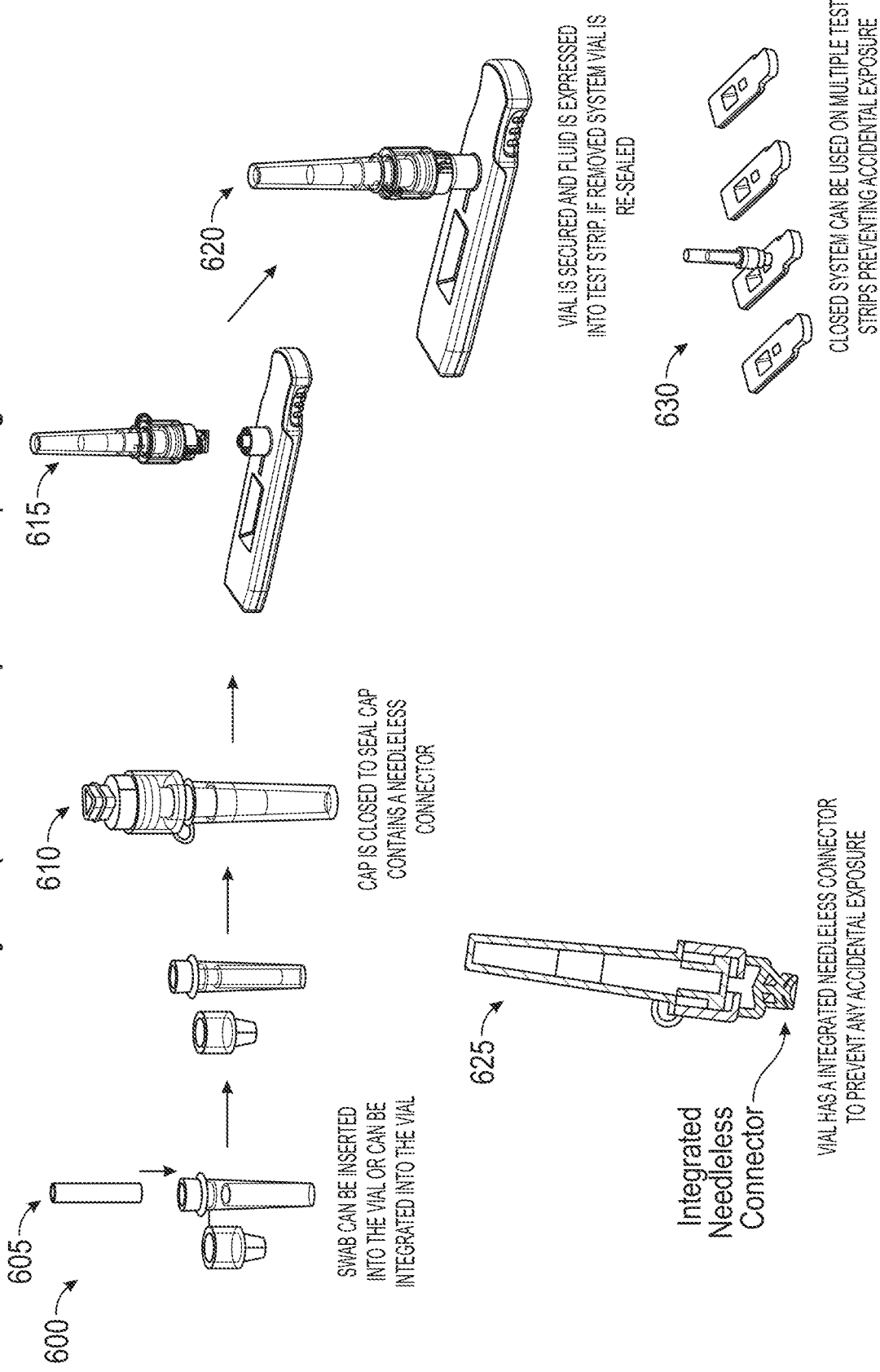
FIG. 6 illustrates example steps of a testing method using a closed system contaminant collection device.

FIG. 6 illustrates example steps of a testing method 600 using a closed system contaminant collection device and closed system detection device, such as those described above with respect to FIGS. 4 and 5A-5C.

At step 605, a swab can be inserted into the vial. In some embodiments the swab can be integrated into a vial. The vial can be for example, the container 420 illustrated in FIG. 4, the fluid-tight container 505 illustrated in FIG. 5, or another suitable structure.

At step 610, a cap can be closed to seal the vial. The cap can include a needleless connector or other closed fluid transfer mechanism as described above.

At step 615, the vial can be inverted above a test strip. Because the vial is fluid-tight, no fluid escapes from the vial during inversion.

At step 620, the vial is coupled, mechanically and fluidically, to the closed system detection device, in this non-limiting example a test strip cartridge. A volume of fluid can be expressed from the vial onto a sample receiving zone of the test strip in the cartridge.

At step 625, the vial is removed from the test strip cartridge and the integrated needleless connector re-closes and re-seals to prevent fluid from escaping from the closed system contaminant collection device.

Optionally, as shown at step 630, the vial can be disconnected from the test strip to allow the vial to be coupled to additional test strips using the original collected sample. Advantageously, in some embodiments a test kit can include multiple test strips for testing for different contaminants and/or different concentrations of the same contaminant.

Overview of Example Assay Reader Devices and Operations

Figure 7A:
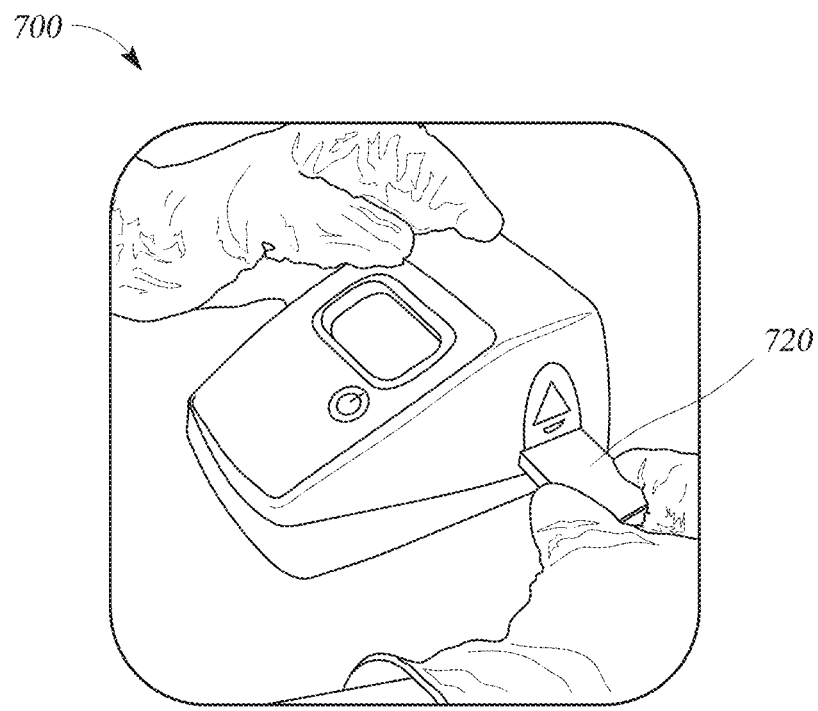
FIGS. 7A through 7C illustrate an example testing device.
Figure 7B:
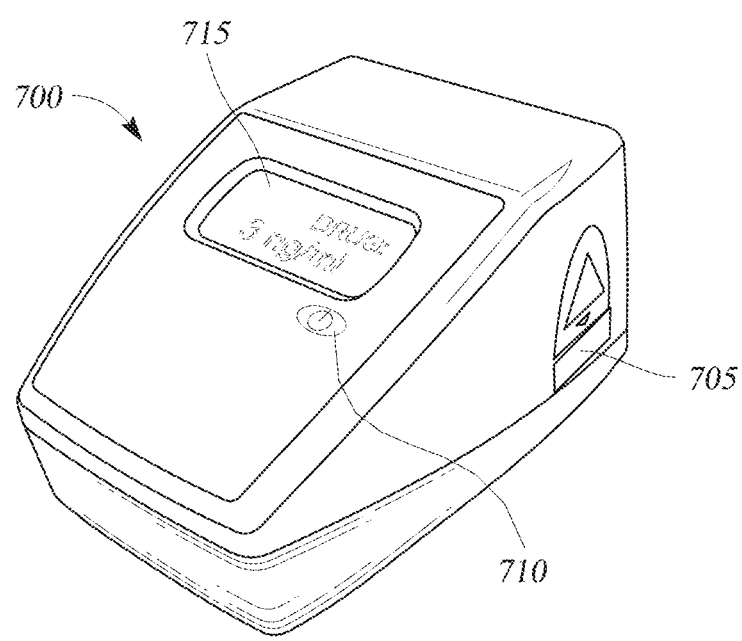

FIGS. 7A and 7B illustrate an example testing device 700 that can be included in or used with hazardous contamination detection kits described herein. FIG. 7A illustrates the testing device 700 with an assay cartridge 720 inserted into the cartridge receiving aperture 705, and FIG. 7B illustrates the testing device 700 without an inserted cartridge. Examples of the assay cartridge 720 include but are not limited to the test strip 145 illustrated in FIG. 1A, the test strip illustrated in FIGS. 3A and 3B, the test strip 525 illustrated in FIGS. 5B and 5C, and the test strips 630 illustrated in FIG. 6.

The testing device 700 can be an assay reader device having an aperture 705 for receiving an assay test strip and cartridge 720 and positioning the test strip so that analyte binding regions are positioned in the optical path of imaging components located inside of the device 700. The device can also use these or additional imaging components to image a bar code on the cartridge, for example to identify which imaging techniques and analysis to perform.

Some embodiments of the device 700 can be configured to perform an initial scan, for example using a bar code scanner to image one or more bar codes. A bar code can identify the type of test to be performed, the person conducting the test, the location of the test, and/or the location in the facility of the test surface (for example pharmacy, nursing area, cabinet #, bed #, chair #, pump #, etc.). After reading the bar code identifier the cartridge is then inserted into the reader as shown in FIG. 7A.

The device 700 can have a button 710 that readies the device for use and provides an input mechanism for a user to operate the device. In some embodiments device operation mode can be set via a number or pattern of clicks of the single button 710 of the device 700. For example, in some implementations a single press of the button 710 can power on the device 700 and set the device 700 to a default operation mode, and the device 700 can implement the default operation mode upon insertion of a cartridge. A double-click of the button 710 can initiate an alternate operation mode that is different than the default operation mode. Other numbers or patterns of pressing the single button 710 by a user can provide instructions to the processor of the device regarding a desired operation mode. Embodiments of a device 700 are described herein with reference to a single button, but other features allowing a user to select and switch between device operation modes are possible (such as but not limited to a single switch, knob, lever, or handle).

One example of a device operation mode is end-point read mode. In the end-point read mode, the user prepares and incubates the assay outside of the device 700 and tracks the development time of the assay. For example, an assay for determining Methotrexate or Doxorubicin concentration can have a development time of 5 minutes, so the user would apply the fluid to the assay from a collection device as described herein and wait for 5 minutes. At the end of the 5 minutes the user would insert the assay 720 into the device 700 to obtain a test result. Accordingly, when operating in end-point read mode the device 700 can provide instructions, for example audibly or on a visual display, that instruct a user to wait for a predetermined time after applying a sample to an assay before inserting the assay in the device 700. In other embodiments, when operating in end-point read mode the device 700 may not display any instructions but may simply read an assay upon insertion into the device 700. Upon insertion of the assay into the base device 700, an optical reader of the device can collect data (for example, image data) representing the assay for analysis in determining a result of the assay. In some embodiments end-point read mode can be the default operation mode of the device 700.

Another example of a device operation mode is walkaway mode. When operating in walkaway mode, the device 700 can provide instructions for the user to insert the assay immediately after or during application of the sample. In the walkaway mode according to one embodiment, the user can apply the specimen to the assay and immediately insert the assay into the device 700. The assay will develop inside the device 700 and the device 700 can keep track of the time elapsed since insertion of the assay 720. At the end of the predetermined development time, the device 700 can collect data (for example, image data) representing the assay. In implementations where the device 700 is an imaging reader, the device 700 can analyze the image data to determine a test result, and report the test result to the user. The assay development time can be unique to each test. In some embodiments walkaway mode can be set by double-clicking the single button 710 of the device 700. Further input can indicate the assay development time to the reader device. For example, a barcode scanned by a barcode reader, or a barcode provided on the assay or on a cartridge used to hold the assay, can indicate to the device 700 a type of assay that is inserted and a development time for that assay. Based upon the type of assay, the device 700 can wait for the predetermined amount of time after sample application and insertion before collecting image data representing the assay.

There are many advantages associated with the ability of a user to select and switch between device operation modes in implementations of base assay analyzers described herein. The endpoint read mode can be convenient in large laboratories or medical practice facilities where personnel typically batch process a number of tests. The walkaway mode can be useful when a single test is being performed, or when the end user does not want to have to track the assay development time (or is not knowledgeable or not trained on how to track the assay development time accurately). The walkaway mode can advantageously reduce or eliminate the occurrence of incorrect test results due to an assay being inserted and read (for example, imaged) too quickly (too soon before the development time of the assay has elapsed) or too slowly (too long after the development time of the assay has elapsed). Further, in walkaway mode the assay reader can operate to capture multiple images of the assay at predetermined time intervals, for example when a kinetic graph of the assay readings is desired.

One embodiment of the disclosed device 700 includes only a single button 710 on its exterior housing, such as a single power button that powers the device 700 off and on. Embodiments of the disclosed device 700 also implement two different device operation modes (although more than two device operation modes are possible). In order to enable the end user to select and switch between the two device operation modes, the device 700 can include instructions to implement a double-click function on the power button. After receiving input of a single press of the button to power on the device, insertion of an assay cartridge can automatically trigger end-point read mode. When the processor of the device receives input from a user double-clicking the power button, this can initiate the stored instructions to implement the walkaway mode. This double-click functionality offers a simple and intuitive way for the end user to switch between different operation modes of the base assay analyzer. The double-click functionality also enables the user to configure the device in real time to operate in the walkaway mode without requiring any additional configuration steps or additional programming of the device 700 by the user. It will be appreciated that the device 700 can be provided with instructions to recognize other click modes instead of or in addition to the double-click to trigger secondary (non-default) device operation modes, for example to recognize a user pressing the button any predetermined number of times, pressing the button in a predetermined pattern, and/or pressing and holding the button for a predetermined length of time.

The device 700 can also include a display 715 for displaying instructions and/or test results to the user. After insertion of the test strip, the device 700 can read a bar code on the assay test strip to identify the name and/or concentration range of the drug. The device 700 can image the inserted test strip, and analyze the signals representing the imaged test strip to calculate results, display the results to the user, and optionally transmit and/or locally store the results. The results can be calculated and displayed as contamination with an indication of positive or negative (for example, +/−; yes/no; etc.), and/or the actual contamination per area (for example, Drug Concentration=0.1 ng/cm2) and/or per volume (for example, Drug Concentration=3 ng/ml)

Some embodiments of the device 700 may simply display the result(s) to the user. Some embodiments of the device 700 may also store the result(s) in an internal memory that can be recalled, for example, by USB connection, network connection (wired or wireless), cell phone connection, near field communication, Bluetooth connection, and the like. The result(s) can also automatically be logged into the facility records and tracking system. The device 700 can also be programmed to automatically alert any additional personnel as required, without further input or instruction by the user. For example, if the device 700 reads contamination levels that are above the threshold of human uptake and considered hazardous to for human contact, a head pharmacist, nurse, manager, or safety officer can be automatically notified with the results and concentration of contamination to facilitate a rapid response. The notification can include location information, such as but not limited to a geographic position (latitude/longitude) or description of location (Hospital A, Patient Room B, etc.). That response may include a detailed decontamination routine by trained personnel or using a decontamination kit provided together or separately from the hazardous contamination detection kit.

In some embodiments, device 700 can be a special-purpose assay reader device configured with computer-executable instructions for identifying trace concentrations of contaminants in the samples applied to test strips. Further components of the device 700 are discussed below with respect to the diagram of FIG. 8.

Figure 7C:
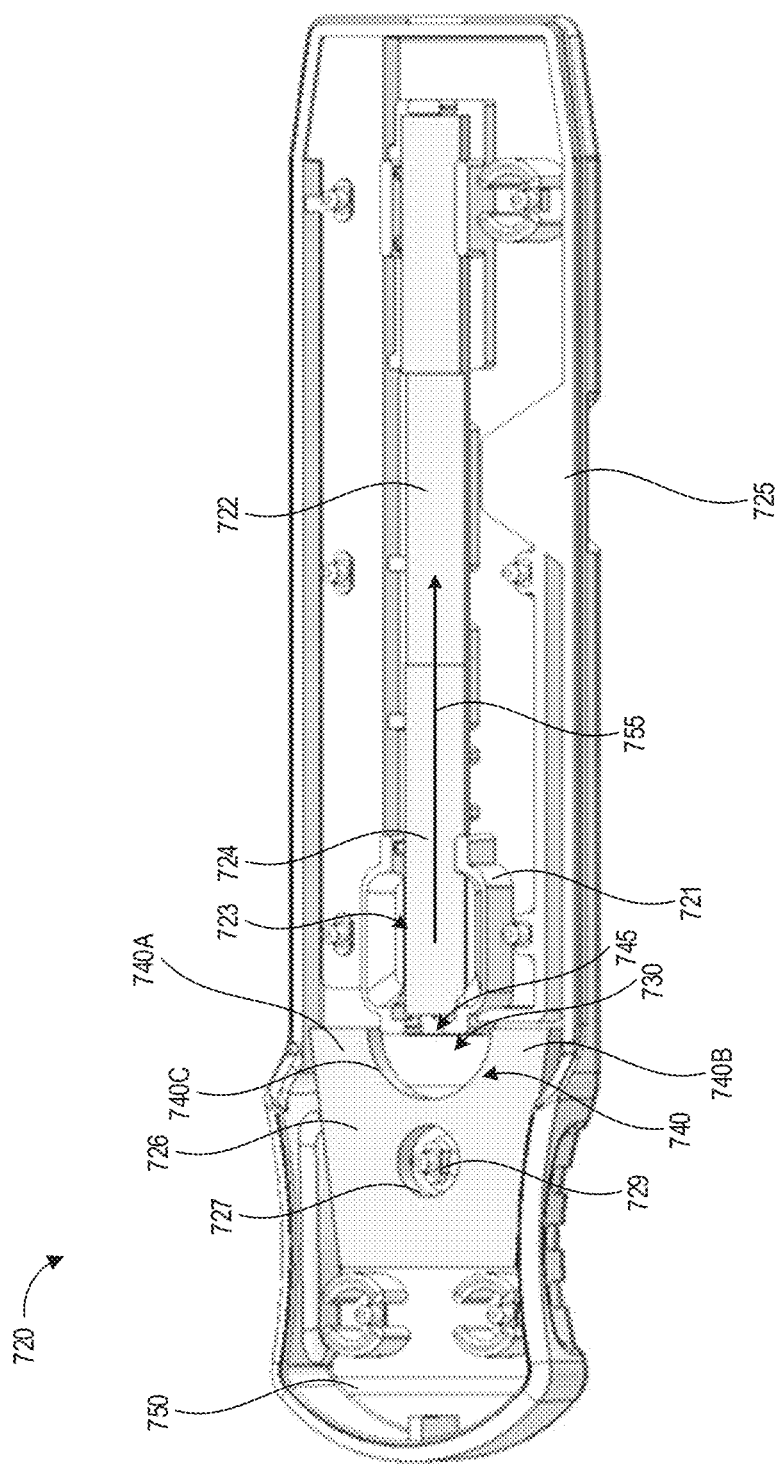

FIG. 7C illustrates a cut-away view showing interior features of an example of the assay cartridge 720. An assay test strip 723 including sample receiving zone 724 at a proximal end and analyte binding zone 722 at a distal end. The analyte binding zone 722 can be secured within a first region 721 of the cartridge housing 725. Capillary action can cause applied liquid to flow from the sample receiving zone 724 to the analyte binding zone 722 along a lateral flow direction 755. The first region 721 includes an exit aperture 745 through which any excess fluid overflowing backwards relative to the lateral flow direction 755 from the sample receiving zone 724 is directed. An overflow pad 726 can be secured in a second region 750 (e.g., within a grip portion of the cartridge 720) that is positioned upstream of the first region 721, where "upstream" refers to the second region 750 being positioned closer to the proximal end of the test strip 723 than the first region 721 along the lateral flow direction 755. For example, the overflow pad 726 can be secured via an aperture 727 and corresponding protrusion 729 on the cartridge housing 725 or by other suitable fixing features (e.g. clips, adhesives, and/or clamping together of two halves of the cartridge housing 725).

The overflow pad 726 can be made from an absorbent material, and can operate to absorb any excess fluid that flows out of the assay test strip 723, thereby preventing such fluid from escaping the housing 725 and protecting the user from contacting potentially hazardous fluid. For example, if the user drips too much fluid onto the sample receiving zone 724, some fluid can run out of the exit aperture 745 and out of the assay strip 723 into the cartridge interior. This fluid can then leak out of the cartridge, spreading any contamination present in the fluid. Embodiments of assay cartridge 720 that include overflow pad 726 can collect such fluid and contain it within the cartridge 720. If the overflow pad 726 is placed too close to the assay strip 723 (e.g., in contact with the assay test strip 723) then the overflow pad 726 may reverse the intended lateral flow direction by drawing out fluid that would flow along the assay test strip 723 from the sample receiving zone 724 to the analyte binding zone 722 during normal operation. Embodiments of assay cartridge 720 allow at least some fluid needs to flow away from the overflow pad 726 to the analyte binding zone 722 for development of test results. Accordingly, in some embodiments, the overflow pad 726 can be spaced apart from the proximal end of the assay test strip 723 by a gap 730.

The overflow pad 726 can also be shaped to have a contoured end 740 that faces the assay test strip 723, for example shaped as two prongs 740A, 740B and a curved edge 740C forming a negative space between the two prongs 740A, 740B as in the illustrated example. The curved edge 740C wraps around the exit aperture 745 to block fluid paths of excess fluid traveling out of the exit aperture 745. Thus, the design of the contoured end 740 encapsulates the space around the exit aperture 745, thereby absorbing any excess fluid that travels out of the exit aperture 745 take so that it cannot escape from the cartridge 720. At the same time, the curved edge 740C keeps the overflow pad 726 far enough away from the proximal end of the assay test strip 723 to ensure that the overflow pad 726 does not wick fluid out of the assay test strip 723.

Figure 8:
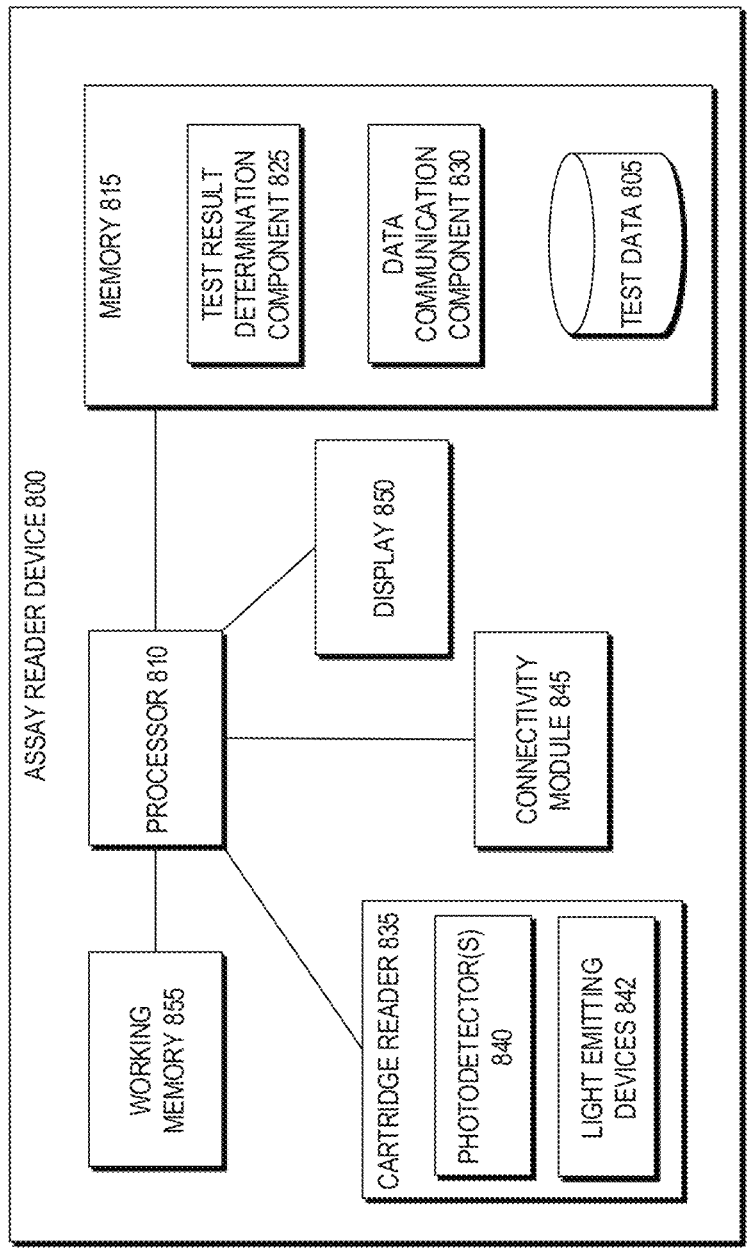
FIG. 8 depicts a high level schematic block diagram of an example testing device.

FIG. 8 illustrates a schematic block diagram of one possible embodiment of components of an example assay reader device 800. The components can include a processor 810 linked to and in electronic communication with a memory 815, working memory 855, cartridge reader 835, connectivity module interface 845, and display 850.

Connectivity module 845 can include electronic components for wired and/or wireless communications with other devices. For example, connectivity module 845 can include a wireless connection such as a cellular modem, satellite connection, or Wi-Fi, or via a wired connection. Thus, with connectivity module 845 the assay reader device can be capable of sending or uploading data to a remote repository via a network and/or receiving data from the remote repository. As such, the test data of such assay reader devices can be stored and analyzed, alone or in the aggregate, by remote devices or personnel. A module having a cellular or satellite modem provides a built-in mechanism for accessing publicly available networks, such as telephone or cellular networks, to enable direct communication by the assay reader device with network elements or other testing devices to enable electronic test result transmission, storage, analysis and/or dissemination without requiring separate intervention or action by the user of the device. In some embodiments connectivity module 845 can provide connection to a cloud database, for example a server-based data store. The cloud based connectivity module can enable ubiquitous connectivity of assay reader devices without the need for a localized network infrastructure.

The cartridge reader 835 can include one or more photodetectors 840 for reading an assay held in an inserted cartridge and optionally any information on the inserted cartridge, for example a barcode printed on the cartridge, and one or more light emitting devices 842 for illuminating the inserted cartridge at one or more wavelengths of light. The cartridge reader 835 can send image data from the one or more photodetectors to the processor 810 for analysis of the image data representing the imaged assay to determine a test result of the assay. The cartridge reader 835 can further send image data from the one or more photodetectors representing the imaged cartridge for use in determining which one of a number of automated operating processes to implement for imaging the assay and/or analyzing the image data of the assay. The photodetector(s) 840 can be any device suitable for generating electric signals representing incident light, for example a PIN diode or array of PIN diodes, a charge-coupled device (CCD), or a complementary metal oxide semiconductor (CMOS) sensor, to name a few examples. The cartridge reader 835 can also include a component for detecting cartridge insertion, for example a mechanical button, electromagnetic sensor, or other cartridge sensing device. An indication from this component can instruct the processor 810 to begin an automated assay reading process without any further input or instructions from the user of the device 800.

Processor 810 can be configured to perform various processing operations on image data received from the cartridge reader 835 and/or connectivity module interface 845 in order to determine and store test result data, as will be described in more detail below. Processor 810 may be a general purpose processing unit implementing assay analysis functions or a processor specially designed for assay imaging and analysis applications. The processor 810 can be a microcontroller, a microprocessor, or ASIC, to name a few examples, and may comprise a plurality of processors in some embodiments.

As shown, the processor 810 is connected to a memory 815 and a working memory 855. In the illustrated embodiment, the memory 815 stores test result determination component 825, data communication component 830, and test data repository 805. These modules include instructions that configure the processor 810 of device 800 to perform various module interfacing, image processing, and device management tasks. Working memory 855 may be used by processor 810 to store a working set of processor instructions contained in the modules of memory 815. Alternatively, working memory 855 may also be used by processor 810 to store dynamic data created during the operation of device 800.

As mentioned above, the processor 810 may be configured by several modules stored in the memory 815. The test result determination component 825 can include instructions that call subroutines to configure the processor 810 to analyze assay image data received from the photodetector(s) 840 to determine a result of the assay. For example, the processor can compare image data to a number of templates or pre-identified patterns to determine the test result. In some implementations, test result determination component 825 can configure the processor 810 to implement adaptive read processes on image data from the photodetector(s) 840 to improve specificity of test results and to reduce false-positive results by compensating for background and non-specific binding.

The data communication component 830 can determine whether a network connection is available and can manage transmission of test result data to determined personnel and/or remote databases. If the device 800 is not presently part of a network, the data communication component 830 can cause local storage of test results and associated information in the test data repository 805. In some case, the device 800 can be instructed to or automatically transmit the stored test results upon connection to a network. If a local wired or wireless connection is established between the device 800 and another computing device, for example a hospital, clinician, or patient computer, the data communication component 830 can prompt a user of the device 800 to provide a password in order to access the data in the repository 805.

The processor 810 can be configured to control the display 850 to display captured image data, imaged barcodes, test results, and user instructions, for example. The display 850 may include a panel display, for example, a LCD screen, LED screen, or other display technologies, and may implement touch sensitive technologies.

Processor 810 may write data to data repository 805, for example data representing captured images of assays, instructions or information associated with imaged assays, and determined test results. While data repository 805 is represented graphically as a traditional disk device, those with skill in the art would understand that the data repository 805 may be configured as any storage media device. For example, data repository 805 may include a disk drive, such as a hard disk drive, optical disk drive or magneto-optical disk drive, or a solid state memory such as a FLASH memory, RAM, ROM, and/or EEPROM. The data repository 805 can also include multiple memory units, and any one of the memory units may be configured to be within the assay reader device 800, or may be external to the device 800. For example, the data repository 805 may include a ROM memory containing system program instructions stored within the assay reader device 800. The data repository 805 may also include memory cards or high speed memories configured to store captured images which may be removable from the device 800.

Although FIG. 8 depicts a device having separate components to include a processor, cartridge reader, connectivity module, and memory, one skilled in the art would recognize that these separate components may be combined in a variety of ways to achieve particular design objectives. For example, in an alternative embodiment, the memory components may be combined with processor components to save cost and improve performance.

Additionally, although FIG. 8 illustrates a number of memory components, including memory 815 comprising several modules and a separate memory 855 comprising a working memory, one of skill in the art would recognize several embodiments utilizing different memory architectures. For example, a design may utilize ROM or static RAM memory, internal memory of the device, and/or an external memory (e.g., a USB drive) for the storage of processor instructions implementing the modules contained in memory 815. The processor instructions may be loaded into RAM to facilitate execution by the processor 810. For example, working memory 855 may comprise RAM memory, with instructions loaded into working memory 855 before execution by the processor 810.

Overview of Further Examples of Contaminant Collection Devices

Figure 9B:
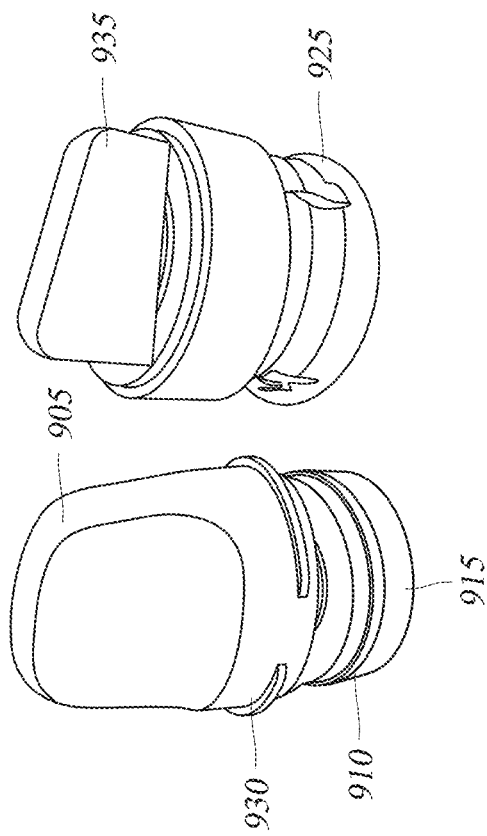
FIGS. 9A and 9B illustrate another example of a contaminant collection device.
Figure 9A:
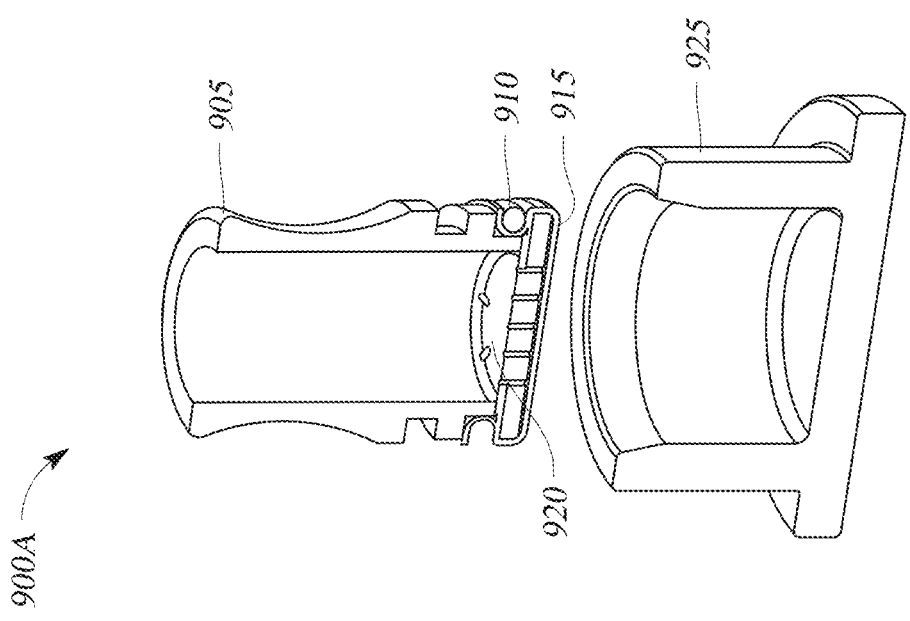

FIGS. 9A and 9B illustrate examples of a contaminant collection device 900A, 900B that can be used in hazardous contamination detection kits described herein. FIG. 9A illustrates a cross-sectional view of a first embodiment of the collection device 900A with a handle 905 removed from a container 925. FIG. 9B illustrates another embodiment of the collection device 900B with the handle 905 removed from the container 925 and a cap 935 in the container 925.

The collection device 900A, 900B includes a swab 915 attached to a handle 905 that allows the user to wipe the surface to be tested by holding only the handle 905 and not contacting the surface. After wiping the surface, the handle is inserted into a container 925 with additional buffer solution (not illustrated). When the handle 905 is inserted into the container 925, the sides of the handle seal with the interior of the container, for example by O-ring 910. As the handle approaches the bottom of the container, either by simply pressing or with the assistance of a threaded engagement between the handle 905 and the container 925, the buffer solution is pressurized and forced through the swab fabric, through small holes 920 in the handle, and into the handle interior. Partial removal of the handle can create a vacuum, sucking the buffer solution back through the swab fabric again. Repeating this process multiple times helps to flush the collected contaminations from the fabric creating a homogeneous solution. The structure of the collection device 900A, 900B positively forces the buffer fluid through the fabric as a means of extracting the contamination from the fabric.

A needleless connection system, such as that discussed above with respect to FIGS. 5A-5C, can be incorporated into the handle 905 to allow for the closed transfer of buffer solution from the interior of the handle to a test device. The embodiment 900A of FIG. 9A does not show a needleless connection system. The embodiment 900B of FIG. 9B includes threads 930 to assist in the creation of the pressure and vacuum as well as an attachment point for the needleless connector. FIG. 9B also shows a cap 935 for the container 925 to contain the buffer solution until use.

Figure 10A:
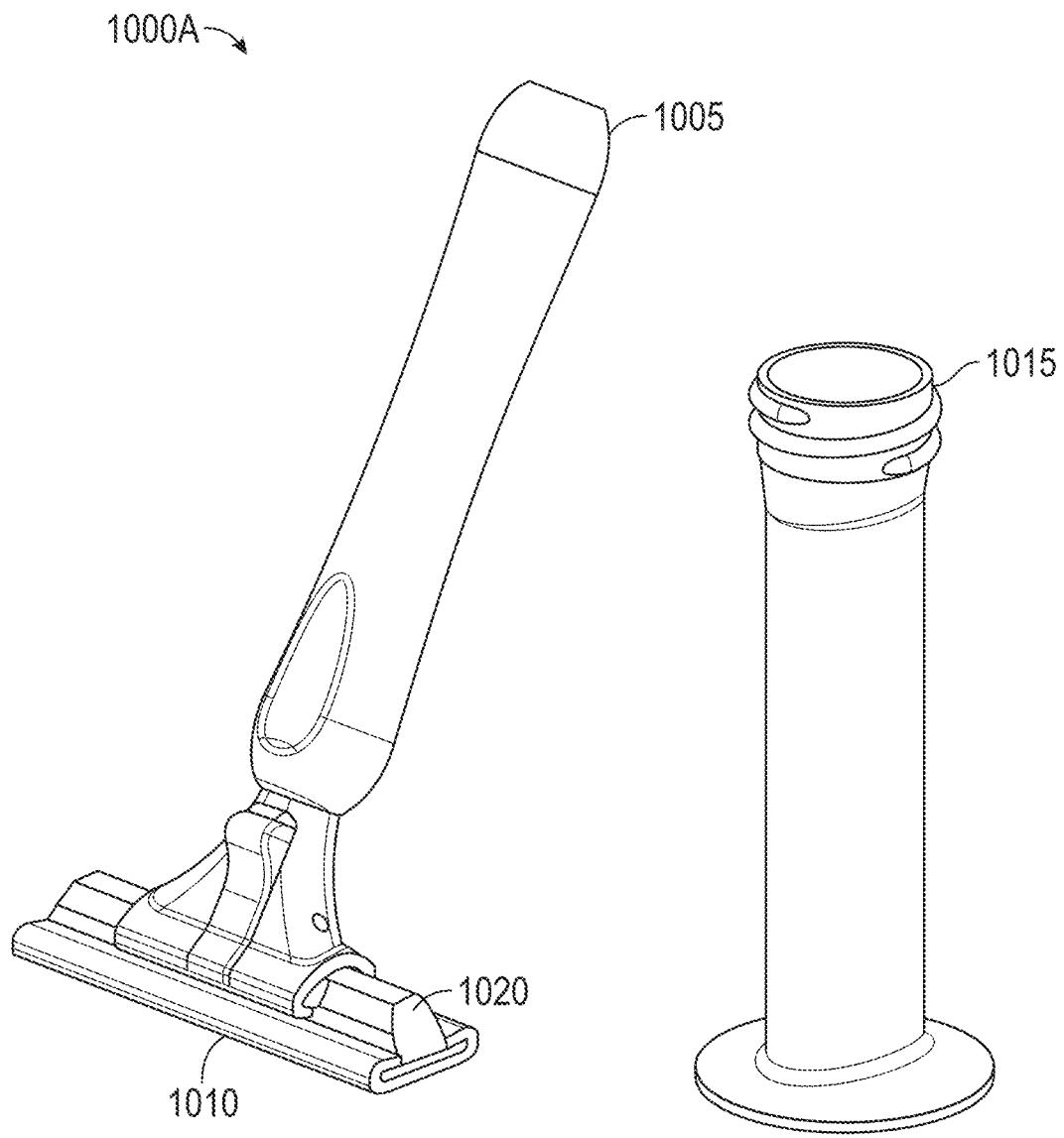

FIG. 10A illustrates another example of a contaminant collection device 1000A that can be used in hazardous contamination detection kits described herein. In this embodiment, a swab material 1010 is attached to a detachable base 1020 of a handle 1005, which is then attached to the handle 1005 using a releasable attachment mechanism similar to a razor handle. After the user swabs a surface (using a motion similar to using a razor to shave), the swab base 1020 can be disconnected from the handle 1005 and dropped into a container 1015 containing a buffer solution. The container can be capped and then inverted a number of times to flow the buffer solution back and forth across the swab 1010 to extract any contaminants. The container 1015 can include an interior portion shaped to correspond to the shape and size of the swab 1010, similar to the FIGS. 1A-1L configuration. In one example where device 1000A is a closed system contaminant collection device, the container 1015 may contain a needleless connection system as described above, either in the bottom of container 1015 or as part of a cap (not shown), in order to transfer the buffer mixture to a test device. In another example where device 1000A is an open system contaminant collection device, the cap may also contain an orifice that allows for single drops of the buffer mixture to be dripped out of the container onto the test strip.

Figure 10B:
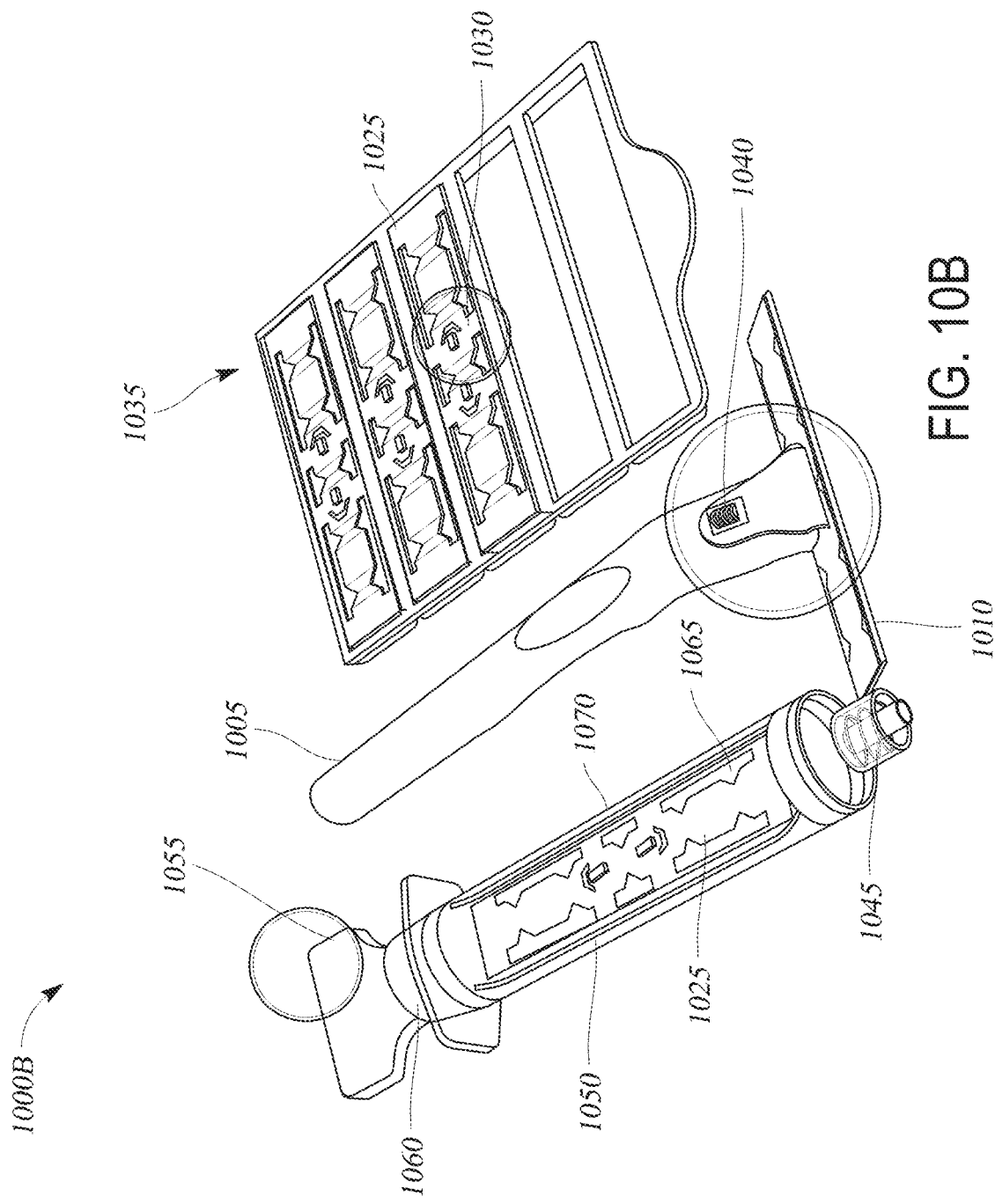

FIG. 10B illustrates another example of a contaminant collection device 1000B that can be used in hazardous contamination detection kits described herein. Similar to collection device 1000A, collection device 1000B includes a swab material 1010 attached to a handle 1005. A tray 1035 having a number of swab cartridges 1025 can be provided with the handle 1005. Each cartridge 1025 can secure a swab material to a first surface, and a second surface opposing the first surface can include an attachment device 1030 for releasably attaching to the handle 1005. As illustrated, attachment device 1030 can be a pair of prongs, or in other embodiments can be any suitable structure for press-fitting, snapping, hook-and-eye latching, or otherwise attaching to the handle. Handle 1005 can be provided with a release mechanism 1040, for example a button or lever, so that the user can release the cartridge 1025 and attached swab 1010 without contacting the swab 1010.

The contaminant collection device 1000B of FIG. 10B also includes a closed fluid transfer system 1050 for containing a used swab cartridge 1025 and attached swab 1010 between wiping the test surface and performing a test to analyze the sample. The closed fluid transfer system 1050 can include a handle 1060 having a grip portion 1055 and a cartridge well 1065 spaced away from the grip portion 1055 for securing a used cartridge 1025 away from the fingers of a user. The handle 1060 can be inserted into a fluid-tight container 1070 that sealingly engages the handle to prevent escape of enclosed fluids. The closed fluid transfer system 1050 can further include a fluid-tight fluid transfer mechanism 1045 in some embodiments, for example a needleless connector as described above, for transferring the enclosed fluid to a test device. Fluid can be expelled from the fluid-tight container 1070 in some embodiments by the user pressing or twisting the grip portion 1055 to compress or wring the enclosed cartridge 1025.

Figure 11:
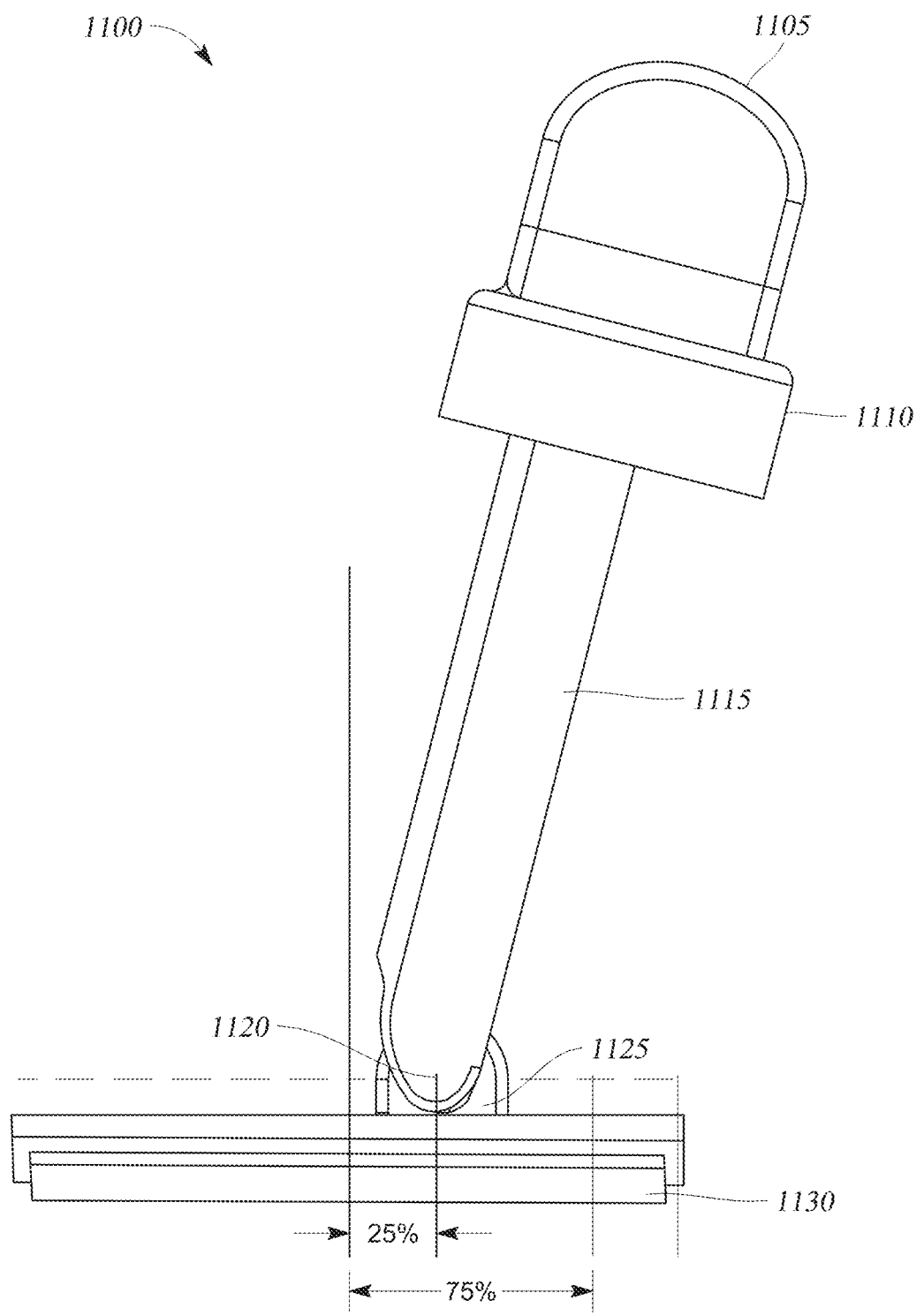
FIG. 11 illustrates an example of a pivoting collection device swab.

FIG. 11 illustrates an example of a pivoting collection device swab 1100 that can be used in hazardous contamination detection kits described herein. A handle 1110 includes a grip portion 1105, an elongate swab handle 1115 having a pivot 1120 connected to a swab head 1125, and a swab 1130. Such a pivoting head can be used, in some examples, in the collection device 400 described above.

The benefits of a pivoting head are two-fold. First, the pivoting head enables the user to have access to a large swab head reducing the need for multiple passes when swabbing the potentially contaminated surfaces. Second, the pivoting head creates a compact swab handle/vial system when the handle is inserted into the buffer vial enabling a minimal amount of buffer required as well as requiring minimal storage space. The buffer vial (not shown, see FIG. 4 for an example) can also be designed to be long and slender and interact with the swab-head such that when the swab-head handle is inserted into the buffer vessel it will serve to agitate the swab material facilitating a more efficient release of the collected sample into the buffer material. This can be accomplished via a snug-fit as well as internal geometry (ribbing, bumps, bottle-neck, etc.) to compress/agitate the swab 1130 when the handle is inserted into the container. A variation on the design is to mold the vial out of a softer compliant plastic allowing the user to squeeze the tube against the inserted swab head facilitating a greater release of sample from the swab head.

The pivoting joint 1120 that connects the swab head to the handle can be located anywhere along the swab head. Another aspect of this embodiments involves moving the pivoting location away from the center toward one end of the swab head 125. This can cause the swab head to rotate from the horizontal wiping/sampling position into a more vertical position to more easily present the swab head into the more compact vial. This also has the advantage that any residual fluid would pool up at the distal end of the swab head when it is rotated and drip into the vial, as opposed to dripping on the table or sampling surface. Reducing lost volume of captured fluid and drug is also beneficial for more accurate sampling results. In the illustrated embodiment, the preferred position of the pivoting joint ranges from about 25% to 75% of the distance from the center of the swab/wipe head to the end of the swab head. This can provide enough stability when wiping and an increased tipping moment when lifted from the surface and presented at the vial to complete the remainder of the process.

When pressed against the surface to be swabbed, the swab head 1125 complies in a rotating motion to lay flat against the surface, thereby providing contact between a larger surface area of the swab material and the test surface compared to non-pivoting embodiments that may be positioned at an angle to the test surface. Upon completion of swabbing, the handle can be inserted into the vial and the swab head can rotate in-line axially with the handle, enabling it to slide into a slender buffer vial. The insertion of the handle into the buffer vial can simultaneously agitate the swab material to express out both diluent and collected sample substances into the vial.

The embodiment of FIG. 11 can provide several advantages: 1) a larger swab-head surface reducing the number of passes along the surface that would be required to collect the sample, 2) a matching vial which can continue to be slender and compact reducing the need for a large amount of diluent, and 3) providing a more robust handle configuration so the user can press against the surface with an adequate amount of pressure (test results indicate that pressure and friction are the leading success factors to obtaining an adequate amount of substances from the surface).

An example of using the swab 1100 of FIG. 11 is shown in FIGS. 3A and 3B.

Figure 12:
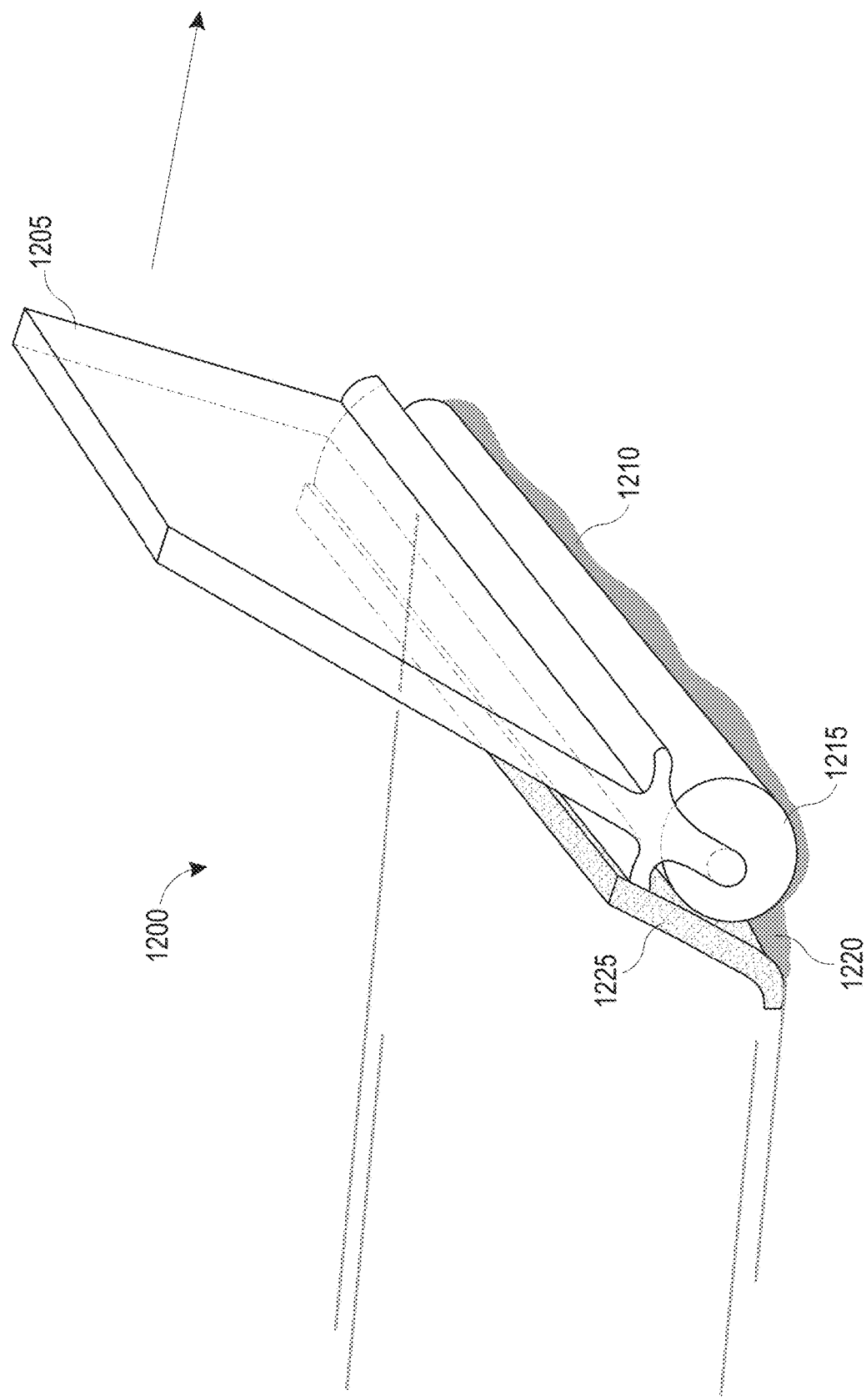
FIG. 12 illustrates an example of a collection device including a squeegee.
Figure 13B:
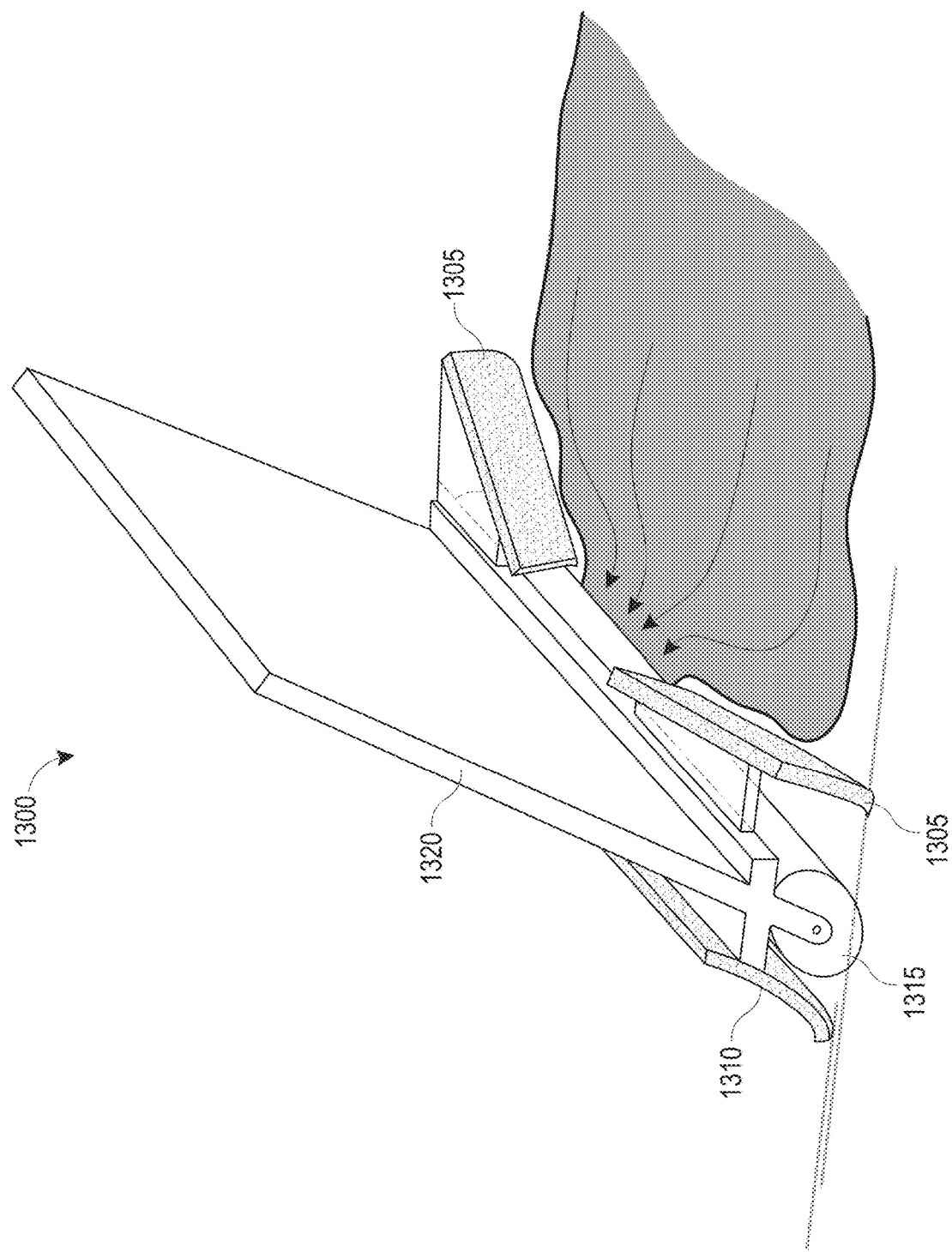

Contamination collection devices described herein can be designed to improve the efficiency terms of the concentration equation above, for example as illustrated in FIGS. 12 and 13A-13B. If the pick-up efficiency level can be increased, and the variation in pick up efficiency can be lowered, then efficiency can be increased to its highest possible level (with low variability) and the determined concentration will be more accurate. If the pick-up efficiency is too low the result would be a false negative result to the end user. If the user thinks that their collection kit picked up all of the drug on the contaminated surface for testing but in reality it did not, then contamination would remain on the test surface, and the reader would read a value that is lower than it should be. This lower value could lead to a false reading, and individuals in the contaminated environment could be exposed to possibly more hazardous values.

The embodiments of FIGS. 12 and 13A-13B reduce the number of collection steps by utilizing and combining two technologies in the pick-up process. A swab can be used to dispense liquid buffer solution onto the test surface, then a squeegee can be used to collect the buffer and wiped solution and concentrate it into a pool for the swab to re-absorb. The combination of these two elements integrated in the same device in close proximity can simplify the workflow of wetting and wiping the wetted surface. As a result of having a combined squeegee feature directly behind or in close proximity to the swab, the squeegee feature wipes the surface and the swab is in such close proximity that it automatically re-absorbs the fluid.

The friction and pressure generated by the squeegee can leave a potentially contaminated surface more "clean" from contaminants than it was prior to testing by wiping and concentrating the contaminated drug and providing the solution in close proximity to the swab for pick-up. The use of the squeegee and swab together can allow the user to use fewer steps in the collection and wiping process and provide higher pick-up efficiencies with lower variation.

FIG. 12 illustrates an example of a squeegee collection device 1200 that can be used in hazardous contamination detection kits described herein. The squeegee collection device 1200 includes a handle 1205, a swab 1210 coupled to one end of the handle, and a squeegee 1225 that trails behind the swab 1210 when wiped across a surface in order to collect liquid 1220 not initially picked up by the swab between the squeegee 1225 and swab 1210. The handle 1205 can be held by a user manually operating the squeegee collection device 1200 in some embodiments. In other embodiments, handle 1205 can be modified or omitted in order to couple the squeegee collection device 1200 to an automated system for wiping a test surface automatically and autonomously. The automated system can be provided with a motorized drive mechanism and instructions for traveling across, and collecting sample from, a predetermined area.

FIGS. 13A and 13B illustrate another example of a squeegee collection device 1300 that can be used in hazardous contamination detection kits described herein. FIG. 13A illustrates a top view of the squeegee collection device 1300 and FIG. 13B illustrates a perspective view of the squeegee collection device 1300. The squeegee collection device 1300 includes a handle 1320 and a swab 1315 coupled to one end of the handle. Squeegee collection device 1300 also includes a trailing squeegee 1310 that trails behind the swab 1315 when wiped across a surface in order to collect any liquid not initially picked up by the swab between the squeegee 1310 and swab 1315. Squeegee collection device 1300 also includes a pair of lead directing squeegees 1305 that direct fluid in front of the device 1300 inward (toward a center axis of the device) toward the swab 1315. This can allow for a decreased size of the swab 1315 and trailing squeegee compared to the embodiment of FIG. 12.

Providing at least a trailing squeegee as shown in FIGS. 12 and 13A-13B can improve collection efficiency by collecting fluid that the swab would not ordinarily absorb as it travels over the fluid, thus exposing the swab to the fluid for a longer time and allowing the swab to absorb the excess fluid. Thus, in the embodiments of FIGS. 12 and 13A-13B, the absorbent swab and squeegees can contact different portions of the test surface simultaneously when in use.

Figure 14A:
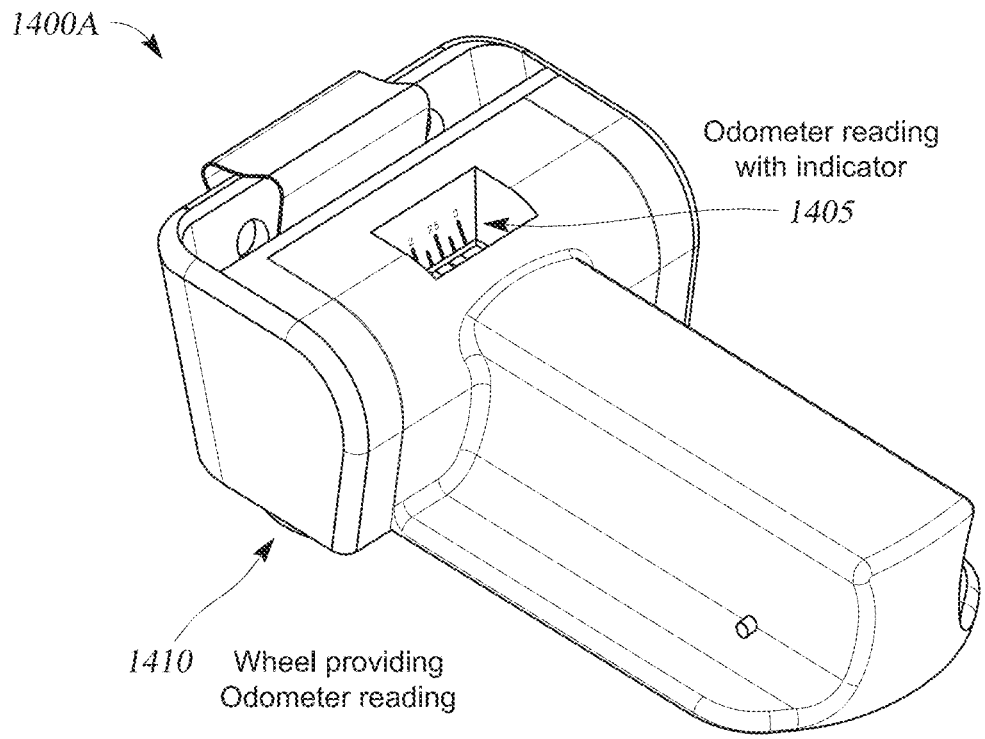
FIGS. 14A-14D illustrate various embodiments of a collection device with a built-in odometer.
Figure 14B:
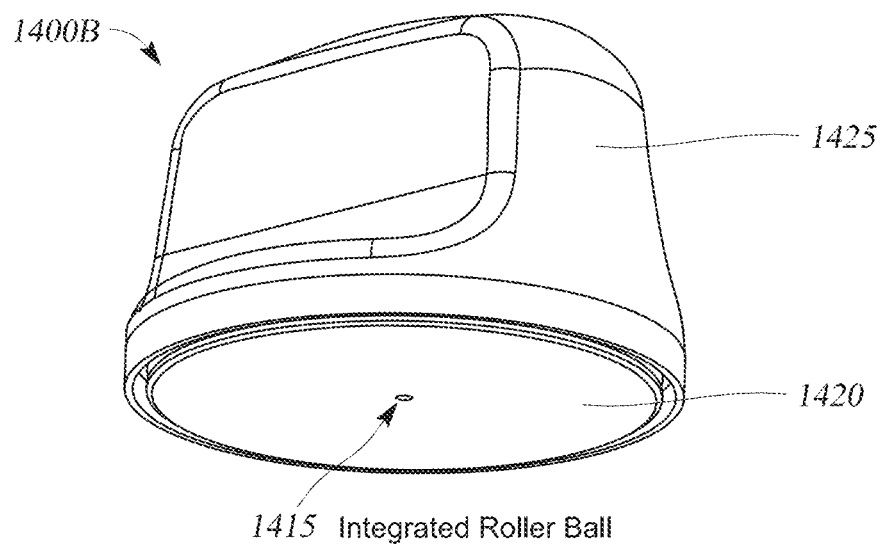
Figure 14C:
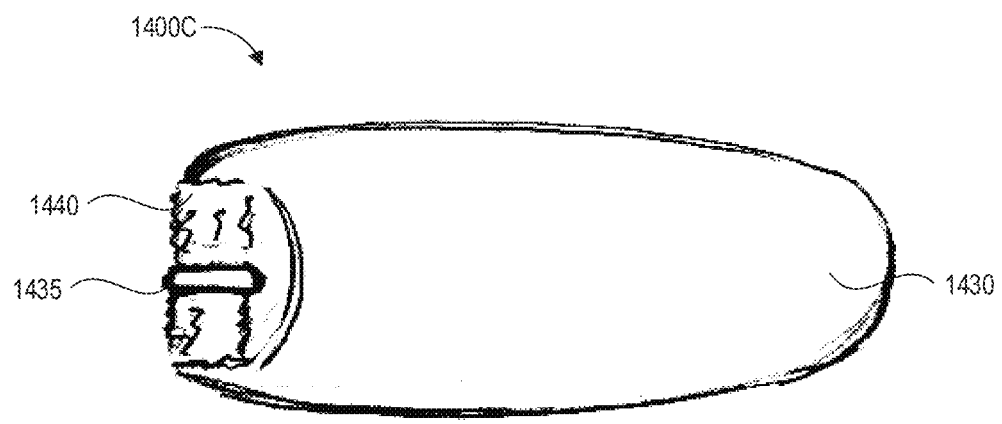
Figure 14D:
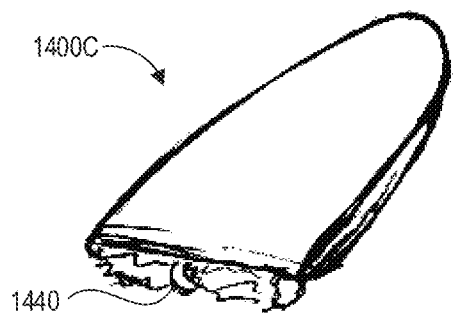

In order to track the area swabbed for more accurate test result calculations, some embodiments of the disclosed collection devices can include an odometer to track the distance that the collection device has traveled. This distance can be displayed to the user and manually entered into a detection device or electronically transmitted from the contaminant collection device to the detection device in various embodiments. FIGS. 14A-14D illustrate various embodiments of a contaminant collection device with a built-in odometer. FIG. 14A illustrates a distance-tracking collection device 1400A that has a wheel 1410 configured to track the distance that the device 1400A travels as it is rolled across a surface, and also includes a display 1405 for providing an odometer reading. FIG. 14B illustrates a distance-tracking collection device 1400B that includes a handle 1425, swab 1420, and a roller ball 1415 integrated into the swab area to provide for tracking of the distance traveled by the swab. Although not illustrated in FIG. 14B, a distance-tracking collection device 1400B can include a display for displaying an odometer reading to the user. FIG. 14C illustrates a top view of a distance-tracking collection device 1400C that includes a handle 1430, a swab 1440, and an integrated roller wheel 1435 centrally located in a swab 1440. FIG. 14D illustrates a front perspective view of the distance-tracking collection device 1400C.

Another embodiment can include a swab provided integrally with an assay test strip such that a user can directly capture a sample from a surface using the test strip.

Overview of Example Fluid Removal

Figure 15:
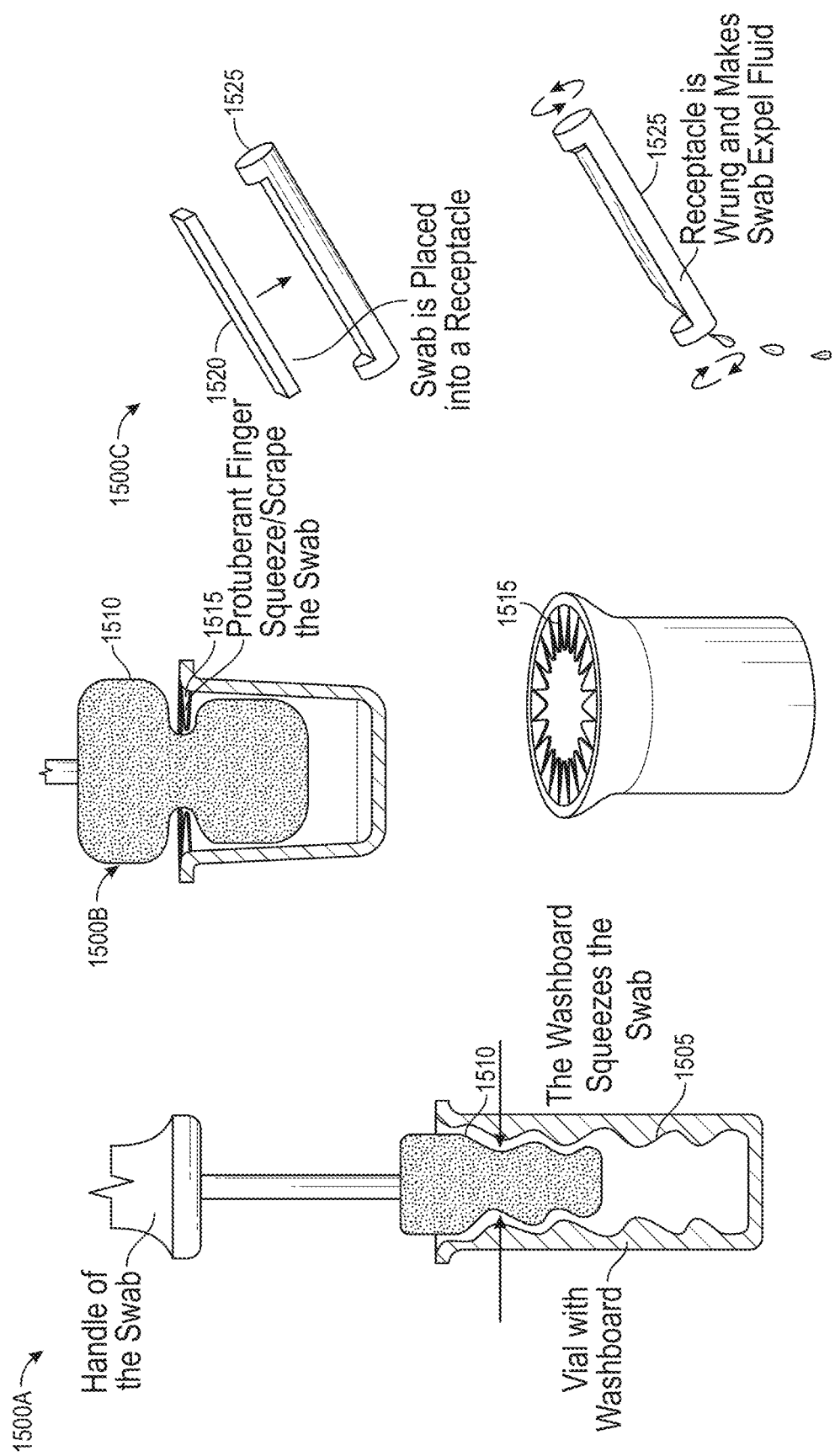
FIG. 15 illustrates various examples of removal of fluid from a collection device swab.

FIG. 15 illustrates various examples of removal of fluid from swabs in contaminant collection devices 1500A, 1500B, and 1500C. One embodiment of a contaminant collection device 1500A can include ridges 1505 along an interior of a container sized such that, when a swab 1510 is inserted into the container, the ridges compress the material of the swab 1510 in order to expel collected fluid from the swab 1510. Another embodiment of a contaminant collection device 1500B can include one or more layers of circumferentially disposed protrusions 1515 at or near an entrance to the interior of the container and/or disposed along the interior sides of the container. The protrusions 1515 can squeeze and scrape the swab 1510 as it is inserted into the container in order to expel collected fluid from the swab 1510. Another embodiment of a contaminant collection device 1500C can include a flexible container 1525 sized to receive a swab 1520 and configured to be wrung, where sides of the swab are rotated in opposing directions, in order to expel fluid from the swab 1520. In some cases, a controlled volume of fluid can be expelled from one end of the flexible container 1525 as the ends are twisted in opposing directions.

Figure 16:
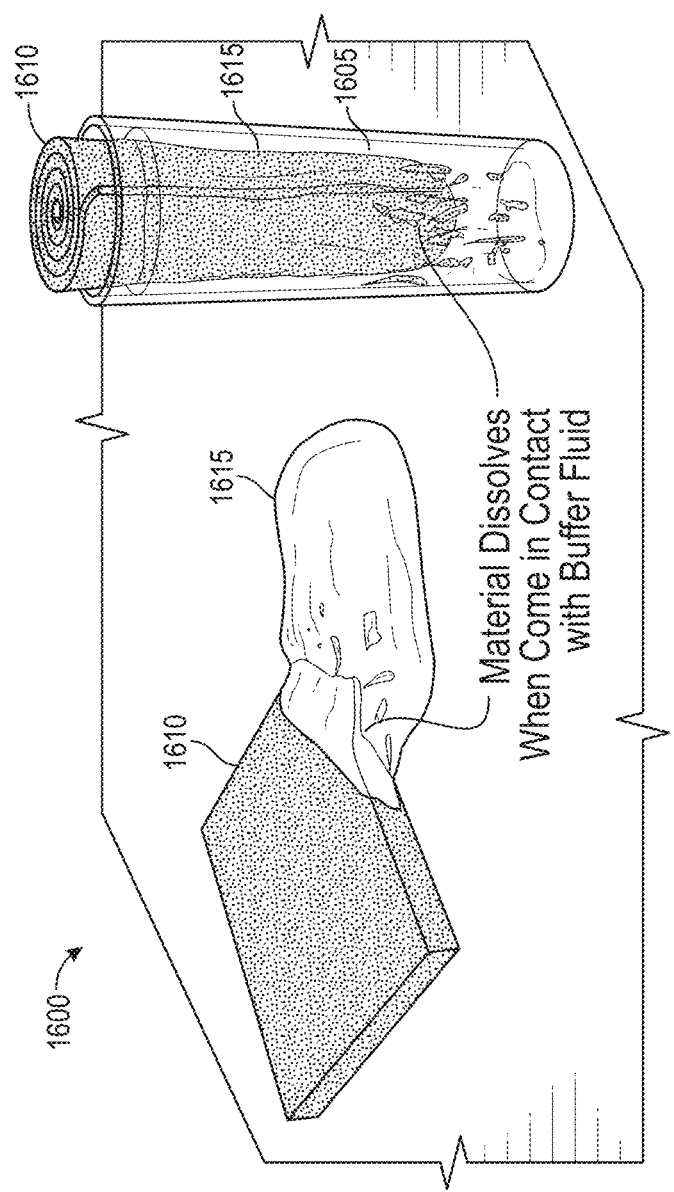
FIG. 16 illustrates an example of a dissolvable swab.

FIG. 16 illustrates an example of a dissolvable swab system 1600 that can be used in hazardous contamination detection kits described herein. In some embodiments, swab 1610 can be constructed from a material that dissolves upon contact, or after prolonged contact, with a buffer solution or other liquid. In some embodiments, a first buffer solution can be provided to the test surface for lifting contaminants off of the surface for pick-up by the swab, and the swab may not dissolve in contact with the first buffer solution so that the swab can be used to wipe the entire demarcated area. A second buffer solution or other liquid 1615 can be contained within container 1605 to dissolve the swab 1610 into the liquid of the container after the swab 1610 is introduced into the container. Dissolving the swab into the liquid in the container can provide the benefits of a more homogenous mixture for testing and of not retaining any contaminant in the swab when the container liquid is transferred to a detection device.

Figure 17:
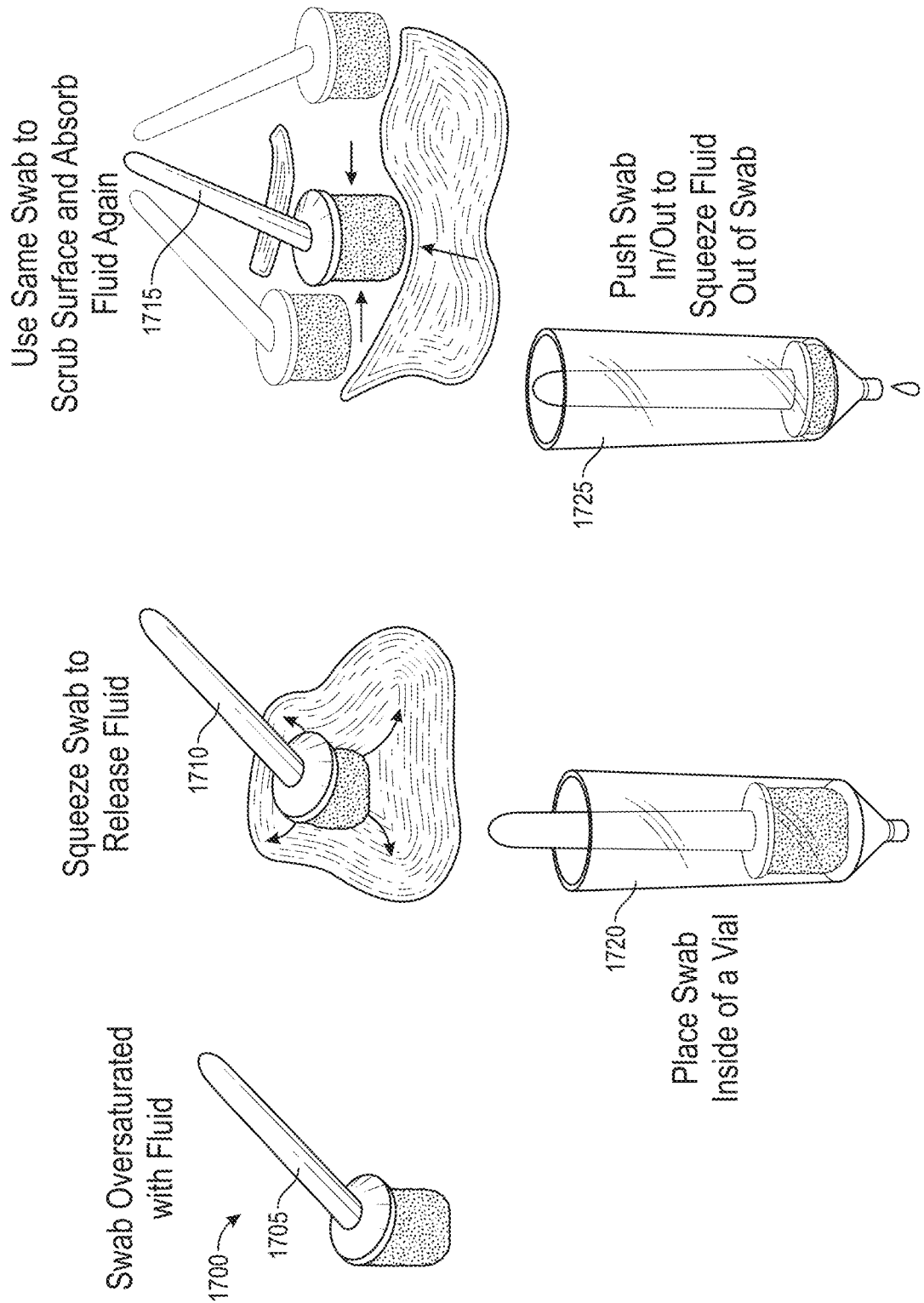
FIG. 17 illustrates example steps for absorbing and removing fluid from a collection device swab.

FIG. 17 illustrates example steps for a method 1700 of collecting contaminant from a test surface using an oversaturated collection device swab. The method 1700 can be implemented by any of the contaminant collection devices described herein.

At step 1705, a user can obtain a fully saturated swab attached to a handle, for example by withdrawing the swab from its own packaging or from a pre-filled collection container. Fully saturated as used herein refers to the swab containing a sufficient volume of fluid such that, when compressed, the swab material will release the fluid to a relatively large area (larger than the area directly contacted by the swab) of the test surface. Fully saturated swabs can contain all of a desired volume of liquid such that the liquid does not drip out of the material. In other embodiments a swab that is oversaturated (such that liquid is intended to drip out of the material) can be provided.

At step 1710, the user can squeeze the swab, such as by pressing the swab against the test surface while holding the handle, causing fluid to be expelled from the swab.

At step 1715, after (or as) the fluid is expelled the user can scrub or wipe the surface, passing the swab material over the expelled fluid, until it is completely or almost completely absorbed into the swab again. In some embodiments, steps 1710 and 1715 can be repeated over different areas of a demarcated test surface area until the entire area has been swabbed.

At step 1720, after acquiring the sample from the test surface, the user can place the swab into a vial in order to contain the fluid.

At step 1725, the user can squeezing the swab again by compressing the material into the bottom of the vial, thereby expelling the sample. In some embodiments, the vial can be coupled to a separate collection chamber so that the expelled fluid is stored for testing and not re-absorbed into the swab. The user can subsequently transfer the fluid from the vial or collection chamber to a detection device via any of the open or closed fluid transfer systems described herein.

Overview of Example Networked Testing Environment

Aspects of the present disclosure relate to a contamination test data management system. There are drug preparation systems, surface contamination tests, and healthcare worker safety procedures in the hospital and other healthcare delivery environments. These three areas are connected only to the extent that they have a common goal: to reduce or eliminate healthcare worker exposure to hazardous drugs, and to ensure patients are provided correct drug doses. The described hazardous contamination detection kits, systems and techniques improve upon existing approaches by linking these three areas, sensing patterns and trends, and targeting worker feedback and training. By creating and analyzing associations between data regarding dose preparation, personnel activities, and contamination test results, the disclosed systems can provide information to healthcare workers and management targeted at risk identification, feedback, and training. A beneficial outcome can include behavioral and/or workflow changes to reduce exposure risk in the test areas.

There are several existing solutions for assisting with pharmacy (or other clinical setting) drug preparation workflow. Each of these systems is designed to enhance patient safety through automated preparation or verification steps in compounding drugs. These systems are often used with hazardous drugs, such as chemotherapy agents, because there is little room for error with these drugs due to the health risks of exposure to even trace amounts. One such system performs automated dose calculation, weight-based (gravimetric) preparation and verification, integrated drug and consumable barcode verification, real-time automated documentation of the compounding process, and step-by-step compounding guidance. Other examples can employ a camera that captures images of products used in dose preparation and optionally an integrated weighing scale design with step-by-step guidance and automatic documentation.

While these systems help automate several aspects of drug preparation, they do not address pre- and post-preparation issues in the pharmacy, such as managing data associated with surface contamination testing (for example, floors, walls, hoods, etc.). They also do not manage data associated with air testing, nor data from testing individuals via fingertip, urine, blood or any other personal exposure monitoring.

Surface wipe tests are available from companies such as ChemoGLO™ which provide quantitative analysis of the antineoplastic agents 5-fluorouracil, ifosfamide, cyclophosphamide, docetaxel and paclitaxel. An example existing kit contains enough materials to conduct six surface wipes. The wipes and samples are sent to an outside laboratory, and reports are provided back to the test location within three to four weeks. Such tests and delayed reports are disconnected processes from day to day activities in the pharmacy.

Hazardous drugs, particularly chemotherapy drugs, are known to contaminate surfaces and air in pharmacies and other patient care settings, which presents a significant health risk to pharmacy and other healthcare workers. Further, the United States Pharmacopeia (Cpater 797, 28th Rev) recommends sampling of surfaces for contamination with hazardous drugs at least every six months. With improved testing technology, better feedback and improved outcomes, the frequency of testing is expected to become a more routine activity.

Figure 18:
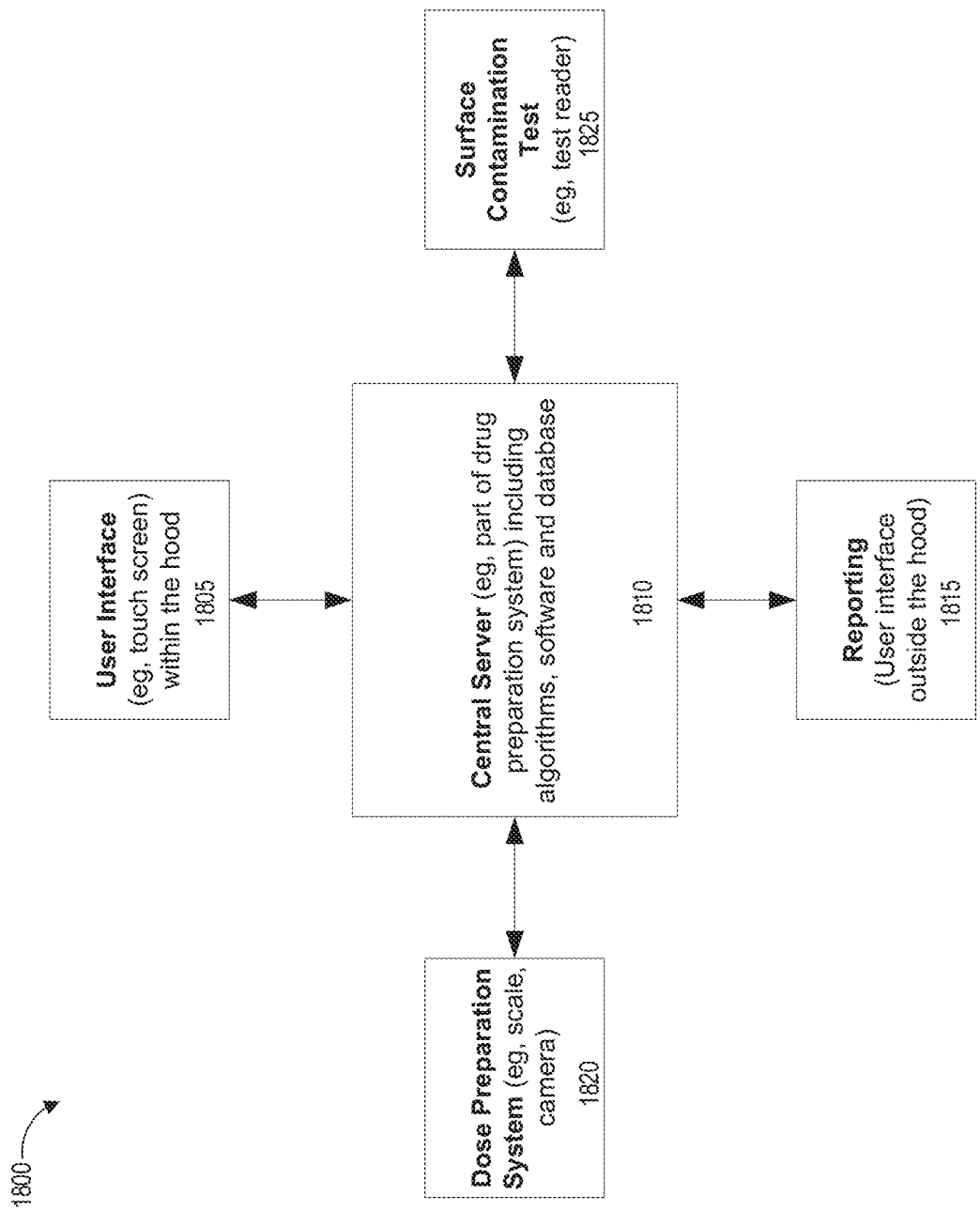
FIG. 18 depicts a high level schematic block diagram of an example networked test system environment.

FIG. 18 depicts a high level schematic block diagram of an example networked test system environment 1800. Hazardous contamination detection kits described herein can be used in the networked test system environment 1800 to improve contamination detectin, risk identification, feedback, and training. The networked environment 1800 includes a user interface 1805, dose preparation system 1820, surface contamination test 1825, and reporting system 1815 in network communication with a central server 1810 (and/or one another) via a network. The network can be any suitable data transfer network or combination of networks including wired networks and/or wireless networks such as a cellular or other publicly accessible network, WiFi, and the like.

The user interface 1805 supports system interaction by the test operator and can be located in the work area, for example in or near the testing environment. This facilitates interaction without the test operator having to remove and reapply personal safety equipment in order to use the system.

The dose preparation system 1820 can be hardware associated with a gravimetric dose preparation system, a scale, robotics, or devices that are designed to assist in the preparation of safe drug doses for the patient.

The surface contamination test 1825 can include a local test processing system which is in network communication with at least the central server 1810. For example, the local test processing system can be the assay reader device 800 of FIG. 8.

Central server 1810 can implement the algorithms, decisions, rules, and heuristics involved with management of contaminant testing data, and can store data (individual and aggregate), handle data input and/or output, generate reports, provide the user interface, and the like. Though referred to as a central server, these functions could be carried out in a distributed fashion, virtually, in any location.

The reporting user interface 1815 can provide raw and processed data to the user or safety manager regarding the relationship between activities in the pharmacy and test results.

In some implementations, the above descriptions apply to tests that are performed immediately in a pharmacy, hospital, or other clinical setting. However, the described testing is not limited to architectures where instant, immediate, or real-time connectivity is available. For example, if a local wipe test processing system is not available, data from a remote system can be transmitted to the central server using any number of methods. Results from tests may be fed in to an interface manually, electronically encoded, or in machine readable format. Data networks (e.g., internet, wireless, virtual private, cloud-based) can be used to input data from a remote lab (outside the pharmacy, hospital, or clinic) that performs testing either immediately or at a later time. The main difference between immediate local contamination detection versus remote testing is a potential time delay. As described above, current contaminant detection occurs in a two-step process with the steps performed at different locations. First, collection happens at site of possible contamination. Collection occurs a time A. Second, detection of the contamination occurs in a laboratory facility geographically separate from the contamination. Detection occurs at a time B, which is weeks or even months after collection occurred. The present disclosure provides a system including collection device and detection device in one kit. Using the disclosed kit, collection and detection occur at the site of possible contamination, and detection occurs within minutes of collection. For example, collected fluid can be provided onto an assay immediately (for example, within seconds such as but not limited to within 1, 2, 3, 4, 5, 10, or 15 seconds) after agitation of the fluid within a container as described herein. The collected fluid can be provided to the assay for up to 3 hours (360 minutes) after agitation in some embodiments. In some embodiments, instructions for use include a recommendation to the user not to apply the collected fluid to the assay more than 3 hours after collection because accuracy may decrease after 3 hours. After the fluid is added to the assay it can take around five minutes to fully develop in some non-limiting examples. In one advantageous implementation, the assay is read by a detection system around the time of its complete development. As such, the disclosed kits can provide test results indicating the presence, absence, and/or degree of contamination between 2-365 minutes after completion of sample collection, in some embodiments. Laboratory testing of embodiments of test kits described herein has demonstrated that reliable results can be obtained within about 5 minutes of completion of sample collection, and in some cases in as little as 2 minutes of completion of sample collection. This represents a dramatic improvement in the time to obtain a test result indicating the presence, absence, and/or degree of contamination of a hazardous drug over prior systems.

Embodiments of the system 1800 described herein directly link activities performed in the test environment to test results. For example, the system 1800 can directly link contaminant test results to when activities (for example, during antineoplastic drug preparation, dosing, and the like) were performed, who performed these activities (for example, through authentication), where the activities occurred (which hood, nearby floor, air test), and other events (such as spills, wasting of materials, or improper waste disposal) which can be manually or automatically recorded. In some embodiments, the central server 1810 can perform analysis of the related information to identify trends in hazardous contamination levels, and can output recommendations for preventing or mitigating hazardous contamination levels in certain areas.

Figure 19:
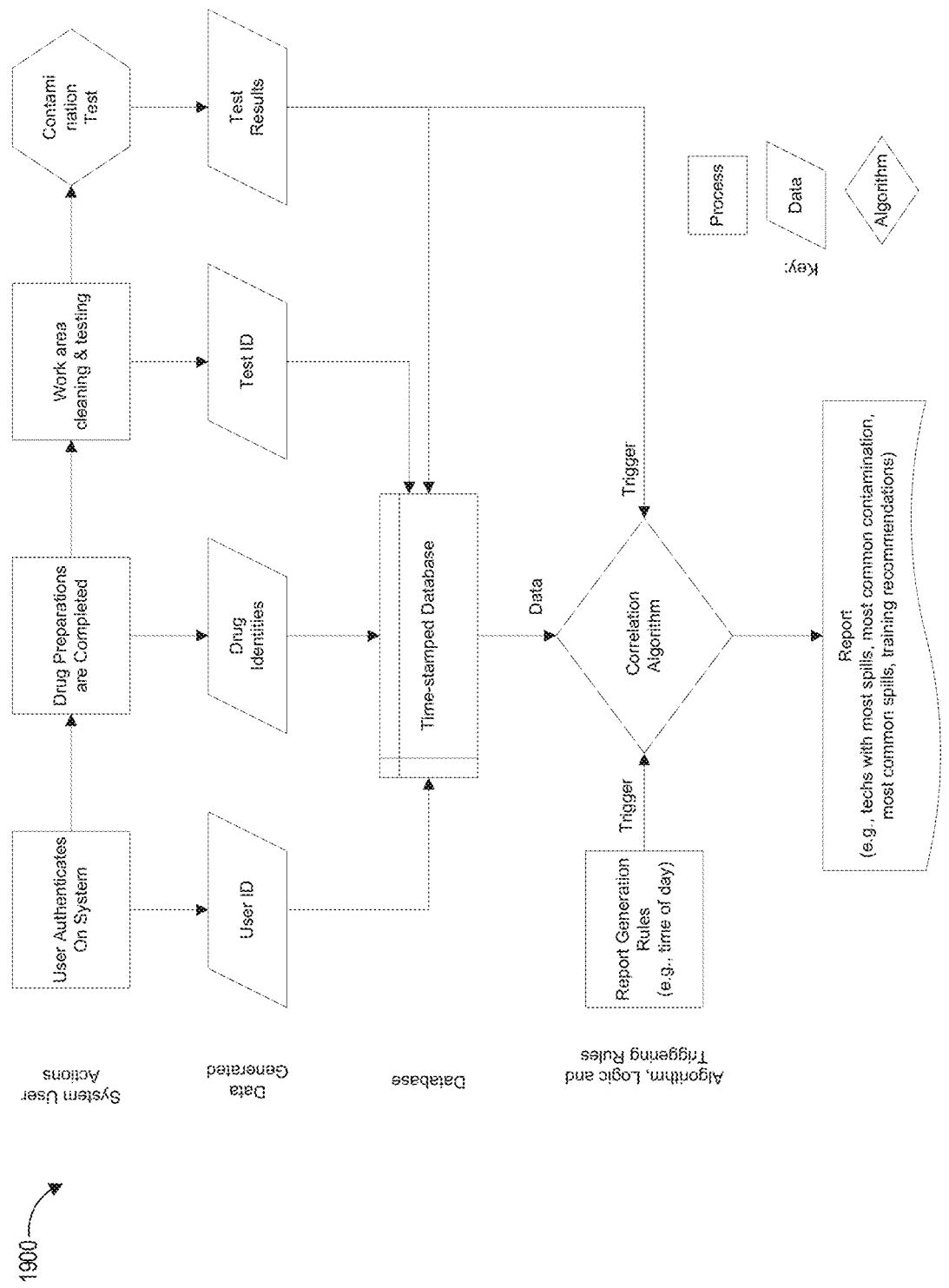
FIG. 19 depicts a flow chart of an example process for test data generation, analysis, and reporting.

FIG. 19 depicts a flow chart of an example process 1900 for test data generation, analysis, and reporting that can be implemented in some embodiments of the system 1800 of FIG. 18.

The dose preparation system 1820, whether volumetric, gravimetric, photographic, or bar code scanning, can be capable of keeping a record of every dose that was prepared in a particular pharmacy hood or other work area or clinical care area, when the dose was prepared and/or administered, and who prepared and/or administered the dose (for example, the identity of the pharmacy technician). As described above, this information can be correlated with the results of the contamination test.

The correlation algorithm can, in some embodiments, match detected contamination with specific personnel who might have created or contributed to the contamination. For example, if three technicians worked in a hood, and only one worked with compound x, and compound x was identified in a contamination test, then the technician who worked with compound x might be targeted for training or follow up testing.

The correlation algorithm can, in some embodiments, provide contamination test guidance by limiting tests to compounds that were actually used over a period of time, or used since the last contamination test. In a scenario where more than one test is required to screen for multiple possible contaminants, the cost may increase for a number of reasons. For example, it may take a longer period of time to perform testing due to more samples being needed. The time it takes to run a test may be longer. Sample preparation may be more complex. Each test may have an incremental cost, so tailoring tests may lower the overall cost. Advantageously, the dose preparation system could direct the user, or an automated system, to perform only contamination tests for drugs that were prepared in a specific location or hood.

The correlation algorithm can, in some embodiments, improve the specificity of contamination tests by utilizing a priori knowledge of drugs that were prepared in the hood. For example, if a contamination test shows a positive result, but is not capable of indicating which of a family of possible contaminants actually has been identified, the database of drugs prepared in the hood could be queried for all of those possible drugs, and the test result narrowed to the ones actually prepared. In some implementations, further testing can be performed for those specific drugs.

The correlation algorithm can, in some embodiments, determine systematic issues with devices used in preparing drugs. Drug preparation systems can have the capability to store information representing the products and devices used in drug preparation. For example, information on syringe types (manufacturer, volume etc.), closed system transfer devices, connectors, spikes, filters, needles, vials, and IV bags, to name a few examples, can be stored along with the drug and diluent data in the preparation systems database. Failures can be linked to specific devices and directly help with risk mitigation.

The correlation algorithm can, in some embodiments, identify drug manufacturers, dose and containers that systematically fail, resulting in detected contamination. The correlation algorithm can identify procedures that commonly cause contamination, such as reconstitution steps.

The system 1800 can provide some or all of these analytics, alone or in combination, in various embodiments.

The system 1800 can be designed to implement workflows that are initiated based on a set of conditions. For example, one condition that can trigger a workflow is the detection of contamination. Examples of workflows are described below.

A decontamination workflow can include the following procedures. The system 1800 can instruct a user how to contain and decontaminate a specific area, depending on what area the test was performed in. Instructions can include audio, text, video, and the like. After decontamination, the workflow can continue to instructions on performing repeat contamination tests to ensure the area was properly decontaminated. If testing fails again, the decontamination procedure can be repeated.

The system 1800 can be configured to provide instructions through the user interface 1805 and/or dose preparation system 1820 (or any other means of communication, including printed instructions, other displays, voice output and input, direct messages to designated users, etc.). These instructions can be configured to be specific for certain sources of contaminants.

Another example workflow is repeat testing of the area of contamination, prior to decontamination. This may be a useful workflow if the specificity of a particular test is not high. The objective could be to re-test with the same test, or perform further tests to identify more specifically, what the source and/or level of contamination is. A follow-on step could be specific decontamination instructions, already described above.

In various workflows, system 1800 can be configured to receive, prompt, and/or wait for input during the workflow to acknowledge completion of each step. The system 1800 can be configured to capture decontamination procedure evidence, such as photographic, video, audio, proximity information for future review, training, documentation, and the like.

System 1800 can be configured to identify risks from preparation issues. For example, the system 1800 can analyze data already captured by a drug preparation system, or provide means to capture data regarding drug preparation issues, problems or errors. For example, when material is wasted, the user involved can be questioned about whether there was a spill or any surface contamination that caused the wasting. System 1800 can link wasting with positive contamination tests, if wasting is commonly caused by spills.

System 1800 can be adapted for use in non-pharmacy healthcare environments including, but not limited to, hospitals, clinics, hospice environments, and veterinary treatment centers. The system 1800 can be adapted to other areas of patient care, such as the patient floor, nursing, drug delivery (e.g., infusion, injection), patient room, bathroom, etc. Contamination tests can be performed in any of these settings, and this data can be fed back to the system 1800. As described above, detected contamination can be correlated with personnel, protocols followed, specific drugs, devices, locations, and any other parameter of interest. Any parameter around the delivery of drugs that can be encoded can be correlated with the presence of contamination to provide feedback to risk managers, clinical and pharmacy personnel. Further, dose preparation and dispensing can occur in many locations outside the pharmacy, and similar workflows can be employed in those areas, including remote contamination test preparation and execution.

The physical location of specific functions performed by the system 1800 are not restricted to the pharmacy or hospital data center. Any structure or function of the system 1800, including the database, correlation and analysis, data entry, data display, reporting, etc., can be carried out in any system in any location. A system model may be to have a central web-based service, for example. Another model may be to have remote reporting and notification capability through remote devices like smart phones, pagers, computers, displays, applications etc.

Supply of devices can be automated through any of the previously described systems. For example, pharmacies may be provided resupply of test kits by system 1800, and such resupply can be automated in some embodiments by managing an inventory of kits and initiating a resupply when stock falls below a certain level.

Overview of Example Swab Materials and Buffer Solutions

Considerations in the development and selection of swab materials and buffer solutions will not be described. Optimal swab materials and buffer solutions will be identified, but it will be understood that hazardous contamination detection kits described herein can use any suitable swab material and buffer solution. Three criteria for choosing a swab for use with the described contamination collection devices include the following. (1) Minimal background—Background is the amount of contaminant on a swab measured by the analytical technique after testing has been performed according to the analytical protocol before sampling. Blank contribution from the swab must be minimal. (2) High recovery rate—Recovery means the percentage of contaminant actually measured by the analytical technique when the swab is spiked with a known quantity of that species. In one non-limiting example, a sixty-percent recovery rate is deemed acceptable; however, higher recovery rates are desirable. (3) Low particle generation—It is desirable that the swabbing material leave the swabbed surface free from particles which would further contaminate the surface.

Through extensive testing, some of which is summarized below, it has been discovered that cleanroom-laundered, 100 percent continuous-filament, double-knit polyester materials can meet all the requirements for swabbing: minimal background, high recovery rates, and low particle generation. Swabs made with cleanroom-laundered 100 percent polyester-knit heads feature low particle generation and extremely low nonvolatile residues. Thus, some embodiments of the swabs described herein can include one or more layers of such material.

In some embodiments, swab material can be interrelated with the buffer solution. For example, polyester swabs can exhibit high collection efficiencies, but for buffer solution types with no surfactant, foam swabs can perform better than polyester swabs. Tris buffer and ChemoGlo solution are two suitable buffer solutions that can be implemented in contamination collection devices described herein. Other buffer solutions are also suitable, for example HEPES buffer. Polyester swabs can be used with Tris buffer and other solutions with surfactant, while foam swabs can be used with ChemoGlo or other drying solutions, such as those containing alcohol.

Implementing Systems and Terminology

Implementations disclosed herein provide systems, methods and apparatus for detection of the presence and/or quantity of antineoplastic agents or other environmental contaminants. One skilled in the art will recognize that these embodiments may be implemented in hardware or a combination of hardware and software and/or firmware.

The assay reader device may include one or more image sensors, one or more image signal processors, and a memory including instructions or modules for carrying out the processes discussed above. The device may also have data, a processor loading instructions and/or data from memory, one or more communication interfaces, one or more input devices, one or more output devices such as a display device and a power source/interface. The device may additionally include a transmitter and a receiver. The transmitter and receiver may be jointly referred to as a transceiver. The transceiver may be coupled to one or more antennas for transmitting and/or receiving wireless signals.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like. The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. Thus, the present invention is not intended to be limited to the implementations shown herein but is to be accorded the widest scope consistent with the principles and novel features disclosed herein.

What is claimed is:

1. A hazardous contaminant detection system comprising:
    a collection device comprising:
        a buffer solution configured to lift a hazardous contaminant from a test surface when the buffer solution is applied to the test surface,
        an absorbent swab material configured to absorb at least a portion of the buffer solution and to contact the test surface to collect the hazardous contaminant,
        a handle having a base portion and a grip portion, wherein the base portion is coupled to the absorbent swab material, and
        a container dimensioned to encase the base portion and the grip portion of the handle and the absorbent swab material and the buffer solution within a fluid-tight interior volume, the container having a nozzle including an orifice having a size and shape selected to control release of less than a total volume of the buffer solution from the interior volume, wherein the interior volume of the container has a first portion shaped to receive the base portion of the handle and a second portion shaped to receive the grip portion of the handle; and
    a detection device comprising:
        an assay test strip positioned to receive the volume of the buffer solution released from the container, the assay test strip comprising at least one reaction zone configured to produce an optically-detectable change in appearance in the presence of the hazardous contaminant, and
        an image sensor positioned to receive light reflected from the at least one reaction zone and configured to generate signals representing an intensity of the received light, and control electronics configured to analyze the signals and determine the presence of the hazardous contaminant in the at least one reaction zone.

2. The hazardous contaminant detection system of claim 1, further comprising a demarcation guide configured to specify an area of the test surface to be tested for contamination by the hazardous contaminant.

3. The hazardous contaminant detection system of claim 2, wherein the control electronics are configured to determine whether the hazardous contaminant is in contact with the at least one reaction zone based at least partly on the intensity of the signals and the area of the test surface.

4. The hazardous contaminant detection system of claim 1, wherein the assay test strip comprises:
a sample receiving zone for receiving the volume of the buffer solution released through the orifice of the nozzle; and
a length of material extending between the sample receiving zone and the at least one reaction zone and configured to wick at least the received buffer solution from the sample receiving zone to the at least one reaction zone.

5. The hazardous contaminant detection system of claim 1, wherein the container comprises:
an open end having an aperture into the interior volume; and
a releasable portion of the container including:
an attachment mechanism configured to releasably couple to the container over the open end to provide a fluid-tight seal with the interior volume of the container with the handle and the absorbent swab material and the buffer solution sealed within the interior volume,
the nozzle, and
a cap releasably coupled to the nozzle.

6. The hazardous contaminant detection system of claim 1, wherein the handle has a first T-shaped cross section, and wherein the interior volume of the container has a second T-shaped cross section sized to receive the first T-shaped cross section of the handle.

7. The hazardous contaminant detection system of claim 1, wherein at least a portion of the container is flexible such that the interior volume can be compressed to expel the volume of the buffer solution from the interior volume through the orifice of the nozzle.

8. The hazardous contaminant detection system of claim 1, wherein the detection device comprises a network connection interface, and wherein the control electronics are configured to send data representing whether the hazardous contaminant is in contact with the at least one reaction zone to at least one remote computing device over a network via the network interface.

9. A hazardous contaminant collection device comprising:
a container;
a buffer solution configured to lift a hazardous contaminant from a test surface when applied to the test surface;
an absorbent swab material configured to absorb at least some of the buffer solution and to contact the test surface to collect the hazardous contaminant; and
a handle comprising a base portion and a grip portion, wherein the base portion is coupled to the absorbent swab material, wherein the container is dimensioned to encase the base portion and the grip portion of the handle and the absorbent swab material and the buffer solution within a fluid-tight interior volume, and wherein the interior volume has a first portion shaped to receive the base portion of the handle and a second portion shaped to receive the grip portion of the handle, the container having a nozzle including an orifice having a size and shape selected to control release of less than a total volume of the buffer solution from the interior volume.

10. The hazardous contaminant collection device of claim 9, wherein the container comprises:
an open end having an aperture into the interior volume; and
a releasable portion of the container including:
an attachment mechanism configured to releasably couple to the container over the open end to provide a fluid-tight seal with the interior volume of the container with the handle and absorbent swab material and buffer solution sealed within the interior volume,
the nozzle, and
a cap releasably coupled to the nozzle.

11. The hazardous contaminant collection device of claim 10, wherein the attachment mechanism comprises threading along an interior surface of the releasable portion, and wherein the open end of the container comprises corresponding threading along an exterior surface of the open end.

12. The hazardous contaminant collection device of claim 9, wherein the handle comprises a T-shaped cross section defining:
a swab holding member having a flat first surface and a second surface spaced apart from the flat first surface, and
a handle portion extending away from the second surface.

13. The hazardous contaminant collection device of claim 12, wherein the absorbent swab material comprises two layers of fabric coupled to the flat first surface of the swab holding member.

14. The hazardous contaminant collection device of claim 13, wherein a width of the absorbent swab material is greater than a width of the flat first surface of the swab holding member.

15. The hazardous contaminant collection device of claim 14, wherein the absorbent swab material is coupled to the flat first surface of the swab holding member at opposing edges of the absorbent swab material with a gap between a central portion of the absorbent swab material and the flat first surface of the swab holding member.

16. The hazardous contaminant collection device of claim 12, wherein the interior volume of the container has a T-shaped cross section corresponding to the T-shaped cross section of the handle.

17. The hazardous contaminant collection device of claim 9, wherein the nozzle comprises a channel leading to the orifice, wherein a cross-section of the channel is shaped to release the volume of the buffer fluid one drop at a time.

18. A method of testing a test surface for the presence of a hazardous contaminant, the method comprising:
removing an absorbent swab material coupled to an elongate handle from fluid-tight packaging, the elongate handle comprising a base portion and a grip portion, the absorbent swab material pre-moistened with a first volume of a buffer solution configured to lift the hazardous contaminant from the test surface, wherein the absorbent swab material is impregnated with the first volume of the buffer solution;
wiping the test surface with the absorbent swab material to collect particles of the hazardous contaminant from the test surface;

inserting the absorbent swab material into an open end of a fluid-tight container, the fluid-tight container comprising a well containing a second volume of the buffer solution and a cap to seal the well, wherein the fluid-tight container is dimensioned to encase the base portion and the grip portion of the elongate handle and the absorbent swab material and the second volume of the buffer solution within a fluid-tight interior volume, and wherein the fluid-tight interior volume has a first portion shaped to receive the base portion of the elongate handle and a second portion shaped to receive the grip portion of the elongate handle;

sealing the fluid-tight container with the cap to isolate the first and second volumes of the buffer solution within the fluid-tight container;

agitating the fluid-tight container to release at least some of the collected particles of the hazardous contaminant into the buffer solution;

opening a sealable orifice of the cap;

transferring a third volume of the buffer solution from the fluid-tight container to an assay test strip through the sealable orifice;

inserting the assay test strip into an assay reader device; and based on an output of the assay reader device, identifying that the hazardous contaminant is present on the test surface.

19. The method of claim 18, further comprising compressing the interior volume of the fluid-tight container to expel the third volume of the buffer solution through the sealable orifice.

20. The method of claim 18, further comprising sealing the sealable orifice after transferring the third volume of the buffer solution.

* * * * *